US012637721B2

(12) United States Patent
Kayser et al.

(10) Patent No.: US 12,637,721 B2
(45) Date of Patent: May 26, 2026

(54) Y-CHROMOSOMAL SHORT TANDEM REPEAT MARKERS FOR TYPING MALE INDIVIDUALS

(71) Applicant: Erasmus University Medical Center Rotterdam, Rotterdam (NL)

(72) Inventors: Manfred Heinz Kayser, Rotterdam (NL); Arwin Ferdinand Ralf, Dordrecht (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 831 days.

(21) Appl. No.: 17/904,352

(22) PCT Filed: Feb. 19, 2021

(86) PCT No.: PCT/NL2021/050117
§ 371 (c)(1),
(2) Date: Aug. 16, 2022

(87) PCT Pub. No.: WO2021/167464
PCT Pub. Date: Aug. 26, 2021

(65) Prior Publication Data
US 2024/0209457 A1 Jun. 27, 2024

(30) Foreign Application Priority Data
Feb. 21, 2020 (EP) .................................... 20158807

(51) Int. Cl.
*C12Q 1/68* (2018.01)
*C07H 21/04* (2006.01)
*C12Q 1/6888* (2018.01)

(52) U.S. Cl.
CPC ..... *C12Q 1/6888* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

2018/0298453 A1 10/2018 Fang et al.

FOREIGN PATENT DOCUMENTS

CN 110551830 A * 12/2019 ........... C12Q 1/6858

OTHER PUBLICATIONS

Ralf et al. (Forensic Science International: Genetics, vol. 102595, Sep. 2021) (Year: 2021).*
Rothstein et al. (1994) PNAS USA 91: 4155-4159 (Year: 1994).*
NEB catalog (1998/1999), pp. 121, 284. (Year: 1998).*
Sulston et al. (Genbank Ac095380.1, Mar. 2003, âHomo sapiens PCR product GAP1622 from Y, complete sequence). (Year: 2003).*
Butler (Methods in Molecular Biology, Forensic DNA typing protocols, vol. 297, 2005). (Year: 2005).*
Hanson et al. (J. Forensic Sci. vol. 57, No. 1, Jan. 2012) (Year: 2012).*
Maybruck et al. (Forensic Science International: Genetics, vol. 4, pp. 11-20, 2009) (Year: 2009).*
International Search Report for corresponding International Application No. PCT/NL2021/050117, dated Jun. 15, 2021.
Liu Jinding et al., Develeopment of a new 17 Y-STRs System using fluorescent-labelled universal primers and its application in Shanxi population Forensic Science International: Genetics Supplement Series vol. 7. No. 1 (2019) 95-97.
Kaye N Ballantyne et al., "A new future of forensic Y-chromosome analysis: Rapidly mutating Y-STRs for differentiating male relatives and paternal lineages", Forensic Science International: Genetics, Mar. 1, 2012—ISSN 1872-4973, vol. 6, Nr:2, pp. 208-218.
Maybruck J L et al., "A comparative analysis of two different sets of Y-chromosome short tandem repeats (Y-STRs) on a common population panel", Forensic Science International: Genetics, Dec. 1, 2009 Elsevier BV, Netherlands—ISSN 1872-4973, vol. 4, Nr.1, pp. 11-20.
Hanson E K; Ballantyne J, "Population data for 48 'Non-Core' Y chromosome STR loci", Legal Medicne, Jul. 1, 2007 Japanese Society of Legal Medicine, Tokyo, JP—ISSN 1344-6223, vol. 9, Nr:4, pp. 221-231 5 XP022043875.
Leat; Ehrenreich N; Benjeddou L; Cloete M; Davison K; S, "Properties of novel and widely studied Y-STR loci in three South African populations", Forensic Science International, May 7, 2007 Elsevier B.V, Amsterdam, NL—ISSN 0379-0738, vol. 168, Nr:2-3, pp. 154-161.
Zhang G Q et al Genetics and molecular research vol. 11, No. 4 (2012) 4487-4500).
Kayser, "Forensic use of Y-chromosome DNA: a general overview", 2017. Human Genetics 136:621-635.
Ballantyne et al., "Mutability of Y-Chromosomal Microsatellites: Rates, Characteristics, Molecular Bases, and Forensic Implications" 2010. Am J Hum Gen 87: 341-453.
Goedbloed et al., "Comprehensive mutation analysis of 17 Y-chromosomal short tandem repeat polymorphisms included in the AmpFISTR® Yfiler® PCR amplification kit" 2009. Int J Leg Med 123: 471-482.

(Continued)

Primary Examiner — Jeanine A Goldberg
(74) Attorney, Agent, or Firm — Leason Ellis LLP

(57) ABSTRACT

The invention relates to a group of Y-chromosomal short tandem repeat (Y-STR) markers comprising at least one rapidly mutating (RM) Y-STR marker selected from the group consisting of DYF1000, DYF1001, DYF1002, DYR88, DYS685, DYS688, DYS712, DYS1003, DYS1007, DYS1010 and DYS1012. The invention further relates to a set of amplification primers comprising primers for the amplification of at least one Y-STR marker according to the invention, to methods for amplifying an allele of at least one Y-STR marker, to a kit for identifying an allele of a Y-STR marker by amplification and electrophoretic detection or sequencing detection, and by sequencing of non-amplified DNA, and to the use of the group of Y-STR markers for typing male individuals.

20 Claims, 17 Drawing Sheets

Figure 2:
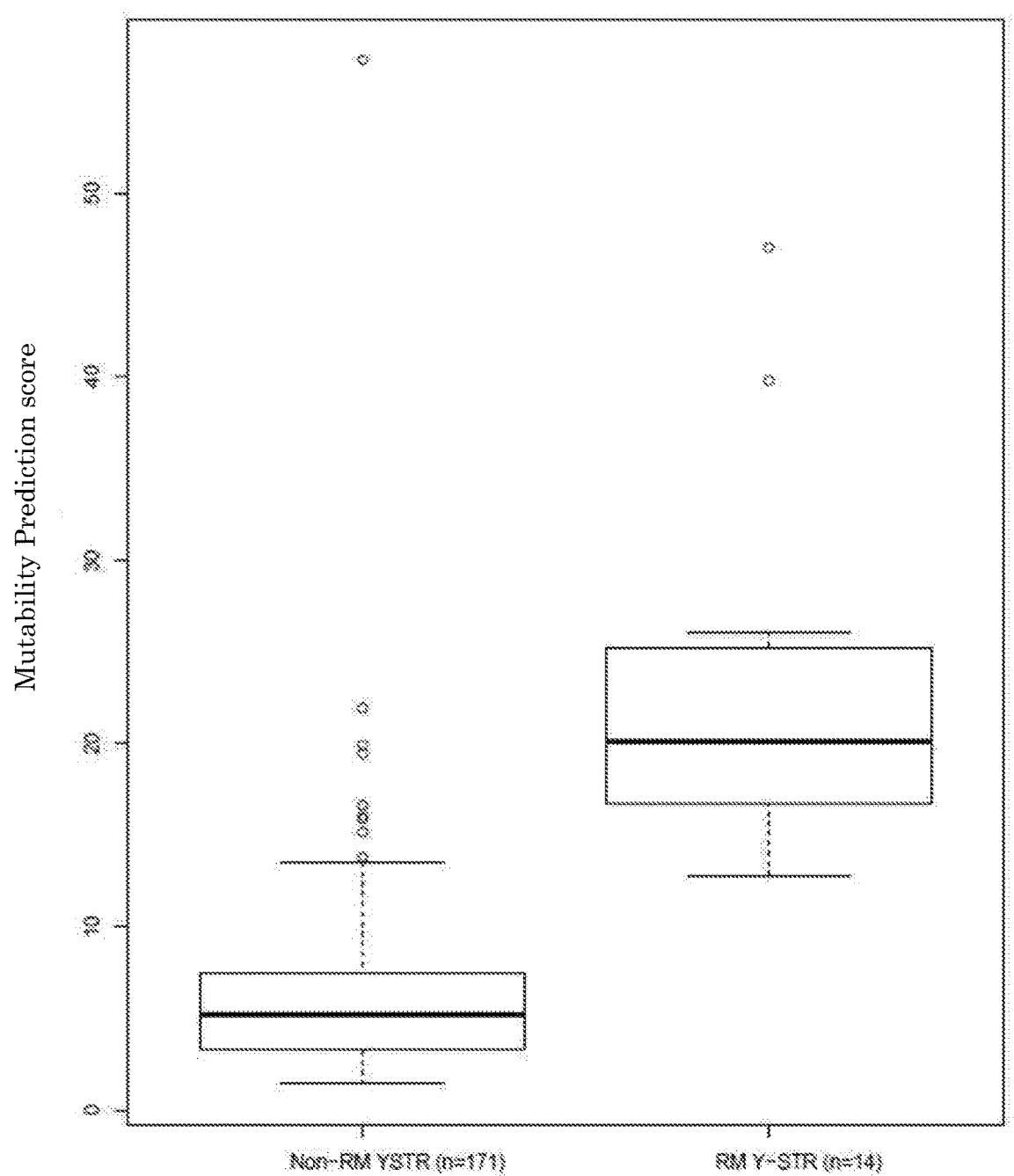

Specification includes a Sequence Listing.

(56) References Cited

OTHER PUBLICATIONS

Adnan et al., "Improving empirical evidence on differentiating closely related men with RM Y-STRs: A comprehensive pedigree study from Pakistan", 2016. Forensic Sci Int Genet 25: 45-51.

Claerhout et al., "Determining Y-STR mutation rates in deep-routing genealogies: Identification of haplogroup differences", 2018. Forensic Science Int: Genetics 34: 1-10.

Ballantyne et al., "Toward Male Individualization with Rapidly Mutating Y-Chromosomal Short Tandem Repeats", 2014. Human Mutation 35: 1021-1032.

Buel et al., "Capillary Electrophoresis STR Analysis: Comparison to Gel-Based Systems", 1998. J Forensic Science 43: 164-170.

Schneider et al., "Evaluation of GRCh38 and de novo haploid genome assemblies demonstrates the enduring quality of the reference assembly", 2017. Genome Res 27: 849-864.

Vallone, "AutoDimer: a screening tool for primer-dimer and hairpin structures", 2004. BioTechniques 37: 10.2144/04372ST03.

Eckert et al., "Every Microsatellite is Different: Intrinsic DNA Features Dictate Mutagenesis of Common Microsatellites Present in the Human Genome", Molecular Carcinogenesis 48:379-388 (2009).

* cited by examiner

Figure 1

DYS627 (Forward Primer – SEQ ID NO: 93; Reverse Primer – SEQ ID NO: 94)

CTAGGTGACAGCGCAGGATTCCATCTAAAAATCAAAAATCAAAGAGAGACACAGGGAGAAAGAAGAAAGAAGAAAGAAGAGAG
AGAGAGAAAGAAAGAAAGAAAGAAGAAAGAAAGAAAGAAAGAAAGAAAGAAAGAAAGAAAGAAAGAAAGAAAGAAAGAAAGAG
AAAGAGAGAGGGAGGGAGGGAGGGAGGGAGGGAGGAAGTAAGAAAGGTAAGGAAGGATGAACTAAGGAAGGAAGAAGGAAGGAA
CGAAGGAGAGAATGAAAGGCATAAAACCAAAGGGAAATGAATAAAAATAAAACTTGCCATTTGCTCATTATCC

[N]83[AG]6[AAAG]18[N]170

DYS526b (Forward Primer – SEQ ID NO: 99; Reverse Primer – SEQ ID NO: 100)

TCAGCAAACACCTTAGCTAATCATGATTCTTACCTTCGGTGAACTGATCCAAACCTTACTTATTTCTCCTTTTTCCTCTCCTCCCTC
CCTCCCTCTTCCTTCCTTCTTTCCTTCTTTCCTTCTTTCTTTCTTTCTTTCTTTCTTTCTTTCTTTCTTTCTTCCTTCTTCCTTCCTTCCT
TCCTTCCTTCCTTCCTTCCTTCCTTCCTTCCTTCCTTCATTCCTTCACTTCTTCCTTCCTTCCTTCCTTCCTTCCTTCCTTCCTTACTTTTT
CTATTTTCTTTCTTTCTCTATTTTTCTTTCTCTCTATTTTTTTCTCTCCTTCCTTCCTTCCTTCCTTCCTTCCTTCCTTCCTTCCTTCCTTC
TCTTTACCTTCTGGGGAAGTAACCC

[N]26[AAGG]14[N]113[AAGG]9[AAAG]13[N]123

Figure 4

DYF1000 (multi-copy marker)
chrY:17854578-17854919
chrY:18051088-18051432
chrY:24024183-24024480
chrY:25645653-25645953

TGGCTTGACTCAGAAACTTGACCCAGGACTGAAAAGTAGCTGAAGTAAAAATTTGTAGTGGCTCAGCT
CACAGTAGAAAGCATATCCAGAAAGAAGAAGAAGAAGAAGGAGAAGGAGAAGGAGAAGGAGAAGGAGA
AGGAGAAGAAGAAGGAGGAGGAGGAGAAGAAGAAGAAGAAGGAGGAAGAAGAAGAAGAAGAAGGAGAG
AAGAAGGAAGAAGAAGAAGATGAAGAAGAAGAAGAAGAAGAAGAAGAAGAAGAAGAAGAAGAAGAAGAAG
AAGAAGAAGAAGAAGAAGAAGAAGAAGAAGAAGAAAAGTGCCCACT**GAAGCACACTGAAGCTCCC
T**   (SEQ ID NO: 63)

AGGGAGCTTCAGTGTGCTTCAGTGGGCACTTTTCTTCTTCTTCTTCTTCTTCTTCTTCTTCTTCT
TCTTCTTCTTCTTCTTCTTCTTCTTCTTCTTCTTCTTCTTTCTTCATCTTCTTCTTCCTTCT
TCTCTCCTTCTTCTTCTTCTTCCTCCTTCTTCTTCTTCTTCTCCTCCTCCTCCTTCTTCTTC
TCCTTCTCCTTCTCCTTCTCCTTCTCCTTCTTCTTCTTCTTTCTGGATATGCTTTCTAC
TGTGAGCTGAGCCACTACAAATTTTTACTTCAGCTACTTTTCAGTCCTGG**GTCAAGTTTCTGAGTCAA
GCCA**    (SEQ ID NO: 64)

TGGCTTGACTCAGAAACTTGACCCAGGACTGAAAAGTAGCTGAAGTAAAAATTTATAGTGGCTCAGCT
CACAGTAGAAAGCATATCCAGAAAAAAGAAGAAGAAGAAGAAGAAGAAGCAGAAGAAGAAGAAGA
AGAAGAAGAAGAAGAAGAAGAAGAAGAAGAAGAAGAAGAAGAAGAAGAAGAGGAAGAGGAAGAAG
AAGAAGAAGAAGAAGAAGAAGAAGAAGAAGAAGAAGAAGAAGAAGAAGAAGAAGAAGAAAAGTGC
TCACTGAAGCACACTGAAGCTCCCT     (SEQ ID NO: 65)

AGGGAGCTTCAGTGTGCTTCAGTGAGCACTTTTCTTCTTCTTCTTCTTCTTCTTCTTCTTCTTCT
TCTTCTTCTTCTTCTTCTTCTTCCTCTTCCTCTTCTTCTTCTTCTTCTTCTTCTTCTTCTTC
TTCTTCTTCTTCTTCTTCTTCTTCTTCTTCTTCTTCTTCTGCTTCTTCTTCTTCTTCTTCTT
CTTTTTTCTGGATATGCTTTCTACTGTGAGCTGAGCCACTATAAATTTTTACTTCAGCTACTTTTCAG
TCCTGGGTCAAGTTTCTGAGTCAAGCCA     (SEQ ID NO: 66)

DYF1001 (multi-copy marker)
chrY:23054609-23055044
chrY:24688349-24688790
chrY:24981317-24981750

GCCTGGGCAACAAAAGTGACACTCTGTCTCAAGAAAGAAGGAAGGAAGGAAGGAAGGAAGGAAG
GAAGGAGAGAAAGAAAGAAAGACAAAGAAAGAAAGAAAGAAAGAAAGAAAGAAAGAAAGAAAGAAAGA
AAGAAAGAAAGAGAAAGAGAGAAAGAAAGAAAGAAAGAGAAAGAGAGAGAGAAAGAGAGAAAAT
GAAAGAAAAGAAGGAAGGAAGGAAGGAAGAAAGAAAGAAAGAAAGAAAGAAAGAAAGAAAGAAGAA
AGAAAGAAAGAAAGAAAGAAAGAAAGAAAGAAGGAAGGAAGGAAAGAGAAAGAAAGAAAGGA
AGGAAGGAAGGAAGGAAGGAAGGAAGGAAGGAAGGAAGGAAGGAAGGAAGCACTGTAACC
ATCTTTTGTAGAACAGGTCTGCTGTGC     (SEQ ID NO: 67)

Figure 4 (continued)

GCCTGGGCAACAAAAGTGACACTCTGTCTCAAGAAAGAAGGAAGGAAGGAAGGAAGGAAGGAAGGAAG
GAAGGAAGGAAGGAAGGAGAGAAAGAAAGAAAGACAAAGAAAGAAAGAAAGAAAGAAAGAAAGAAAGAAAGA
AAGAAAGAAAGAAAGAAAGAAAGAAAGAAAGAGAGAAAGAAAGAAAGAAAGAGAAAGAGAGAGAGAAA
GAGAGAAAATGAAAGAAAAAGAAGGAAGGAAGGAAGGAAGGAAGGAAGAAAGAAAGAAAGAAAGAAAG
AAAGAAAGAAAGAAAGAAAGAAAGAAATAAAAGAAAAGAAAGAAAGAAAGAAGGAAGGAAGGAAAGAG
AAAGAAAGAAAGGAAGAAAGGAAGGAAGGAAGGAAGGAAGGAAGGAAGGAAGGAAGGAAGGAAGCACT
GTAACCATCTTTTGTAGAACAGGTCTGCTGTGC   (SEQ ID NO: 68)

GCACAGCAGACCTGTTCTACAAAAGATGGTTACAGTGCTTCCTTCCTTCCTTCCTTCCTTCCTTCCTT
CCTTCCTTCCTTTCTTCCTTTCTTTCTTTCTCTTTCCTTCCTTCCTTCTTTCTTTCTTTCTTTTCTTT
TATTTCTTTCTTTCTTTCTTTCTTTCTTTCTTTCTTTCTTTCTTTCTTTCTTTCTTTCTTCCTTCCTT
CCTTCCTTCCTTCCTTCTTTTTCTTTCATTTTCTCTCTTTCTCTCTCTCTTTCTCTTTCTTTCTTTCT
TTCTCTCTTTCTTTCTTTCTTTCTTTCTTTCTTTCTTTCTTTCTTTCTTTCTTTCTTTCTTTCTTTGT
CTTTCTTTCTTTCTCTCCTTCCTTCCTTCCTTCCTTCCTTCCTTCCTTCCTTCCTTCTTTCTTGAGAC
AGAGTGTCACTTTTGTTGCCCAGGC    (SEQ ID NO: 69)

DYR88 (multi-copy marker)
chrY:24331827-24332233
chrY:25337916-25338322

CACCTGTAATCCTAGCTACTCAGAAGGCTGAGGCAGGAGGATTGCTTGAATCCTGGAAGTGGAGGTTG
CAGTGAGCCAAGATCACACCACTGCACTCCAGCCTGAGTGACAGAGCGAGACTCCATCTCAACAAAAA
AGAAAGAAAGAAAGAAAGAAAGAAAGAAAGAAAGAAAGAAAGAAAGAAAGAAAGAAAGAAAGAAAGAA
AGAAAGATGTTTAATTGACTCTCAGTTCCACAGGCCATACAGGAAGCATGGCTTGGCAGGCCTCAGGA
AACACAATCATGGCAGAAGGTGAAGGGGAAGGAGGCATGTCTTACTTGGCTGGAGAAGGAGGAAGAGA
GCTAAAGCGGGAATGCTGTACACTTTTAAACAACCAGATCTCATGAGCACTCTATGATGAGAAAGC
   (SEQ ID NO: 89)

GCTTTCTCATCATAGAGTGCTCATGAGATCTGGTTGTTTAAAAGTGTACAGCATTCCCGCTTTAGCTC
TCTTCCTCCTTCTCCAGCCAAGTAAGACATGCCTCCTTCCCCTTCACCTTCTGCCATGATTGTGTTTC
CTGAGGCCTGCCAAGCCATGCTTCCTGTATGGCCTGTGGAACTGAGAGTCAATTAAACATCTTTCTTT
CTTTCTTTCTTTCTTTCTTTCTTTCTTTCTTTCTTTCTTTCTTTCTTTCTTTCTTTCTTTCTTTCTTT
TTTGTTGAGATGGAGTCTCGCTCTGTCACTCAGGCTGGAGTGCAGTGGTGTGATCTTGGCTCACTGCA
ACCTCCACCTCCAGGATTCAAGCAATCCTCCTGCCTCAGCCTTCTGAGTAGCTAGGATTACAGGTG
   (SEQ ID NO: 90)

DYS688 (single-copy marker)
chrY:8465358-8465755

TATTCTAGACTCTGCTCAGAGAGGTGGTGATTACATATTGCAGAGCCCAGCACCTAGGTTAAGTGACC
TTCTTCTTCTTCTTTCTTCTTCTTCTTCTTCTTCTTCTTCTTCTTCTTCTTCTTCTTCTTCTTCTTCT
TCTTCTTCTTCTTCTTCTTCTTCTTCTTCTTCTTCTCCTCCTCCTTCTCCTTCTTCTTCTCCTTC
TCCTTCTCCTTCTCCTTCTCCTACTTCTTCTTCTTCTTCTTCTTCTTCTTCTTCTTCTTCTTCTTCTT
CTTCTTCTTCTTCTTCTTCTTCTTCTTCTCCTCCTTCTTCTTTATTCTTCTGTCTTTGTTTTTGT
TTTGAGACAGAGTCTTGCACTGTTGCTCGGGCTGGAGTGAAGAGATACAATGACAGC
   (SEQ ID NO: 70)

Figure 4 (continued)

DYF1002 (multi-copy marker)
chrY:16242183-16242603
chrY:16342720-16343155

GCAAGACCATGTCTTGAAAGTAAGGGAAAGCGAGGGGTAAGTAGTGGAAGGGAGGAGGAGGAAAGGGG
GGGAGAGAGAGAGAGAGAAAGAAAGAAAGAAATAGAAAGAAAGAAAGAAAGAAAGAAAGAAAGAAAGA
AAGAAAGAAAGAAAGAAAGAGAAAGAAAGAAAGAAAGGAAAGAAAGAAAGAAAGAAAGAAAGAAAGAA
AGAAAGAAAGAAAGAAACAGAGAAAGAAAGAAAGAAAGAGAAAGAAAGAAAGAAAGAAAGAAAG
AAAGAAAGAAAGAAAAAGAAAAGAAAGAGGAAGAAAGAAAGAAAGAAAAAGAGAAAGAAAGGAGGGAG
GGAGGGAAGGAAAGAAGGAAGGAGAGATGTGATGTTACTTTAGAGCTTTGAATATATAAAAGCAAATA
ATGAGGACTTGC (SEQ ID NO: 71)

GCAAGTCCTCATTATTTGCTTTTATATATTCAAAGCTCTAAAGTAACATCACATCTCTCCTTCCTTCT
TTCCTTCCCTCCCTCCCTCCTTTCTTTCTCTTTTTCTTTCTTTCTTTCTTCCTCTTTCTTTTCTTTTT
CTTTCTTTCTTTCTTTCTTTCTTTCTTTCTTTCTTTCTTTCTTTCTTTCTCTTTCTTTCTTTCTTTCT
CTGTTTCTTTCTTCTTTCTTTCTTTCTTTCTTTCTTTCTTTCTTTCTTTCTTTCCTTTCTTTCTTTCT
TTCTTTCCCTTTCTTTCTTTCTTTCTTTCTTTCTTTCTTTCTTTCTTTCTTTCTTTCTTTCTATTTCT
TTCTTTCTTTCTCTCTCTCTCTCCCCCCCTTTCCTCCTCCTCCCTTCCACTACTTACCCCTCGCTT
TCCCTTACTTTCAAGACATGGTCTTGC (SEQ ID NO: 72)

DYF1003 (single-copy marker)
chrY:15084614-15085009

GTGAGACTCCATCTCAAAAGAAGAAAGAAGGAAAGAAAGAAAGAAAGGAACGAAGGAAGGAAGGAAGG
AAGGAAGGAAGGAAGGAAGGAAGGAAGGAAGGAAGAAAGAAAGAGAAAGAAAGAAAAAGAGGGAGGGAGGG
AAGGAGGAAGGAAGGAAAGAGAGAGAGAGGGAGAGAGAACGGAAGAAAGAAAGAAAGAAAGAAAGAAA
GAAAGAAAGAAAGAAAGAAAGAAAGAAAGAAAGAAAGAAAGAAAGAAAGGTAGAAAGAAAGAAAGAAA
GAAAGAAAGAAAGAAAGAAAGAAAGAAAGAAAGAAAGAAAGAGAAAGAAAGAAAGAAAGAAAAAGAAA
GAAAGAAAAGAAAGGAAAGTTTTGCCAGGAGAAGCTGTCCTTCACACACCAGAT (SEQ ID NO: 73)

DYS1007 (single-copy marker)
chrY:17299905-17300373

GCACATGTCTATAGTCCCATCTACCCAGGAGGATGAGGCAGGAGGATTGCTTGAGCCAGGGGTAAGAT
AATATGGCACCGTGGCTCTCCAGCCTGGGTAACATGGTGAGACCCTGTCTGAAAGAAAAGAAAAGAAA
GAAAGAAAGAAAGAAAGAAAGAAAGAAAGAAAGAAAGAAAGAAAGAAAGAGAAAGAAAGAAAGAGAAA
GAAAGAAAGAAAGAGAAAGAAAGAAAGAAAGAAAGAAAGAAAGAAAGAAAGAAAGAAAGAAAGAAAGA
AAGAAAGGGAAAGGGAGAAAGAGAGAGAGACAGCAAGAGAAAGAGAGAGAGATAAGGAGGGAAGGAGG
GAGGGAGGATGGGATGAAAGAAGGAAAGAAGGGAAGAAGGGAAGAAAAGGAGGTGGTGAGGGAGATTA
AGAGATGACAGATGAGTGTGGCCACAGTTTGGCTGAAATTCTCAAGAATTACTCAGTGGC (SEQ ID
NO: 74)

Figure 4 (continued)

DYS1010 (single-copy marker)

chrY:17324747-17325139

AGAATCTATGATCACAGCACTTTTCTGAATCCTGGACAAGTGAGAAAAGAAAGAAAGAAAGAAAGAAA
GAAAGAAAGAAAGAAAGAAAGAAAGAAAGAAAGAAAGAAAGAAAGAGAGAGAGAGAGAGAGAGAGAGA
GAGAAAGAAAGAAAGAAAGAAAGAAAGAAAGAAAGAAAGAAAGAAAGAAAAAAGAGAGGGAGGGAGAG
AGTATGAGGAAGGGAGGGAGGGAGTATGAGGAAGGGAGGGAGGGAGCAAGGAAGGAAGGAGAAAGGAG
GGAGGAAAGGAAGGAGGGAGGGAGGAGGGAAGGAAGGAAGAAAGGGAGGAAGGGAGGAAGGAAGGAAA
AGAAGAAGGAAGAAAGAAAAGAAAAGGACAGAAAGAAAATGAGGTAGAAAG (SEQ ID NO: 75)

DYS1012 (single-copy marker)

chrY:56858298-56858581

GCAAGACTCCATCTCCAAAAAGAAAGAAAGAAAGAAAGAAAGAAAGAAAGAAAGAAAGAAAGAAAGAA
AGAAAGAAAGGAAAGAAAAGAAAGAAAAGAAAGAAAGAAAAGAAAGAAAGAAAGAAAGAAAAGAAAGA
AAGAAGGAAAGAAGGAAAGAAGGAAAGAAGGAAGGAAAGAAAGAAAGAAAGAAAGAAAGAAAGAAAGA
AAGAAAGAAAGAAAGAAAGAAAGAAAGAAAGAAAGAAAGTTAGTTAATAATGGCATTAC**TCATAATGG
ACCCAAGCTTG** (SEQ ID NO: 76)

DYS685 (single-copy marker)

chrY:7963956-7964261

GGGCTTTATAAGTTATCTGAGGCTGTTATAATCTTTAAACTTTTTTTTACCAGAAATAGATTTATTCA
CGCTTGTCTTTCTTTCTTTCTTTCTTTCTTTCTTTCTTTCTTTCTTTCTTTCTTTCTTTCTTTCTTTC
TTTCTTTCTTTCTCTTTCTTTCTGTCTTTTTTCTTTCTCTTTCTTTCTTTCTTTCTTTCTTTCTTTCT
TTCTTTCTTTCTTTTTCTTTCTTTCTTTCTTCCTTCTTTCTCTTTTCTTTTTTATTATT
TATTTATTTATTTTTAAGATGGAGTCTGTCACC (SEQ ID NO: 77)

DYS712 (single-copy marker)

chrY:13446462-13446882

GTGGCTCACTCCTATAACCTAGTTTGGAAGGTCAAGGAGGGTGGATTGCTTGAGCCCAGAAGTTCAAG
AACAGCCTGGGTAACAGTGTGAGATAGATAGATAGATAGATAGATAGATAGATAGATAGATAGATAGA
TAGATAGATAGATAGATAGACAGACAGACAGACAGACAGGATGTCATTTGTTTATATCATTTAA
TTATAAGTGTTCATGGGCTGTACCATATAATACTGTTAAGATGACACTACTCTTAAATTTGAACTGCA
TATCATAATCCCTGGTGGCTTTTGGCGCAAACACAAAACTGATCCTGTGGAAAATACAAGGTACCTAG
AGGAGCCAAAATAACTTTGCAAAAAAGGAACCAAGGTGAAAAAAATCATACTAA**CCAGTCTCAAAACT
TACTACAAAGTT** (SEQ ID NO: 78)

<u>Empirically verified fast mutating (FM) Y-STR markers (mutation rates 5x10<sup></sup></u>
<u>$^{3}$>$\mu$<10$^{2}$)</u>

DYS1009 (multi-copy marker)

chrY:17642914-17643292 chrY:18262718-18263092

Figure 4 (continued)

TCCCAGAGTCTCAGAGTGCTGGAATGATGGGCATGAGCCACTTTGCCTGGCCTCCTGGTAATCACTCA
CAACCACGACATGTGTTCTGATTTTTTTTCTTTCTTTTCTTTTCTTTCTCTCTCTTTCTTTCTTTCCT
TCCTTCCTTCCTTCCTTCCTTCCTTCCTTCCTTCCTTCCTTCCTTCCTTCCTTCATTTCTTCCT
CTCTTTCTTTCTTTCTTTCTTTCTTTCTTCTCTTTCTTCTTTTTTGATGGAGTCTTGCTCTGTGTGA
GGCGAGGAGCATCACCTTGGAAGCCACAGCACCGCATTACAAAGCCCCATTCACATGCACAAAGCTTT
ATTCCCTTCCTGAATTCCTAGCTGGTGACTTCTATGGC   (SEQ ID NO: 79)

GCCATAGAAGTCACCAGCTAGGAATTCAGGAAGGGAATAAAGCTTTGTGCATGTGAATGGGGCTTTGT
AATGCGGTGCTGTGGCTTCCAAGGTGATGCTCCTCGCCTCACACAGAGCAAGACTCCATCAAAAAAAG
AAGAAAGAGAAGAAAGAAAGAAAGAAAGAAAGAAAGAGAGGAAGAAATGAAGGAAGGAAGGAAGGAAG
GAAGGAAGGAAGGAAGGAAGGAAGGAAGGAAGGAAGGAAAGAAAGAAAGAGAGAGAAAGAAAAGAAAA
GAAAGAAAAAAATCAGAACACATGTCGTGGTTGTGAGTGATTACCAGGAGGCCAGGCAAAGTGGCTC
ATGCCCATCATTCCAGCACTCTGAGACTCTGGGA    (SEQ ID NO: 80)

DYS1013 (single-copy marker)

chrY:14697144-14697687

TTATCTTGCTGACCATTAGAGAAGATGGGGTCACTAACAGATAGATAGATAGGTAGGTAGGCAGATAG
ATAGATAGATAGATAGATAGATAGATAGATAGATTGATAGATAATAGATGTGAATCGATAGATG
GAAATGGATGGATAGTAAGATGATAGCTAGGTGATATATGTATATATAGACAGATAGATAGAAAGATA
GATAGATAGATAGATGATAGAGATGGATAGATATAGATACATAGATAAATGATAGCTCATAATG
GATAGATATAGGTAGATAGAGGTGGAGAGATAAAAGACAGAAAGTAAGACATATAGATATAGATAAGC
AGATAGGTGATAGATAGATAGATAGATAGATAGATAGATAGATAGATAGATAGAAGGTAGAGATAGAA
ACAGGTAGACAGGTATATAGATGATGGGTATATAGATGAGAGAGATAGATAGATAGATAGATAGATAG
ATAGATAGATAGATAGGCAGGCAGGCAGACAGAGAGACAGATACATAGGCAGGTAGGTAGGTAGAGG
 (SEQ ID NO: 81)

DYS1014 (single-copy marker)

chrY:3772704-3773174

ACCTTCTGGCGAAGTAACCCAAACGTTTACTTTCTTTCTCTTTTTCTCTTTTTTTCTTTATTTTTCTT
TCTCTGTTCTTTTTCTCTCCTTCCTTCCTTCCTTCCTTCCTTCCTTCCTTCCTTCCTTCCTTCCTTCT
TTCCCTCCTTCTTTCTCTTTACCTTCTGGTGAACTGACTCGAACCTTTACTTACTTTCTTTCTATTTT
TCTCTATTTTTTCTCTTTCTTCCTGTCCTTTCCTTTCTTTTCCTTTCCTTTCCTTTCCTTTCCTTTCC
TTTCCTTTCCTTTCCTTTCCTTTCCTCTCTTTCTCTTTCTCTCTTTCTCTTCCTTCCCTTCCCTTCCC
TTTCCTCTCTTTCTTTCTTTCTTTCTTTCTTTCTTTCTTTCTTTCTTTCTTTCTTTCTTTTTCTTTCT
TTCTTTTTCTTTCTTTCTACAGGGTCTCACTCTGTCACCCAAGCTAGAGTGCAGTGCTGAGA
 (SEQ ID NO: 82)

Figure 4 (continued)
DYS1016 (single-copy marker)

chrY:12092576-12093208

GAGTGAAACCATCTCTAAGACATAAAGAAAGAACTAAAAGAGAAAAGAAAAGAAGGAAGGCAGGAAGG
AAGGAAGAAAGGAAGGAAGGAAGGAGTGAGGGAGGGAGGGAGGGAGGGAAAAAAGAAAGAAGGGAGAG
AGAGGGAGAAAGAGAAGGAAGGAGAGTAGGAAAAAGGAAGGAAGGAATGAAGAGAGGAAAGAAGAGAA
AGAAGAAAGAATGAAGGAAGATAAAAAGACAGAAAGAAGGGAGAGAGGGAGGGAGGGAAGGAAAGTAC
AAAAAAGAAGGAAGAAGAAGGAAGGAAGGAAAAAAGAGAAAAAGAAAGACAGAAAGAAAGAGA
GAAAGAAAGGAGAGAGGAAGGAAGGAAGGAAGGAAGGAAGGAAGACAGAGAAAAAAGAAAGAAACAA
ACAAACAAAGAGAAAGAAAAAGAGAGAAAGAAAGAGAGAAAGAAAGAAAGGAAAAGAAAGAAAGAGA
GAAAGAAAGAAAGAAAGAAAGAAAGAAAGAAAGAAAGAAAGAAAGAAAGAAAGAGAAAGAAAGAAGGA
AGGAAAGGAAGGAAGGAAGGAAAGGAAGGAAGGAAGGAAAGAAAGAAAGAGGGGGAATAGAGAAGTCC
ATCATGGTGTGTTTGCAAGC (SEQ ID NO: 83)

DYS1017 (single-copy marker)

chrY:5541615-5541844

ATAGGACAGGTGGTTGAATGGCTAGCACTCCATGAGCTTTATTCATGTATATTTATAAAAGTGCAATT
TCTTTTTCTTTCTTTCTTTCTTTCTTTCTTTCTTTCTTTCTTTCTTTCTTTCTTTCTTTCTTTCTTTC
TTTCTTTCTATATTATAGCAAACTCTTGTACATTTACTTACTTATTTTCTTTCAGTGATCATGCTAGT
ATGGTTGTACTATCTGAAAATCTAG (SEQ ID NO: 84)

DYS1005 (single-copy marker)

chrY:7849377-7849841

CTATAGTTCCTAGAGCAAAGAGTGAGCTGCCATTTTTTCCTGTTTGTGTGACTAAGCTGTTCCTGCCT
CCTGGCTTTGGAGGATCCAAATAAACTGTGGATGGAAGTGGTACCTCTGCAAAGCAGAGCTGTTCTAC
AAAAATGTGGCTAGACTTTCCTTTCCTTTCCTTTCCTTTCCTTTCCTTTCCTTTCCTTTCCTTTCCTT
TCCTTTCCTTCCCTCCCTCCCTCCCTCCCTCCCTCCCTCCCTTCTTTCTCTTTCTTTCTTTCTTTCCT
TCCTTCCTTCCTTCCTTCCTTCCTTCCTTCCTTCCTTCCTTCCTTCTTTCTTTCTTTCTTTCTT
TCTTTCTTTCTTTCTTTCTTTCTTTCTTCCTTCCTTCCTTCCTTCTTTCTTTCGAGACAGAGTA
TTCCCCCTGTTGCCCAGGCTGGAGTGCACTGGGGCAATCTCAGATTACCACAACCT (SEQ ID NO: 85)

DYF1004 (multi-copy marker)

chrY:18466997-18467397
chrY:18852999-18853399

Figure 4 (continued)

GCAAAGCAGAATATTTATGTTTCAGTGTACTTTATTCATCCGTTGCGGGTTCAGGGGTCTGCAAGGGA
CAGACCCCCAAAGTTGGTGCCACAGCATGAGAAGTGTGAGAAGTGTTACCACAGTTTCTCCTTCCTTC
CTTCCTTCCTTCCTTCCTTCCTTCCTTCCTTCCTTCCTTCCTTCCTTCCTTCCTTCCTCCCTCCCTCC
CTCCCTCTCTCTCTCTCTCTCTTTATTTCCTTGGTGGGGAGTAAAATGGCACCTAGCTAGGTCACCCA
GGCTGGAGTGCAGTCACATGATCTCAGCTCACTGCAAATATCCCCTCCCAGGTTCAAGTGATTATCTT
GCCTCAGCCTCTAGCATAGCTGGGATAAAAGGCACTTGCCACCACACCTCGCAAATTTTT
(SEQ ID NO: 86)

GCAAAGCAGAATATTTATGTTTCAGTGTACTTTATTCATCCGTTGCGGGTTCAGGGGTCTGCAAGGGA
CAGACCCCCAAAGTTGGTGCCACAGCATGAGAAGTGTGAGAAGTGTTACCACAGTTTCTCCTTCCTTC
CTTCCTTCCTTCCTTCCTTCCTTCCTTCCTTCCTTCCTTCCTTCCTTCCTTCCTTCCTCCCTCCCTCC
CTCCCTCTCTCTCTCTCTCTCTTTATTTCCTTGGTGGGGAGTAAAATGGCACCTAGCTAGGTCACCCA
GGCTGGAGTGCAGTCACATGATCTCAGCTCACTGCAAATATCCCCTCCCAGGTTCAAGTGATTATCTT
GCCTCAGCCTCTAGCATAGCTGGGATAAAAGGCACTTGCCACCACACCTCGCAAATTTTT
(SEQ ID NO: 87)

DYS1006 (single-copy marker)

chrY:13208544-13208915

CAAGACCAGCATATCAGTTGAGGCCAGGAGTTTGAGACCAGCCTGGCCTACATAGTGGAACCTCATCT
CTACTAAAAATAGAAAAGAAAGAAGAAGAAGAAGAAGAAGAAGAAGAGGAAGAAGAGGAAGAAGAAGA
AGGGGGAGAAGAAGGGGGAGAAGAAGGGGGAGAAGAAGGGGGAGAAGAAGGGGGAGAAGAAGAAGAAG
AAGAGGAAGAGGAAGAGGAAGAGGAAGAAGAAGAAGAAGAAGAAGAAGAAGAAGAAGAAGAAGAAGAA
GAAGAAGAAGAAGAAGAAGAGAGCCAGGAAAGGAGCCAGGTGTGGTGGCATGCACCTGTAGTCCC
AGCTGAGCAGGAGTAGGAGGTTGCAGTGAGCC
(SEQ ID NO: 88)

SEQUENCE LISTING

<160> NUMBER OF SEQ ID NOS: 150

<210> SEQ ID NO 1
<211> LENGTH: 20
<212> TYPE: DNA
<213> ORGANISM: Homo sapiens

<400> SEQUENCE: 1
aaagaaagaa agaaagaaag                                          20

<210> SEQ ID NO 2
<211> LENGTH: 20
<212> TYPE: DNA
<213> ORGANISM: Homo sapiens

-continued

```
<400> SEQUENCE: 2
aagaaagaaa gaaagaaaga                                      20

<210> SEQ ID NO 3
<211> LENGTH: 20
<212> TYPE: DNA
<213> ORGANISM: Homo sapiens

<400> SEQUENCE: 3
agaaagaaag aaagaaagaa                                      20

<210> SEQ ID NO 4
<211> LENGTH: 20
<212> TYPE: DNA
<213> ORGANISM: Homo sapiens

<400> SEQUENCE: 4
gaaagaaaga aagaaagaaa                                      20

<210> SEQ ID NO 5
<211> LENGTH: 20
<212> TYPE: DNA
<213> ORGANISM: Homo sapiens

<400> SEQUENCE: 5
tttctttctt tctttctttc                                      20

<210> SEQ ID NO 6
<211> LENGTH: 20
<212> TYPE: DNA
<213> ORGANISM: Homo sapiens

<400> SEQUENCE: 6
ttctttcttt ctttctttct                                      20

<210> SEQ ID NO 7
<211> LENGTH: 20
<212> TYPE: DNA
<213> ORGANISM: Homo sapiens

<400> SEQUENCE: 7
tctttctttc tttctttctt                                      20

<210> SEQ ID NO 8
<211> LENGTH: 20
<212> TYPE: DNA
<213> ORGANISM: Homo sapiens

<400> SEQUENCE: 8
ctttctttct ttctttcttt                                      20

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
gcctgggcaa caaaagtg                                        18

<210> SEQ ID NO 10
<211> LENGTH: 22
```

```
<212> TYPE: DNA
<213> ORGANISM: Artificial Sequence
<220> FEATURE:
<223> OTHER INFORMATION: primer

<400> SEQUENCE: 10
gcacagcaga cctgttctac aa                                          22

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
agggagcttc agtgtgcttc                                            20

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
tggcttgact cagaaacttg ac                                         22

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
cacctgtaat cctagctact caga                                       24

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
gctttctcat catagagtgc tcatg                                      25

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
gtggctcact cctataacc                                             19

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16
```

-continued

```
aactttgtag taagttttga gactgg                                    26

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17
tattctagac tctgctcaga gaggtg                                    26

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
gctgtcattg tatctcttca ctcc                                      24

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
gcaagactcc atctccaaaa ag                                        22

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
caagcttggg tccattatga                                           20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gcaagaccat gtcttgaaag                                           20

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
gcaagtcctc attatttgc                                            19

<210> SEQ ID NO 23
<211> LENGTH: 25
<212> TYPE: DNA
<213> ORGANISM: Artificial Sequence
```

-continued

```
<220> FEATURE:
<223> OTHER INFORMATION: primer

<400> SEQUENCE: 23
gcacatgtct atagtcccat ctacc                                      25

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
gccactgagt aattcttgag aattt                                      25

<210> SEQ ID NO 25
<211> LENGTH: 26
<212> TYPE: DNA
<213> ORGANISM: Artificial Sequence
<220> FEATURE:
<223> OTHER INFORMATION: primer

<400> SEQUENCE: 25
agaatctatg atcacagcac ttttct                                     26

<210> SEQ ID NO 26
<211> LENGTH: 26
<212> TYPE: DNA
<213> ORGANISM: Artificial Sequence
<220> FEATURE:
<223> OTHER INFORMATION: primer

<400> SEQUENCE: 26
ctttctacct cattttcttt ctgtcc                                     26

<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
gggctttata agttatctga ggc                                        23

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
ggtgacagac tccatcttaa                                            20

<210> SEQ ID NO 29
<211> LENGTH: 23
<212> TYPE: DNA
<213> ORGANISM: Artificial Sequence
<220> FEATURE:
<223> OTHER INFORMATION: primer

<400> SEQUENCE: 29
gtgagactcc atctcaaaag aag                                        23
```

-continued

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
atctggtgtg tgaaggacag c                                         21

<210> SEQ ID NO 31
<211> LENGTH: 26
<212> TYPE: DNA
<213> ORGANISM: Artificial Sequence
<220> FEATURE:
<223> OTHER INFORMATION: primer

<400> SEQUENCE: 31
ttatcttgct gaccattaga gaagat                                    26

<210> SEQ ID NO 32
<211> LENGTH: 26
<212> TYPE: DNA
<213> ORGANISM: Artificial Sequence
<220> FEATURE:
<223> OTHER INFORMATION: primer

<400> SEQUENCE: 32
cctctaccta cctacctgcc tatgta                                    26

<210> SEQ ID NO 33
<211> LENGTH: 27
<212> TYPE: DNA
<213> ORGANISM: Artificial Sequence
<220> FEATURE:
<223> OTHER INFORMATION: primer

<400> SEQUENCE: 33
ctatagttcc tagagcaaag agtgagc                                   27

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
aggttgtggt aatctgagat tgc                                       23

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
gagtgaaacc atctctaaga c                                         21

<210> SEQ ID NO 36
<211> LENGTH: 19
<212> TYPE: DNA
<213> ORGANISM: Artificial Sequence
<220> FEATURE:
<223> OTHER INFORMATION: primer -continued

<400> SEQUENCE: 36
gcttgcaaac acaccatga                                                    19

<210> SEQ ID NO 37
<211> LENGTH: 20
<212> TYPE: DNA
<213> ORGANISM: Artificial Sequence
<220> FEATURE:
<223> OTHER INFORMATION: t2_15f

<400> SEQUENCE: 37
ataggacagg tggttgaatg                                                   20

<210> SEQ ID NO 38
<211> LENGTH: 23
<212> TYPE: DNA
<213> ORGANISM: Artificial Sequence
<220> FEATURE:
<223> OTHER INFORMATION: primer

<400> SEQUENCE: 38
ctagattttc agatagtaca acc                                               23

<210> SEQ ID NO 39
<211> LENGTH: 21
<212> TYPE: DNA
<213> ORGANISM: Artificial Sequence
<220> FEATURE:
<223> OTHER INFORMATION: primer

<400> SEQUENCE: 39
tcccagagtc tcagagtgct g                                                 21

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
gccatagaag tcaccagcta gg                                                22

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
accttctggc gaagtaaccc                                                   20

<210> SEQ ID NO 42
<211> LENGTH: 21
<212> TYPE: DNA
<213> ORGANISM: Artificial Sequence
<220> FEATURE:
<223> OTHER INFORMATION: primer

<400> SEQUENCE: 42
tctcagcact gcactctagc t                                                 21

<210> SEQ ID NO 43

-continued

```
<211> LENGTH: 19
<212> TYPE: DNA
<213> ORGANISM: Artificial Sequence
<220> FEATURE:
<223> OTHER INFORMATION: primer

<400> SEQUENCE: 43
actgaacgct agcctgggt                                                    19

<210> SEQ ID NO 44
<211> LENGTH: 27
<212> TYPE: DNA
<213> ORGANISM: Artificial Sequence
<220> FEATURE:
<223> OTHER INFORMATION: primer

<400> SEQUENCE: 44
acccatatag ctatccatct gtctaat                                           27

<210> SEQ ID NO 45
<211> LENGTH: 22
<212> TYPE: DNA
<213> ORGANISM: Artificial Sequence
<220> FEATURE:
<223> OTHER INFORMATION: primer

<400> SEQUENCE: 45
accgaagctg ttcctattag gc                                                22

<210> SEQ ID NO 46
<211> LENGTH: 27
<212> TYPE: DNA
<213> ORGANISM: Artificial Sequence
<220> FEATURE:
<223> OTHER INFORMATION: primer

<400> SEQUENCE: 46
ctgtcaaaga tgtaatgggt atggtac                                           27

<210> SEQ ID NO 47
<211> LENGTH: 26
<212> TYPE: DNA
<213> ORGANISM: Artificial Sequence
<220> FEATURE:
<223> OTHER INFORMATION: primer

<400> SEQUENCE: 47
gcaaagcaga atatttatgt ttcagt                                            26

<210> SEQ ID NO 48
<211> LENGTH: 19
<212> TYPE: DNA
<213> ORGANISM: Artificial Sequence
<220> FEATURE:
<223> OTHER INFORMATION: primer

<400> SEQUENCE: 48
aaaaatttgc gaggtgtgg                                                    19

<210> SEQ ID NO 49
<211> LENGTH: 23
<212> TYPE: DNA
<213> ORGANISM: Artificial Sequence
<220> FEATURE:
<223> OTHER INFORMATION: primer

<400> SEQUENCE: 49
```

```
caagaccagc atatcagttg agg                                      23

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
ggctcactgc aacctcctac                                          20

<210> SEQ ID NO 51
<211> LENGTH: 25
<212> TYPE: DNA
<213> ORGANISM: Artificial Sequence
<220> FEATURE:
<223> OTHER INFORMATION: primer

<400> SEQUENCE: 51
gcatatcatc tatcacctat attat                                    25

<210> SEQ ID NO 52
<211> LENGTH: 24
<212> TYPE: DNA
<213> ORGANISM: Artificial Sequence
<220> FEATURE:
<223> OTHER INFORMATION: primer

<400> SEQUENCE: 52
ataaatagaa gataggtaga taac                                     24

<210> SEQ ID NO 53
<211> LENGTH: 24
<212> TYPE: DNA
<213> ORGANISM: Artificial Sequence
<220> FEATURE:
<223> OTHER INFORMATION: primer

<400> SEQUENCE: 53
gcctgagtaa cactgcaaga ttct                                     24

<210> SEQ ID NO 54
<211> LENGTH: 24
<212> TYPE: DNA
<213> ORGANISM: Artificial Sequence
<220> FEATURE:
<223> OTHER INFORMATION: primer

<400> SEQUENCE: 54
agagacaatt ttctatgctc cagc                                     24

<210> SEQ ID NO 55
<211> LENGTH: 23
<212> TYPE: DNA
<213> ORGANISM: Artificial Sequence
<220> FEATURE:
<223> OTHER INFORMATION: primer

<400> SEQUENCE: 55
tccaatcagg aacattttaa agc                                      23

<210> SEQ ID NO 56
<211> LENGTH: 26
<212> TYPE: DNA
```

-continued

```
<213> ORGANISM: Artificial Sequence
<220> FEATURE:
<223> OTHER INFORMATION: primer

<400> SEQUENCE: 56
taagttatct ttagcttttt gctggc                                          26

<210> SEQ ID NO 57
<211> LENGTH: 19
<212> TYPE: DNA
<213> ORGANISM: Artificial Sequence
<220> FEATURE:
<223> OTHER INFORMATION: primer

<400> SEQUENCE: 57
gccaagatca caaccattg                                                  19

<210> SEQ ID NO 58
<211> LENGTH: 27
<212> TYPE: DNA
<213> ORGANISM: Artificial Sequence
<220> FEATURE:
<223> OTHER INFORMATION: primer

<400> SEQUENCE: 58
tgtatgagca atgctaagtt aaaacaa                                         27

<210> SEQ ID NO 59
<211> LENGTH: 25
<212> TYPE: DNA
<213> ORGANISM: Artificial Sequence
<220> FEATURE:
<223> OTHER INFORMATION: primer

<400> SEQUENCE: 59
acatgatagg aaatatgatt ctggg                                           25

<210> SEQ ID NO 60
<211> LENGTH: 24
<212> TYPE: DNA
<213> ORGANISM: Artificial Sequence
<220> FEATURE:
<223> OTHER INFORMATION: primer

<400> SEQUENCE: 60
aattagttgg aagtgtgtga ccct                                            24

<210> SEQ ID NO 61
<211> LENGTH: 337
<212> TYPE: DNA
<213> ORGANISM: Homo sapiens

<400> SEQUENCE: 61
ctaggtgaca gcgcaggatt ccatctaaaa acaaaaatca aagagagaca cagggagaaa     60
gaaagaaagg aaaaaagaaa gaaagagaga gagagaaaga aagaaagaaa gaaagaaaga     120
aagaaagaaa gaaagaaaga aagaaagaaa gaaagaaaga aagaaagaaa aagagaaaga     180
gagagggagg gaggagggag ggaggaagta aagaaggtaa gaaggaagga tggaagtaag     240
gaaggaaaga aggaaggaag gaacgaagga gagaatgaaa ggcataaaac caaagggaaa     300
tgaataaaaa taaaaacttg ccatttgctc attatcc                             337

<210> SEQ ID NO 62
<211> LENGTH: 406
```

-continued

```
<212> TYPE: DNA
<213> ORGANISM: Homo sapiens

<400> SEQUENCE: 62
tcagcaaaca ccttagctaa tcatgattct ttaccttctg gtgaactgat ccaaaccttt         60
acttattttc ttcctttttt cctctctcct tccctccctc cctctttctt cctttctttc        120
ttcctttctt tctttctttc tttctttctt tcttttctttc tttctttctt tctttccttc       180
cttccttcct tccttccttc cttccttcct tctttccttc tttccttcat ttcttctttc        240
tttctcttta ccttctggga aactgatcca aacctttact tactttctat ttttctctat        300 ttttcttttct ctattttttt ctctccttcc ttccttcctt ccttccttcc ttccttcctt       360
ccttccttcc ttccttcctt ctctttacct tctggcgaag taaccc                       406

<210> SEQ ID NO 63
<211> LENGTH: 341
<212> TYPE: DNA
<213> ORGANISM: Homo sapiens

<400> SEQUENCE: 63
tggcttgact cagaaacttg acccaggact gaaaagtagc tgaagtaaaa atttgtagtg         60
gctcagctca cagtagaaag catatccaga aagaagaaga agaagaagga gaaggagaag        120
gagaaggaga aggagaagga gaagaagaag gaggaggagg agaagaagaa gaagaaggag        180
gaagaagaag aagaagaagg agagaagaag gaagaagaag aagatgaaga agaagaaga        240 agaagaagaa gaagaagaag aagaagaaga agagaagaa gaagaagaag aagaagaaga        300
agaagaagaa aagtgcccac tgaagcacac tgaagctccc t                            341

<210> SEQ ID NO 64
<211> LENGTH: 344
<212> TYPE: DNA
<213> ORGANISM: Homo sapiens

<400> SEQUENCE: 64
agggagcttc agtgtgcttc agtgggcact tttcttcttc ttcttcttct tcttcttctt        60
cttcttcttc ttcttcttct tcttcttctt cttcttcttc ttcttcttct ttcttcatct        120
tcttcttctt ccttcttctc tccttcttct tcttcttctt cctccttctt cttcttcttc        180
ttctcctcct cctccttctt cttctccttc tccttctcct tctccttctc cttctccttc        240
ttcttcttct tctttctgga tatgctttct actgtgagct gagccactac aaattttac        300 ttcagctact tttcagtcct gggtcaagtt tctgagtcaa gcca                        344

<210> SEQ ID NO 65
<211> LENGTH: 297
<212> TYPE: DNA
<213> ORGANISM: Homo sapiens

<400> SEQUENCE: 65
tggcttgact cagaaacttg acccaggact gaaaagtagc tgaagtaaaa atttatagtg         60
gctcagctca cagtagaaag catatccaga aaaagaagaa agaagaagaa gaagaagaag        120
cagaagaaga agaagaagaa gaagaagaag aagaagaaga agaagaagaa gaagaagaag        180
aagaagaaga ggaagaggaa gaagaagaag aagaagaaga agaagaagaa gaagaagaag        240
aagaagaaga agaagaagaa gaagaaaagt gctcactgaa gcacactgaa gctccct           297

<210> SEQ ID NO 66
```

-continued

```
<211> LENGTH: 300
<212> TYPE: DNA
<213> ORGANISM: Homo sapiens

<400> SEQUENCE: 66
agggagcttc agtgtgcttc agtgagcact tttcttcttc ttcttcttct tcttcttctt      60
cttcttcttc ttcttcttct tcttcttctt cttcttcctc ttcctcttct tcttcttctt     120
cttcttcttc ttcttcttct tcttcttctt cttcttcttc ttcttcttct tcttcttctg     180
cttcttcttc ttcttcttct tcttcttttt tctggatatg ctttctactg tgagctgagc     240
cactataaat ttttacttca gctacttttc agtcctgggt caagtttctg agtcaagcca     300

<210> SEQ ID NO 67
<211> LENGTH: 435
<212> TYPE: DNA
<213> ORGANISM: Homo sapiens

<400> SEQUENCE: 67
gcctgggcaa caaaagtgac actctgtctc aagaaagaag gaaggaagga aggaaggaag      60
gaaggaagga aggagagaaa gaaagaaaga caaagaaaga aagaaagaaa gaaagaaaga     120
aagaaagaaa gaaagaaaga aagaaagaaa gagaaagaga gaaagaaaga aagaaagaga     180
aagagagaga gaaagagaga aaatgaaaga aaaagaagga aggaaggaag gaagaaagaa     240
agaaagaaag aaagaaagaa agaaagaaag aaagaaagaa agaaagaaaa gaaaagaaag     300
aaagaaagaa ggaaggaagg aaagagaaag aaagaaagga aggaaggaag gaaggaagga     360
aggaaggaag gaaggaagga aggaaggaag gaaggaagca ctgtaaccat ctttttgtaga     420 acaggtctgc tgtgc                                                      435

<210> SEQ ID NO 68
<211> LENGTH: 441
<212> TYPE: DNA
<213> ORGANISM: Homo sapiens

<400> SEQUENCE: 68
gcctgggcaa caaaagtgac actctgtctc aagaaagaag gaaggaagga aggaaggaag      60
gaaggaagga aggaaggaag gaaggagaga aagaaagaaa gacaaagaaa gaaagaaaga     120
aagaaagaaa gaaagaaaga aagaaagaaa gaaagaaaga agaaagaga gaaagaaaga     180 aagaaagaga aagagagaga gaaagagaga aaatgaaaga aaaagaagga aggaaggaag     240
gaaggaagga agaaagaaag aaagaaagaa agaaagaaag aaagaaagaa agaaagaaat     300
aaaagaaaag aaagaaagaa agaaggaagg aaggaaagag aaagaaagaa aggaagaaag     360
gaaggaagga aggaaggaag gaaggaagga aggaaggaag gaagcactgt aaccatcttt     420
tgtagaacag gtctgctgtg c                                              441

<210> SEQ ID NO 69
<211> LENGTH: 433
<212> TYPE: DNA
<213> ORGANISM: Homo sapiens

<400> SEQUENCE: 69
gcacagcaga cctgttctac aaaagatggt tacagtgctt ccttccttcc ttccttcctt      60
ccttccttcc ttccttcctt tcttcctttc tttctttctc tttccttcct tccttctttc     120
tttctttctt ttctttttatt tctttcttttc tttctttctt tctttctttc tttctttctt     180
tctttctttc tttcttcctt ccttccttcc ttccttcctt cttttctttt cattttctct     240
```

```
ctttctctct ctctttctct ttctttcttt ctttctctct ttctttcttt ctttcttct         300 ttctttcttt ctttctttct ttctttcttt ctttctttgt ctttctttct ttctctcctt         360
ccttccttcc ttccttcctt ccttccttcc ttccttcttt cttgagacag agtgtcactt         420
ttgttgccca ggc                                                            433

<210> SEQ ID NO 70
<211> LENGTH: 397
<212> TYPE: DNA
<213> ORGANISM: Homo sapiens

<400> SEQUENCE: 70
tattctagac tctgctcaga gaggtggtga ttacatattg cagagcccag cacctaggtt          60
aagtgacctt cttcttcttc tttcttcttc ttcttcttct tcttcttctt cttcttcttc         120
ttcttcttct tcttcttctt cttcttcttc ttcttcttct tcttcttctt cttctcctcc         180
tccttctcct tcttcttctc cttctccttc tccttctcct tctcctactt cttcttcttc         240
ttcttcttct tcttcttctt cttcttcttc ttcttcttct tcttcttctt cttcttcttc         300
ttctcctcct tcttctttat tcttctgtct ttgttttgt tttgagacag agtcttgcac          360
tgttgctcgg gctggagtga agagatacaa tgacagc                                  397

<210> SEQ ID NO 71
<211> LENGTH: 420
<212> TYPE: DNA
<213> ORGANISM: Homo sapiens

<400> SEQUENCE: 71
gcaagaccat gtcttgaaag taagggaaag cgaggggtaa gtagtggaag ggaggaggag          60 gaaaggggg gagagagaga gagagaaaga aagaaagaaa tagaaagaaa gaaagaaaga         120
aagaaagaaa gaaagaaaga aagaaagaaa gaaagagaga gaaagaaaga aaggaaagaa         180
agaaagaaag aaagaaagaa agaaagaaag aaagaaagaa agaaacagag aaagaaagaa         240
agaaagagaa agaaagaaag aaagaaagaa agaaagaaag aaagaaaaag aaaagaaaga         300
ggaagaaaga aagaaagaaa aagagaaaga aaggagggag ggagggaagg aaagaaggaa         360
ggagagatgt gatgttactt tagagctttg aatatataaa agcaaataat gaggacttgc         420

<210> SEQ ID NO 72
<211> LENGTH: 435
<212> TYPE: DNA
<213> ORGANISM: Homo sapiens

<400> SEQUENCE: 72
gcaagtcctc attatttgct tttatatatt caaagctcta aagtaacatc acatctctcc          60
ttccttcttt ccttccctcc ctccctcctt tctttctctt tttctttctt tctttcttcc         120
tctttctttt cttttctttt cttttcttct ttctttcttt ctttctttct ttctttcttt         180
ctttctcttt ctttctttct ttctctgttt ctttcttctt tctttctttc tttctttctt         240
tctttctttc tttctttcct ttctttcttt ctttctttcc ctttctttct ttctttcttt         300
ctttctttct ttctttcttt ctttctttct ttctatttct ttcttctttt ctctctctct         360
ctctcccccc ctttcctcct cctcccttcc actacttacc cctcgctttc ccttactttc         420
aagacatggt cttgc                                                          435

<210> SEQ ID NO 73
```

-continued

```
<211> LENGTH: 395
<212> TYPE: DNA
<213> ORGANISM: Homo sapiens

<400> SEQUENCE: 73
gtgagactcc atctcaaaag aagaaagaag gaaagaaaga aagaaaggaa cgaaggaagg      60
aaggaaggaa ggaaggaagg aaggaaggaa ggaaggaaga aagaaagaga aagaaagaaa     120
aaagagggag ggagggaagg aggaaggaag gaaagagaga gagagggaga gagaacggaa     180
gaaagaaaga aagaaagaaa gaaagaaaga aagaaagaaa gaaagaaaga aagaaagaaa     240
gaaagaaaga aaggtagaaa gaaagaaaga aagaaagaaa gaaagaaaga aagaaagaaa     300
gaaagaaaga aagagaaaga aagaaagaaa gaaaaagaaa gaaagaaaaa gaaaggaaag     360
ttttgccagg agaagctgtc cttcacacac cagat                                395

<210> SEQ ID NO 74
<211> LENGTH: 468
<212> TYPE: DNA
<213> ORGANISM: Homo sapiens

<400> SEQUENCE: 74
gcacatgtct atagtcccat ctacccagga ggatgaggca ggaggattgc ttgagccagg      60
ggtaagataa tatggcaccg tggctctcca gcctgggtaa catggtgaga ccctgtctga     120
aagaaaagaa aagaaagaaa gaaagaaaga aagaaagaaa gaaagaaaga aagaaagaaa     180
gaaagagaaa gaaagaaaga gaaagaaaga aagaaagaaa gagaaagaaa gaaagaaaga     240
aagaaagaaa gaaagaaaga aagaaagaaa gaaagaaagg gaaagggaga aagagagaga     300
gacagcaaga gaaagagaga gagataagga gggaaggagg gagggaggat gggatgaaag     360
aaggaaagaa gggaaggaagg gaagaaaagg aggtggtgag ggagattaag agatgacaga     420
tgagtgtggc cacagtttgg ctgaaattct caagaattac tcagtggc                  468

<210> SEQ ID NO 75
<211> LENGTH: 392
<212> TYPE: DNA
<213> ORGANISM: Homo sapiens

<400> SEQUENCE: 75
agaatctatg atcacagcac ttttctgaat cctggacaag tgagaaaaga aagaaagaaa      60
gaaagaaaga aagaaagaaa gaaagaaaga aagaaagaaa gaaagaaaga aagagagaga     120
gagagagaga gagagagaga aagaaagaaa gaaagaaaga aagaaagaaa gaaagaaaga     180
aagaaaaaag agagggaggg agagagtatg aggaagggag ggagggagta tgaggaaggg     240 agggaggggag caaggaagga aggagaaagg agggaggaaa ggaaggaggg aggggaggagg     300 gaaggaagga agaaagggag gaagggagga aggaaggaaa agaagaagga agaaagaaaa     360
gaaaaaggac agaaagaaaa tgaggtagaa ag                                    392

<210> SEQ ID NO 76
<211> LENGTH: 283
<212> TYPE: DNA
<213> ORGANISM: Homo sapiens

<400> SEQUENCE: 76
gcaagactcc atctccaaaa agaaagaaag aaagaaagaa agaaagaaag aaagaaagaa      60
agaaagaaag aaagaaggaa aagaaagaa agaaagaaag gaaagaaaag aaagaaagaa     120
agaaagaaaa gaaagaaaga aggaaagaag gaaagaaggaa aagaaggaa gaaggaagga     180
```

-continued

```
aagaaagaaa gaaagaaaga aagaaagaaa gaaagaaaga aagaaagaaa gaaagaaaga      240
aagttagtta ataatggcat tactcataat ggacccaagc ttg                       283

<210> SEQ ID NO 77
<211> LENGTH: 305
<212> TYPE: DNA
<213> ORGANISM: Homo sapiens

<400> SEQUENCE: 77
gggctttata agttatctga ggctgttata atctttaaac ttttttttac cagaaatcga       60
tttattcacg cttgtctttc tttctttctt tctttctttc tttctttctt tctttctttc      120
tttctttctt tctttctttc tttctttctc tttctttctg tctttttttct ttctctttct      180 ttctttcttt ctttctttct ttctttcttt ctttctttct ttttctttct ttctttcttt      240
cttccttctt tctcttttct ttttttatta tttatttatt tattttttaag atggagtctg      300 tcacc                                                                   305

<210> SEQ ID NO 78
<211> LENGTH: 420
<212> TYPE: DNA
<213> ORGANISM: Homo sapiens

<400> SEQUENCE: 78
gtggctcact cctataacct agtttggaag gtcaaggagg gtggattgct tgagcccaga       60
agttcaagaa cagcctgggt aacagtgtga gatagatata tagatagata gatgatagata     120 tagatagata gatagataga tagatagata gatgatagata cagacagaca gacagacagg     180
atgtcatttg tttatatcat ttaattataa gtgttcatgg gctgtaccat ataatactgt      240
taagatgaca ctactcttaa atttgaactg catatcataa tccctggtgg ctttttggcgc     300 aaacacaaaa ctgatcctgt ggaaaataca aggtacctag aggagccaaa ataactttgc      360
aaaaaaggaa ccaaggtgaa aaaaatcata ctaaccagtc tcaaaactta ctacaaagtt      420

<210> SEQ ID NO 79
<211> LENGTH: 378
<212> TYPE: DNA
<213> ORGANISM: Homo sapiens

<400> SEQUENCE: 79
tcccagagtc tcagagtgct ggaatgatgg gcatgagcca ctttgcctgg cctcctggta       60
atcactcaca accacgacat gtgttctgat tttttttctt tctttttcttt tctttctctc      120 tctttctttc tttccttcct tccttccttc cttccttcct tccttccttc cttccttcct      180
tccttccttc cttcatttct tcctctcttt ctttctttct ttctttcttt cttctctttc      240 ttctttttttt gatggagtct tgctctgtgt gaggcgagga gcatcacctt ggaagccaca      300
gcaccgcatt acaaagcccc attcacatgc acaaagcttt attcccttcc tgaattccta      360
gctggtgact tctatggc                                                    378

<210> SEQ ID NO 80
<211> LENGTH: 374
<212> TYPE: DNA
<213> ORGANISM: Homo sapiens

<400> SEQUENCE: 80
gccatagaag tcaccagcta ggaattcagg aagggaataa agctttgtgc atgtgaatgg       60
```

-continued

```
ggctttgtaa tgcggtgctg tggcttccaa ggtgatgctc ctcgcctcac acagagcaag      120
actccatcaa aaaaagaaga aagagaagaa agaaagaaag aaagaaagaa agagaggaag      180
aaatgaagga aggaaggaag gaaggaagga aggaaggaag gaaggaagga aggaaggaag      240
gaaagaaaga aagagagaga aagaaaagaa aagaaagaaa aaaaatcaga acacatgtcg      300
tggttgtgag tgattaccag gaggccaggc aaagtggctc atgcccatca ttccagcact      360
ctgagactct ggga                                                       374

<210> SEQ ID NO 81
<211> LENGTH: 543
<212> TYPE: DNA
<213> ORGANISM: Homo sapiens

<400> SEQUENCE: 81
ttatcttgct gaccattaga gaagatgggg tcactaacag atagatagat aggtaggtag       60
gcagatagat agatagatag atagatagat agatagatag atagattgat agataataga      120
tgtgaatcga tagatggaaa tggatggata gtaagatgat agctaggtga tatatgtata      180
tatagacaga tagatagaaa gatagataga tagatagata gatgatagag atggatagat      240
atagatacat agataaatga tagctcataa tggatagata taggtagata gaggtggaga      300
gataaaagac agaaagtaag acatatagat atagataagc agataggtga tagatagata      360 gatagatagat atagatagata gatagataga tagaaggtag agatagaaac aggtagacag      420
gtatatagat gatgggtata tagatgagag agatagatag atagatagat agatagatag      480
atagatagat aggcaggcag gcagacagag agacagatac ataggcaggt aggtaggtag      540
agg                                                                   543

<210> SEQ ID NO 82
<211> LENGTH: 470
<212> TYPE: DNA
<213> ORGANISM: Homo sapiens

<400> SEQUENCE: 82
accttctggc gaagtaaccc aaacgtttac tttcttctc tttttctctt tttttcttta       60
tttttctttc tctgttcttt ttctctcctt ccttccttcc ttccttcctt ccttccttcc      120
ttccttcctt ccttctttcc ctccttcttt ctctttacct tctggtgaac tgactcgaac      180
ctttacttac tttctttcta ttttttctcta ttttttctct ttcttcctgt cctttccttt      240
cttttccttt cctttccttt cctttccttt cctttccttt cctttcctct      300
ctttctcttt ctctctttct cttccttccc ttcccttccc tttcctctct ttctttcttt      360 ctttcttttct ttctttcttt ctttctttct ttctttcttt ttctttcttt cttttttcttt      420 ctttctacag ggtctcactc tgtcacccaa gctagagtgc agtgctgaga               470

<210> SEQ ID NO 83
<211> LENGTH: 632
<212> TYPE: DNA
<213> ORGANISM: Homo sapiens

<400> SEQUENCE: 83
gagtgaaacc atctctaaga cataaagaaa gaactaaaag agaaagaaa agaaggaagg       60 caggaaggaa ggaagaaagg aaggaaggaa ggagtgaggg agggagggag ggagggaaaa      120
aagaaagaag ggagagagag ggagaaagag aaggaaggag agtaggaaaa aggaaggaag      180
gaatgaagag aggaaagaag agaaagaaga aagaatgaag gaagataaaa agacagaaag      240
```

-continued

```
aagggagaga gggagggagg gaaggaaagt acaaaaaaga aggaagaaag aaggaaggaa        300
ggaaggaaaa aagagaaaaa gaaagacaga aagaaagaga gaaagaaagg agagaggaag        360
gaaggaagga aggaaggaag gaagacagag aaaaaaagaa agaaacaaac aaacaaagag        420
aaagaaaaaa gagagaaaga aagagagaaa gaaagaaagg aaaagaaaga aagagagaaa        480
gaaagaaaga aagaaagaaa gaaagaaaga aagaaagaaa gaaagaaaga gaaagaaaga        540
aggaaggaaa ggaaggaagg aaggaaagga aggaaggaag gaaagaaaga aagaggggga        600
atagagaagt ccatcatggt gtgtttgcaa gc                                     632

<210> SEQ ID NO 84
<211> LENGTH: 229
<212> TYPE: DNA
<213> ORGANISM: Homo sapiens

<400> SEQUENCE: 84
ataggacagg tggttgaatg gctagcactc catgagcttt attcatgtat atttataaaa         60
gtgcaatttc tttttctttc tttctttctt tctttctttc tttctttctt tctttctttc        120
tttctttctt tctttctttc tttctatatt atagcaaact cttgtacatt tacttactta        180
ttttctttca gtgatcatgc tagtatggtt gtactatctg aaaatctag                     229

<210> SEQ ID NO 85
<211> LENGTH: 464
<212> TYPE: DNA
<213> ORGANISM: Homo sapiens

<400> SEQUENCE: 85
ctatagttcc tagagcaaag agtgagctgc catttttttcc tgtttgtgtg actaagctgt         60
tcctgcctcc tggctttgga ggatccaaat aaactgtgga tggaagtggt acctctgcaa        120
agcagagctg ttctacaaaa atgtggctag actttccttt cctttccttt cctttccttt        180
cctttccttt cctttccttt cctttccttt ccttccctcc ctccctccct ccctccctcc        240
cttctttctc tttctttctt tctttctttc cttccttcct tccttccttc cttccttcct        300
tccttccttc cttccttcct tctttctttc tttctttctt tctttctttc tttctttctt        360
tctttctttc ttccttcctt ccttccttct ttctttcgag acagagtatt cccccctgttg        420 cccaggctgg agtgcactgg ggcaatctca gattaccaca acct                         464

<210> SEQ ID NO 86
<211> LENGTH: 400
<212> TYPE: DNA
<213> ORGANISM: Homo sapiens

<400> SEQUENCE: 86
gcaaagcaga atatttatgt ttcagtgtac tttattcatc cgttgcgggt tcaggggtct         60
gcaagggaca gaccccccaaa gttggtgcca cagcatgaga agtgtgagaa gtgttaccac        120
agtttctcct tccttccttc cttccttcct tccttccttc cttccttcct tccttccttc        180
cttccttcct tcctccctcc ctccctccct ctctctctct ctctctttat ttccttggtg        240
gggagtaaaa tggcacctag ctaggtcacc caggctggag tgcagtcaca tgatctcagc        300
tcactgcaaa tatcccctcc caggttcaag tgattatctt gcctcagcct ctagcatagc        360
tgggataaaa ggcacttgcc accacacctc gcaaattttt                              400

<210> SEQ ID NO 87
```

```
<211> LENGTH: 400
<212> TYPE: DNA
<213> ORGANISM: Homo sapiens

<400> SEQUENCE: 87
gcaaagcaga atatttatgt ttcagtgtac tttattcatc cgttgcgggt tcaggggtct      60
gcaagggaca gaccccaaa gttggtgcca cagcatgaga agtgtgagaa gtgttaccac     120
agtttctcct tccttccttc cttccttcct tccttccttc cttccttcct tccttccttc    180
cttccttcct tcctccctcc ctccctccct ctctctctct ctctctttat ttccttggtg    240
gggagtaaaa tggcacctag ctaggtcacc caggctggag tgcagtcaca tgatctcagc    300
tcactgcaaa tatcccctcc caggttcaag tgattatctt gcctcagcct ctagcatagc    360
tgggataaaa ggcacttgcc accacacctc gcaaattttt                          400

<210> SEQ ID NO 88
<211> LENGTH: 372
<212> TYPE: DNA
<213> ORGANISM: Homo sapiens

<400> SEQUENCE: 88
caagaccagc atatcagttg aggccaggag tttgagacca gcctggccta catagtggaa      60
cctcatctct actaaaaata gaaaagaaag aagaagaaga agaagaagaa gaagaggaag     120
aagaggaaga agaagaaggg ggagaagaag ggggagaaga aggggagaa gaaggggag     180 aagaaggggg agaagaagaa gaagaagagg aagaggaaga ggaagaggaa gaagaagaag    240
aagaagaaga agaagaagaa gaagaagaag aagaagaaga agaagaagaa gaagagagcc    300
aggaaaggag ccaggtgtgg tggcatgcac ctgtagtccc agctgagcag gagtaggagg    360
ttgcagtgag cc                                                        372

<210> SEQ ID NO 89
<211> LENGTH: 406
<212> TYPE: DNA
<213> ORGANISM: Homo sapiens

<400> SEQUENCE: 89
cacctgtaat cctagctact cagaaggctg aggcaggagg attgcttgaa tcctggaagt      60
ggaggttgca gtgagccaag atcacaccac tgcactccag cctgagtgac agagcgagac     120
tccatctcaa caaaaaagaa agaaagaaag aaagaaagaa agaaagaaag aaagaaagaa    180
agaaagaaag aaagaaagaa agaaagaaag atgtttaatt gactctcagt tccacaggcc    240
atacaggaag catggcttgg caggcctcag gaaacacaat catggcagaa ggtgaaggg     300 aaggaggcat gtcttacttg gctggagaag gaggaagaga gctaaagcgg gaatgctgta    360
cacttttaaa caaccagatc tcatgagcac tctatgatga gaaagc                   406

<210> SEQ ID NO 90
<211> LENGTH: 406
<212> TYPE: DNA
<213> ORGANISM: Homo sapiens

<400> SEQUENCE: 90
gctttctcat catagagtgc tcatgagatc tggttgttta aaagtgtaca gcattcccgc      60
tttagctctc ttcctccttc tccagccaag taagacatgc ctccttcccc ttcaccttct     120
gccatgattg tgtttcctga ggcctgccaa gccatgcttc ctgtatggcc tgtggaactg     180
agagtcaatt aaacatcttt ctttctttct ttctttcttt ctttctttct ttctttcttt    240
```

-continued

```
ctttctttct ttctttcttt ctttctttct tttttgttga gatggagtct cgctctgtca      300
ctcaggctgg agtgcagtgg tgtgatcttg gctcactgca acctccacct ccaggattca      360
agcaatcctc ctgcctcagc cttctgagta gctaggatta caggtg                      406

<210> SEQ ID NO 91
<211> LENGTH: 19
<212> TYPE: DNA
<213> ORGANISM: Artificial Sequence
<220> FEATURE:
<223> OTHER INFORMATION: primer

<400> SEQUENCE: 91
aagcagagcc acacagact                                                      19

<210> SEQ ID NO 92
<211> LENGTH: 20
<212> TYPE: DNA
<213> ORGANISM: Artificial Sequence
<220> FEATURE:
<223> OTHER INFORMATION: primer

<400> SEQUENCE: 92
gtttgcctgt aagtggagcc                                                     20

<210> SEQ ID NO 93
<211> LENGTH: 20
<212> TYPE: DNA
<213> ORGANISM: Artificial Sequence
<220> FEATURE:
<223> OTHER INFORMATION: primer

<400> SEQUENCE: 93
acagcgcagg attccatcta                                                     20

<210> SEQ ID NO 94
<211> LENGTH: 21
<212> TYPE: DNA
<213> ORGANISM: Artificial Sequence
<220> FEATURE:
<223> OTHER INFORMATION: primer

<400> SEQUENCE: 94
tgcctttcat tctctccttc g                                                   21

<210> SEQ ID NO 95
<211> LENGTH: 22
<212> TYPE: DNA
<213> ORGANISM: Artificial Sequence
<220> FEATURE:
<223> OTHER INFORMATION: primer

<400> SEQUENCE: 95
gaggagatta ggarcacagt ga                                                  22

<210> SEQ ID NO 96
<211> LENGTH: 21
<212> TYPE: DNA
<213> ORGANISM: Artificial Sequence
<220> FEATURE:
<223> OTHER INFORMATION: primer

<400> SEQUENCE: 96
tgcaaggtgt gggtgaaaat t                                                   21
```

-continued

```
<210> SEQ ID NO 97
<211> LENGTH: 20
<212> TYPE: DNA
<213> ORGANISM: Artificial Sequence
<220> FEATURE:
<223> OTHER INFORMATION: primer

<400> SEQUENCE: 97
ctgggtgtgc attcgagact                                              20

<210> SEQ ID NO 98
<211> LENGTH: 20
<212> TYPE: DNA
<213> ORGANISM: Artificial Sequence
<220> FEATURE:
<223> OTHER INFORMATION: primer

<400> SEQUENCE: 98
gttgcaggga gtggagattg                                              20

<210> SEQ ID NO 99
<211> LENGTH: 23
<212> TYPE: DNA
<213> ORGANISM: Artificial Sequence
<220> FEATURE:
<223> OTHER INFORMATION: primer

<400> SEQUENCE: 99
gcccttgttt ctataagtgg tca                                          23

<210> SEQ ID NO 100
<211> LENGTH: 20
<212> TYPE: DNA
<213> ORGANISM: Artificial Sequence
<220> FEATURE:
<223> OTHER INFORMATION: primer

<400> SEQUENCE: 100
gtttgggtta cttcgccaga                                              20

<210> SEQ ID NO 101
<211> LENGTH: 18
<212> TYPE: DNA
<213> ORGANISM: Artificial Sequence
<220> FEATURE:
<223> OTHER INFORMATION: primer

<400> SEQUENCE: 101
cagggagctt cagtgtgc                                                18

<210> SEQ ID NO 102
<211> LENGTH: 20
<212> TYPE: DNA
<213> ORGANISM: Artificial Sequence
<220> FEATURE:
<223> OTHER INFORMATION: primer

<400> SEQUENCE: 102
tggctcagct cacagtagaa                                              20

<210> SEQ ID NO 103
<211> LENGTH: 20
<212> TYPE: DNA
<213> ORGANISM: Artificial Sequence
<220> FEATURE:
<223> OTHER INFORMATION: primer
```

<400> SEQUENCE: 103
tgggccaaga tctcgtcatt                                           20

<210> SEQ ID NO 104
<211> LENGTH: 20
<212> TYPE: DNA
<213> ORGANISM: Artificial Sequence
<220> FEATURE:
<223> OTHER INFORMATION: primer

<400> SEQUENCE: 104
tcacatgtag cactctgggc                                           20

<210> SEQ ID NO 105
<211> LENGTH: 20
<212> TYPE: DNA
<213> ORGANISM: Artificial Sequence
<220> FEATURE:
<223> OTHER INFORMATION: primer

<400> SEQUENCE: 105
cagtcagcca agatgccaaa                                           20

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
gcaacactta agagacggca                                           20

<210> SEQ ID NO 107
<211> LENGTH: 22
<212> TYPE: DNA
<213> ORGANISM: Artificial Sequence
<220> FEATURE:
<223> OTHER INFORMATION: primer

<400> SEQUENCE: 107
gcaagactcc atctccaaaa ag                                         22

<210> SEQ ID NO 108
<211> LENGTH: 20
<212> TYPE: DNA
<213> ORGANISM: Artificial Sequence
<220> FEATURE:
<223> OTHER INFORMATION: primer

<400> SEQUENCE: 108
caagcttggg tccattatga                                           20

<210> SEQ ID NO 109
<211> LENGTH: 21
<212> TYPE: DNA
<213> ORGANISM: Artificial Sequence
<220> FEATURE:
<223> OTHER INFORMATION: primer

<400> SEQUENCE: 109
tggatggaag tggtacctct g                                          21

<210> SEQ ID NO 110

```
<211> LENGTH: 23
<212> TYPE: DNA
<213> ORGANISM: Artificial Sequence
<220> FEATURE:
<223> OTHER INFORMATION: primer

<400> SEQUENCE: 110
aggttgtggt aatctgagat tgc                                              23

<210> SEQ ID NO 111
<211> LENGTH: 20
<212> TYPE: DNA
<213> ORGANISM: Artificial Sequence
<220> FEATURE:
<223> OTHER INFORMATION: primer

<400> SEQUENCE: 111
ctactccaaa ggctgcagga                                                  20

<210> SEQ ID NO 112
<211> LENGTH: 20
<212> TYPE: DNA
<213> ORGANISM: Artificial Sequence
<220> FEATURE:
<223> OTHER INFORMATION: primer

<400> SEQUENCE: 112
cgccctcaca ccctttcttt                                                  20

<210> SEQ ID NO 113
<211> LENGTH: 23
<212> TYPE: DNA
<213> ORGANISM: Artificial Sequence
<220> FEATURE:
<223> OTHER INFORMATION: primer

<400> SEQUENCE: 113
ggtaagataa tatggcaccg tgg                                              23

<210> SEQ ID NO 114
<211> LENGTH: 21
<212> TYPE: DNA
<213> ORGANISM: Artificial Sequence
<220> FEATURE:
<223> OTHER INFORMATION: primer

<400> SEQUENCE: 114
ccctccttcc ctccttatct c                                                21

<210> SEQ ID NO 115
<211> LENGTH: 19
<212> TYPE: DNA
<213> ORGANISM: Artificial Sequence
<220> FEATURE:
<223> OTHER INFORMATION: primer

<400> SEQUENCE: 115
gcgagactcc atctcaaca                                                   19

<210> SEQ ID NO 116
<211> LENGTH: 17
<212> TYPE: DNA
<213> ORGANISM: Artificial Sequence
<220> FEATURE:
<223> OTHER INFORMATION: primer

<400> SEQUENCE: 116
```

-continued

--- ccacccaaat ctcacgt                                                      17

<210> SEQ ID NO 117
<211> LENGTH: 23
<212> TYPE: DNA
<213> ORGANISM: Artificial Sequence
<220> FEATURE:
<223> OTHER INFORMATION: primer

<400> SEQUENCE: 117
agtactttga gtttcccaga agg                                               23

<210> SEQ ID NO 118
<211> LENGTH: 20
<212> TYPE: DNA
<213> ORGANISM: Artificial Sequence
<220> FEATURE:
<223> OTHER INFORMATION: primer

<400> SEQUENCE: 118
aaggagccca ggattgagag                                                   20

<210> SEQ ID NO 119
<211> LENGTH: 20
<212> TYPE: DNA
<213> ORGANISM: Artificial Sequence
<220> FEATURE:
<223> OTHER INFORMATION: primer

<400> SEQUENCE: 119
gtctcactag ctggtcaggg                                                   20

<210> SEQ ID NO 120
<211> LENGTH: 20
<212> TYPE: DNA
<213> ORGANISM: Artificial Sequence
<220> FEATURE:
<223> OTHER INFORMATION: primer

<400> SEQUENCE: 120
gtcgtggtgg taagtgcatt                                                   20

<210> SEQ ID NO 121
<211> LENGTH: 20
<212> TYPE: DNA
<213> ORGANISM: Artificial Sequence
<220> FEATURE:
<223> OTHER INFORMATION: primer

<400> SEQUENCE: 121
tctgactcct tgactcccaa                                                   20

<210> SEQ ID NO 122
<211> LENGTH: 19
<212> TYPE: DNA
<213> ORGANISM: Artificial Sequence
<220> FEATURE:
<223> OTHER INFORMATION: primer

<400> SEQUENCE: 122
tgtctctctg tctgcctgc                                                    19

<210> SEQ ID NO 123
<211> LENGTH: 21
<212> TYPE: DNA

-continued

```
<213> ORGANISM: Artificial Sequence
<220> FEATURE:
<223> OTHER INFORMATION: primer

<400> SEQUENCE: 123
ttgagcccag aagttcaaga a                                              21

<210> SEQ ID NO 124
<211> LENGTH: 23
<212> TYPE: DNA
<213> ORGANISM: Artificial Sequence
<220> FEATURE:
<223> OTHER INFORMATION: primer

<400> SEQUENCE: 124
ggtaccttgt attttccaca gga                                           23

<210> SEQ ID NO 125
<211> LENGTH: 23
<212> TYPE: DNA
<213> ORGANISM: Artificial Sequence
<220> FEATURE:
<223> OTHER INFORMATION: primer

<400> SEQUENCE: 125
tggtgattac atattgcaga gcc                                           23

<210> SEQ ID NO 126
<211> LENGTH: 23
<212> TYPE: DNA
<213> ORGANISM: Artificial Sequence
<220> FEATURE:
<223> OTHER INFORMATION: primer

<400> SEQUENCE: 126
gctgtcattg tatctcttca ctc                                           23

<210> SEQ ID NO 127
<211> LENGTH: 20
<212> TYPE: DNA
<213> ORGANISM: Artificial Sequence
<220> FEATURE:
<223> OTHER INFORMATION: primer

<400> SEQUENCE: 127
agctgaggaa gagaatggcg                                               20

<210> SEQ ID NO 128
<211> LENGTH: 23
<212> TYPE: DNA
<213> ORGANISM: Artificial Sequence
<220> FEATURE:
<223> OTHER INFORMATION: primer

<400> SEQUENCE: 128
gcaaatgtaa gtctgtctct gga                                           23

<210> SEQ ID NO 129
<211> LENGTH: 20
<212> TYPE: DNA
<213> ORGANISM: Artificial Sequence
<220> FEATURE:
<223> OTHER INFORMATION: primer

<400> SEQUENCE: 129
ttgcataggt agagggaggc                                               20
```

-continued

```
<210> SEQ ID NO 130
<211> LENGTH: 20
<212> TYPE: DNA
<213> ORGANISM: Artificial Sequence
<220> FEATURE:
<223> OTHER INFORMATION: primer

<400> SEQUENCE: 130
gcttaggatt ggacccagga                                                  20

<210> SEQ ID NO 131
<211> LENGTH: 22
<212> TYPE: DNA
<213> ORGANISM: Artificial Sequence
<220> FEATURE:
<223> OTHER INFORMATION: primer

<400> SEQUENCE: 131
gtctctcaag cctgttctat ga                                               22

<210> SEQ ID NO 132
<211> LENGTH: 23
<212> TYPE: DNA
<213> ORGANISM: Artificial Sequence
<220> FEATURE:
<223> OTHER INFORMATION: primer

<400> SEQUENCE: 132
tggacaacaa gagtaagaca gaa                                              23

<210> SEQ ID NO 133
<211> LENGTH: 21
<212> TYPE: DNA
<213> ORGANISM: Artificial Sequence
<220> FEATURE:
<223> OTHER INFORMATION: primer

<400> SEQUENCE: 133
tgatggctca ttgtagtcca c                                                21

<210> SEQ ID NO 134
<211> LENGTH: 23
<212> TYPE: DNA
<213> ORGANISM: Artificial Sequence
<220> FEATURE:
<223> OTHER INFORMATION: primer

<400> SEQUENCE: 134
agctgttaac cttcccaaat tgt                                              23

<210> SEQ ID NO 135
<211> LENGTH: 23
<212> TYPE: DNA
<213> ORGANISM: Artificial Sequence
<220> FEATURE:
<223> OTHER INFORMATION: primer

<400> SEQUENCE: 135
tctgtttctg cattgtttca ctt                                              23

<210> SEQ ID NO 136
<211> LENGTH: 22
<212> TYPE: DNA
<213> ORGANISM: Artificial Sequence
<220> FEATURE:
```

-continued

<223> OTHER INFORMATION: primer

<400> SEQUENCE: 136
tgagtgacag agcataaacg tg                                                    22

<210> SEQ ID NO 137
<211> LENGTH: 20
<212> TYPE: DNA
<213> ORGANISM: Artificial Sequence
<220> FEATURE:
<223> OTHER INFORMATION: primer

<400> SEQUENCE: 137
tctcagccaa gcaacatagc                                                       20

<210> SEQ ID NO 138
<211> LENGTH: 20
<212> TYPE: DNA
<213> ORGANISM: Artificial Sequence
<220> FEATURE:
<223> OTHER INFORMATION: primer

<400> SEQUENCE: 138
tggcagtctc atttcctgga                                                       20

<210> SEQ ID NO 139
<211> LENGTH: 20
<212> TYPE: DNA
<213> ORGANISM: Artificial Sequence
<220> FEATURE:
<223> OTHER INFORMATION: primer

<400> SEQUENCE: 139
gcagaaaggg ccttaagaca                                                       20

<210> SEQ ID NO 140
<211> LENGTH: 20
<212> TYPE: DNA
<213> ORGANISM: Artificial Sequence
<220> FEATURE:
<223> OTHER INFORMATION: primer

<400> SEQUENCE: 140
cttgacactt gccatgggta                                                       20

<210> SEQ ID NO 141
<211> LENGTH: 20
<212> TYPE: DNA
<213> ORGANISM: Artificial Sequence
<220> FEATURE:
<223> OTHER INFORMATION: primer

<400> SEQUENCE: 141 gcgagggta agtagtggaa                                                        20

<210> SEQ ID NO 142
<211> LENGTH: 23
<212> TYPE: DNA
<213> ORGANISM: Artificial Sequence
<220> FEATURE:
<223> OTHER INFORMATION: primer

<400> SEQUENCE: 142
acatcacatc tctccttcct tct                                                   23

-continued

```
<210> SEQ ID NO 143
<211> LENGTH: 22
<212> TYPE: DNA
<213> ORGANISM: Artificial Sequence
<220> FEATURE:
<223> OTHER INFORMATION: primer

<400> SEQUENCE: 143
gttgtggtga tctgagattg ct                                            22

<210> SEQ ID NO 144
<211> LENGTH: 20
<212> TYPE: DNA
<213> ORGANISM: Artificial Sequence
<220> FEATURE:
<223> OTHER INFORMATION: primer

<400> SEQUENCE: 144
actggatgga agtggtacct                                               20

<210> SEQ ID NO 145
<211> LENGTH: 24
<212> TYPE: DNA
<213> ORGANISM: Artificial Sequence
<220> FEATURE:
<223> OTHER INFORMATION: primer

<400> SEQUENCE: 145
ggyaacagag caggattcca tcta                                          24

<210> SEQ ID NO 146
<211> LENGTH: 29
<212> TYPE: DNA
<213> ORGANISM: Artificial Sequence
<220> FEATURE:
<223> OTHER INFORMATION: primer

<400> SEQUENCE: 146
acatagttca aaattcatgt ggataatga                                     29

<210> SEQ ID NO 147
<211> LENGTH: 23
<212> TYPE: DNA
<213> ORGANISM: Artificial Sequence
<220> FEATURE:
<223> OTHER INFORMATION: primer

<400> SEQUENCE: 147
cggaggaaaa gaagtgattg tac                                           23

<210> SEQ ID NO 148
<211> LENGTH: 20
<212> TYPE: DNA
<213> ORGANISM: Artificial Sequence
<220> FEATURE:
<223> OTHER INFORMATION: primer

<400> SEQUENCE: 148
ccccaaagtg tgttgcatca                                               20

<210> SEQ ID NO 149
<211> LENGTH: 24
<212> TYPE: DNA
<213> ORGANISM: Artificial Sequence
<220> FEATURE:
<223> OTHER INFORMATION: primer
```

-continued

```
<400> SEQUENCE: 149
ggyaacagag caggattcca tcta                                              24

<210> SEQ ID NO 150
<211> LENGTH: 29
<212> TYPE: DNA
<213> ORGANISM: Artificial Sequence
<220> FEATURE:
<223> OTHER INFORMATION: primer

<400> SEQUENCE: 150
acatagtttg aaattcatgt ggataatga                                         29
```

Y-CHROMOSOMAL SHORT TANDEM REPEAT MARKERS FOR TYPING MALE INDIVIDUALS

CROSS-REFERENCE TO RELATED PATENT APPLICATIONS

This application is a U.S. National Stage Application under 35 U.S.C. § 371 of International Patent Application No. PCT/NL2021/050117 filed Feb. 19, 2021, which claims the benefit of priority of Patent Application No. EP 20158807.6 filed Feb. 21, 2020, both of which are incorporated by reference in their entireties. The International Application was published on Aug. 26, 2021, as International Publication No. WO 2021/167464 A1.

SEQUENCE LISTING

The instant application contains a Sequence Listing which has been submitted electronically in ASCII format and is hereby incorporated by reference in its entirety. Said ASCII copy, created on Aug. 16, 2022, is named P126196 Sequence Listing.txt and is 40,264 bytes in size.

FIELD OF THE INVENTION

The invention relates to a group of Y-chromosomal short tandem repeat (Y-STR) markers that provides increased sensitivity in discriminating male individuals.

BACKGROUND

Short Tandem Repeats (STRs) are the most common type of DNA markers used in forensic investigations. By producing DNA-profiles using a set of autosomal, highly polymorphic STRs, forensic investigators can link a human biological stain found at a crime-scene to the donor of the stain with extremely high confidence, provided that the autosomal STR profile of the stain donor is already known to the investigative authorities, for example as it is included in a national forensic DNA database.

However, to be successful, this approach typically requires single source DNA-samples, i.e. biological traces contributed solely by a single person from which DNA is obtained, which in some forensic cases is not available. The most important type of forensic cases, where such DNA mixtures contributed by two or more persons are typically encountered, is sexual assault cases. In most sexual assault cases, the obtained physical evidence, such as vaginal swabs taken from the victim after sexual assault happened, contains DNA from the female victim, i.e. from her epithelial cells, as well as from the male perpetrator, i.e. from his sperm or epithelial cells. In such cases and from such material, obtaining a reliable autosomal STR-profile belonging to the male perpetrator often is impossible, even after so called differential lysis, where sperm DNA is enriched in the DNA extraction procedure.

A solution to this limitation is the use of STRs located on the non-recombining and thus male-specific part of the human Y-chromosome (Y-STRs) (Kayser, 2017. Human Genetics 136:621-635). By analyzing polymorphic, male-specific Y-STRs from a male-female DNA mixture, a Y-STR-profile is derived solely from the male fraction of the DNA mixture, because females don't possess a Y-chromosome.

However, standard Y-STRs used in forensic genetics have a major limitation for forensic casework, as the bulk of the human Y-chromosome, including standard forensic Y-STRs, is transmitted from a father to his son without any change due to the lack of recombination. Thus, male relatives typically share the same standard Y-STR profile, termed haplotype, because the mutation rate of standard Y-STRs is relatively low (on average 1 mutation per each Y-STR locus per one thousand generations i.e. mutation rate p in the order of $10^{-3}$). Therefore, in contrast to an autosomal STR-profile match allowing individual specific conclusions (with the exception of monozygotic twins), a standard forensic Y-STR profile match does not identify a single male individual, but instead points to a group of related males belonging to the same paternal lineage all sharing the same haplotype based on Y-STRs. This allows differentiating unrelated males belonging to other paternal lineages, which can help police investigation to find an unknown perpetrator via focused investigation on the male part of the male suspect's paternal family. However, standard forensic Y-STRs do not identify a single male individual directly, as is generally wanted in forensic genetics.

To overcome this limitation of standard Y-STRs in forensic DNA analysis typically being unable to differentiate between paternally related males, it was previously postulated that Y-STRs with substantially higher mutation rates than those of standard Y-STRs could be useful for differentiating male relatives.

Published in 2010, all 186 Y-STR markers known at that time were investigated in almost 2000 DNA-confirmed father-son pairs and their mutation rates were estimated from direct observations of father—son allelic differences from these data. Out of these 186 previously identified Y-STRs, a set of fourteen markers was identified that exhibit a markedly higher mutation rate, compared to all other Y-STR tested, including the standard Y-STRs used in forensic DNA analysis at that time (Ballantyne et al., 2010. Am J Hum Gen 87: 341-453). These so called rapidly mutating Y-STRs (RM Y-STRs) are characterized by a mutation rate of at least one mutation per one hundred meiosis per each marker (mutation rate p in the order of $10^{-2}$), which is approximately ten-fold higher than that of standard Y-STRs used in forensic genetics (Goedbloed et al., 2009. Int J Leg Med 123: 471-482).

Using this set of fourteen RM Y-STRs, twenty seven percent of father-son pairs and forty six percent of brothers were differentiated as previously shown (Adnan et al., 2016. Forensic Sci Int Genet 25: 45-51). A fifteenth RM Y-STR marker has been described recently (Claerhout et al., 2018. Forensic Science Int: Genetics 34: 1-10). Although these findings constitute a significant step forward towards the final goal of identifying individual males via Y-chromosome analyses, the majority of closely related males still remain indistinguishable when using this set of RM Y-STR markers.

It can be expected that when finding additional RM Y-STRs and typing them in male individuals, more close and distant relatives will become separable by forensic Y-chromosome analysis. Thus, in order to further increase the effectiveness of distinguishing male relatives, especially closely related men, there is an urgent need for identifying novel RM Y-STR markers.

Moreover, their increased mutation rate makes RM Y-STRs also useful to differentiate unrelated males belonging to different paternal (sub)lineages. This has been empirically demonstrated for the set of previously identified fourteen RM Y-STRs in that they strongly increased the differentiation of unrelated males compared to standard forensic Y-STRs (Ballantyne et al., 2014. Human Mutation 35: 1021-1032). Thus it can be expected that novel RM Y-STRs will be beneficial not only for differentiating closely and distantly related males, but also for differentiating unrelated males belonging to different paternal lineages as well as for remotely related males belonging to the same paternal lineage to differentiate them into different paternal sublineages.

BRIEF DESCRIPTION OF THE INVENTION

Provided herein are eleven novel rapidly mutating (EM) Y-chromosomal short tandem repeat (Y-STR) markers, i.e. novel RM Y-STR loci for which we demonstrated for the first time that they have mutation rates $>10^{-2}$, and for which we empirically demonstrated in independent data (not used for mutation rate estimation) that they have the ability to improve the differentiation rate and/or differentiation capacity of paternally related men including close male relatives. The identification of these novel RM Y-STR markers was based on the development of a novel algorithm that assigns a mutability prediction score to a given Y-STR sequence. This algorithm makes use of i) the length of the uninterrupted repeat stretches, ii) the number of repeat stretches in a sequence, iii) the marker being a multi-copy marker, meaning that a highly similar sequence is found in multiple locations of the Y-chromosome and can be amplified with a single primer pair, and iv) the size of the repeated motif.

Accordingly, the invention relates to a group of Y-chromosomal short tandem repeat (Y-STR) markers comprising at least one RM Y-STR marker selected from the group consisting of DYF1000, DYF1001, DYF1002, DYR88, DYS685, DYS688, DYS712, DYS1003, DYS1007, DYS1010 and DYS1012. Please note that the DYF and DYS names starting from 1000 and higher are proprietary names. The DNA sequences of these markers are provided in FIG. 4.

Said one or more RM Y-STR markers preferably is selected from the group consisting of DYF1000, DYF1001, DYF1002, DYS1003, DYS1007, DYS1010 and DYS1012. Said group of Y-STR markers may comprise one or more previously identified RM Y-STR markers selected from the group consisting of DYF387S1, DYF399S1, DYF403S1a, DYF403S1b, DYF404S1, DYS449, DYS518, DYS526, DYS547, DYS570, DYS576, DYS612, DYS626, DYS627 and DYS724.

Said group of Y-STR markers preferably has a rate of differentiating two male subjects who are paternally related by three generations of at least 60%.

The invention further provides a set of amplification primers comprising primers for the amplification of at least one Y-STR marker of the group of Y-STR markers according to the invention, wherein the set of primers are configured to provide one or more amplicons of the at least one RM Y-STR markers selected from DYF1000, DYF1001, DYF1002, DYR88, DYS685, DYS688, DYS712, DYS1003, DYS1007, DYS1010 and DYS1012. Said set of amplification primers may comprise at least one fluorescently labeled amplification primer.

The invention further provides a method for amplifying an allele of at least one Y-STR marker, comprising the steps of: contacting a sample suspected to contain a DNA sample of a male subject with a set of amplification primers comprising primers for the amplification of the at least one allele of at least one Y-STR marker selected from DYF1000, DYF1001, DYF1002, DYR88, DYS685, DYS688, DYS712, DYS1003, DYS1007, DYS1010 and DYS1012; and amplifying an allele of the at least one RM Y-STR marker, thereby forming one or more amplicons of the allele.

A preferred method of the invention further comprises labeling the one or more amplicons with a fluorescent label, preferably during amplification. A further preferred method according to the invention allows identification of at least one allele of a RM Y-STR marker selected from DYF1000, DYF1001, DYF1002, DYR88, DYS685, DYS688, DYS712, DYS1003, DYS1007, DYS1010 and DYS1012. Said set of amplification primers preferably is the set of amplification primers as described herein above.

The invention further provides a method for identifying an allele of at least one RM Y-STR marker, comprising the step of contacting a sample suspected to contain a DNA sample of a male subject with a set of amplification primers; amplifying said DNA sample; and identifying an allele of at least one of DYF1000, DYF1001, DYF1002, DYR88, DYS685, DYS688, DYS712, DYS1003, DYS1007, DYS1010 and DYS1012 by sequencing the amplified DNA sample, or by sequencing such allele from non-amplified DNA.

The invention further provides a kit for amplifying an allele of a RM Y-STR marker selected from DYF1000, DYF1001, DYF1002, DYR88, DYS685, DYS688, DYS712, DYS1003, DYS1007, DYS1010 and DYS1012, said kit comprising the set of amplification primers according to the invention and a reference standard.

The invention further provides an use of a Y-STR marker for typing male individuals. Said Y-STR marker preferably is selected from DYF1000, DYF1001, DYF1002, DYR88, DYS685, DYS688, DYS712, DYS1003, DYS1007, DYS1010 and DYS1012, more preferably from DYF1000, DYF1001, DYF1002, DYS1003, DYS1007, DYS1010 and DYS1012. Said use preferably involves identification of said RM Y-STR marker by sequencing amplified or non-amplified DNA.

These typed male individuals can be closely paternally related males separated by one to only a few meiosis, which is typically known from family records or other records. As an alternative, the male individuals are distantly paternally related males separated by several meiosis, which may or may not be known from family records or other records. In addition, the typed male individuals can be remotely paternally related males separated by a large number of meiosis, which typically is unknown from family records or other records, and thus they are considered as unrelated persons despite the fact that they belong to the same paternal lineage. Furthermore, the typed male individuals can be paternally unrelated males belonging to different paternal lineages.

LEGENDS TO THE FIGURES

FIG. 1 shows an example of repeat stretches in two previously published RM Y-STR sequences to illustrate how the repetitive sequence was transformed in a format that was used for calculations of the mutability prediction score.

FIG. 2 demonstrates the correlation between non RM Y-STRs using the previously published 171 non RM Y-STRs (Ballantyne et al., 2010. Ibid) versus RM Y-STRs, using the previously published 14 RM Y-STRs (Ballantyne et al., 2010. Ibid; Ballantyne et al., 2012. Forensic Science Int Genet 6: 208-218; Claerhout et al., 2018. Forensic Science Int: Genetics 34: 1-10) and the newly developed mutability score used in the novel in silico approach. As evident, RM Y-STRs can be clearly differentiated from non-RM Y-STRs based on the mutability prediction score. This finding implies that the in silico approach, which uses the mutability prediction score, is suitable for finding novel RM Y-STR candidate markers.

Figure 3:
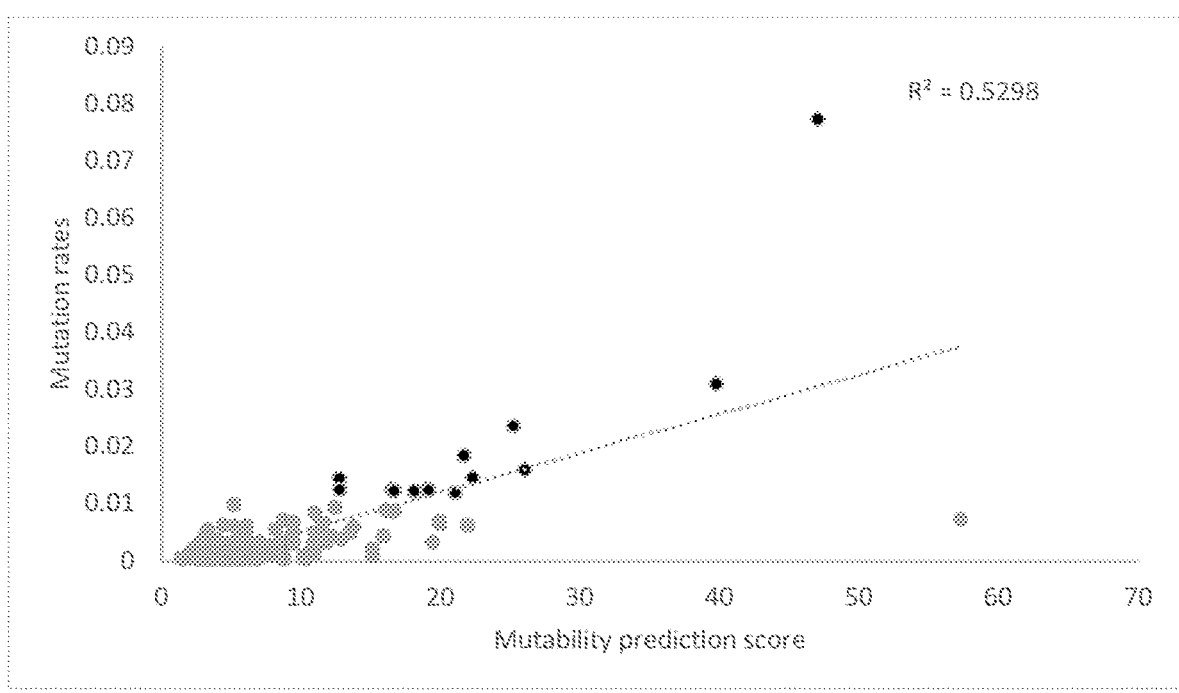

In FIG. 3 a statistically significant positive correlation (P-value $<2.2\times10^{-16}$) between the newly developed mutability prediction score and the observed mutation rate of 185 previously known Y-STRs is shown. The Y-axis indicates the previously described mutation rates of the Y-STR markers and on the X-axis their mutability prediction score is shown. As evident, the previously known RM Y-STRs (black dots) appear with increased mutation rates and increased mutability prediction scores. This finding implies that the in silico approach, which uses the mutability prediction score, is suitable for finding novel RM Y-STR candidate markers.

FIG. 4 displays the nucleic acid sequences and locations of the newly identified RM Y-STR markers and fast mutating (FM) Y-STR markers according to the Y-chromosome reference sequence of the GRCh38 reference genome. Sequences used for PCR amplification are indicated in bold.

Figure 5:
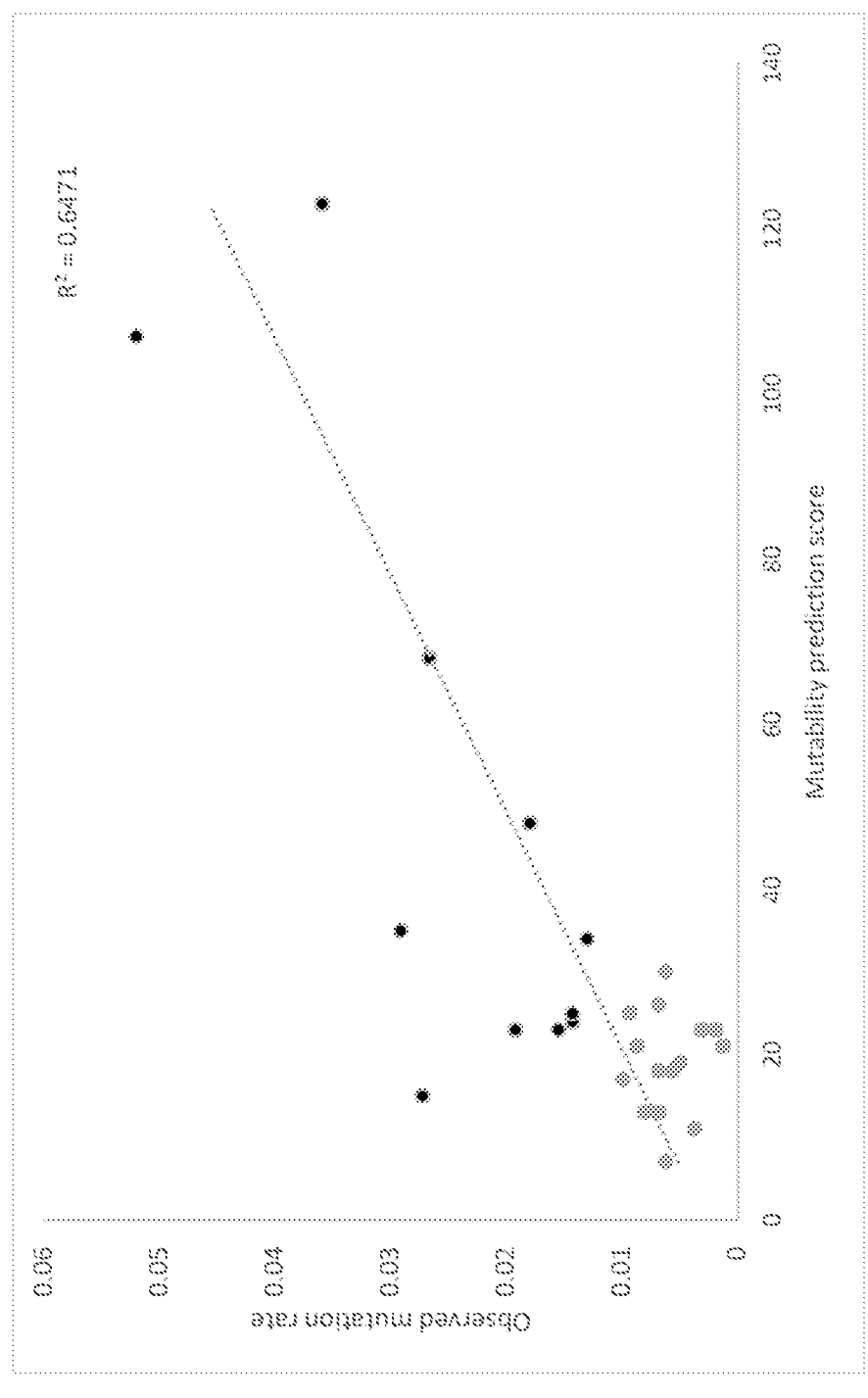

FIG. 5 shows the correlation between empirically derived mutation rates (Y axis) and the mutability prediction scores (X-axis) for the 27 candidate RM Y-STR markers that were identified with the in silico approach, and for which mutation rates were estimated from a large number of genotyped father-son pairs. As evident, the novel RM Y-STRs (black dots) appear with increased mutation rates and increased mutability prediction scores. This finding demonstrates that the in silico approach, which uses the mutability prediction score, is able to find novel RM Y-STR markers confirmed by empirical mutation rate estimation.

Figure 6:
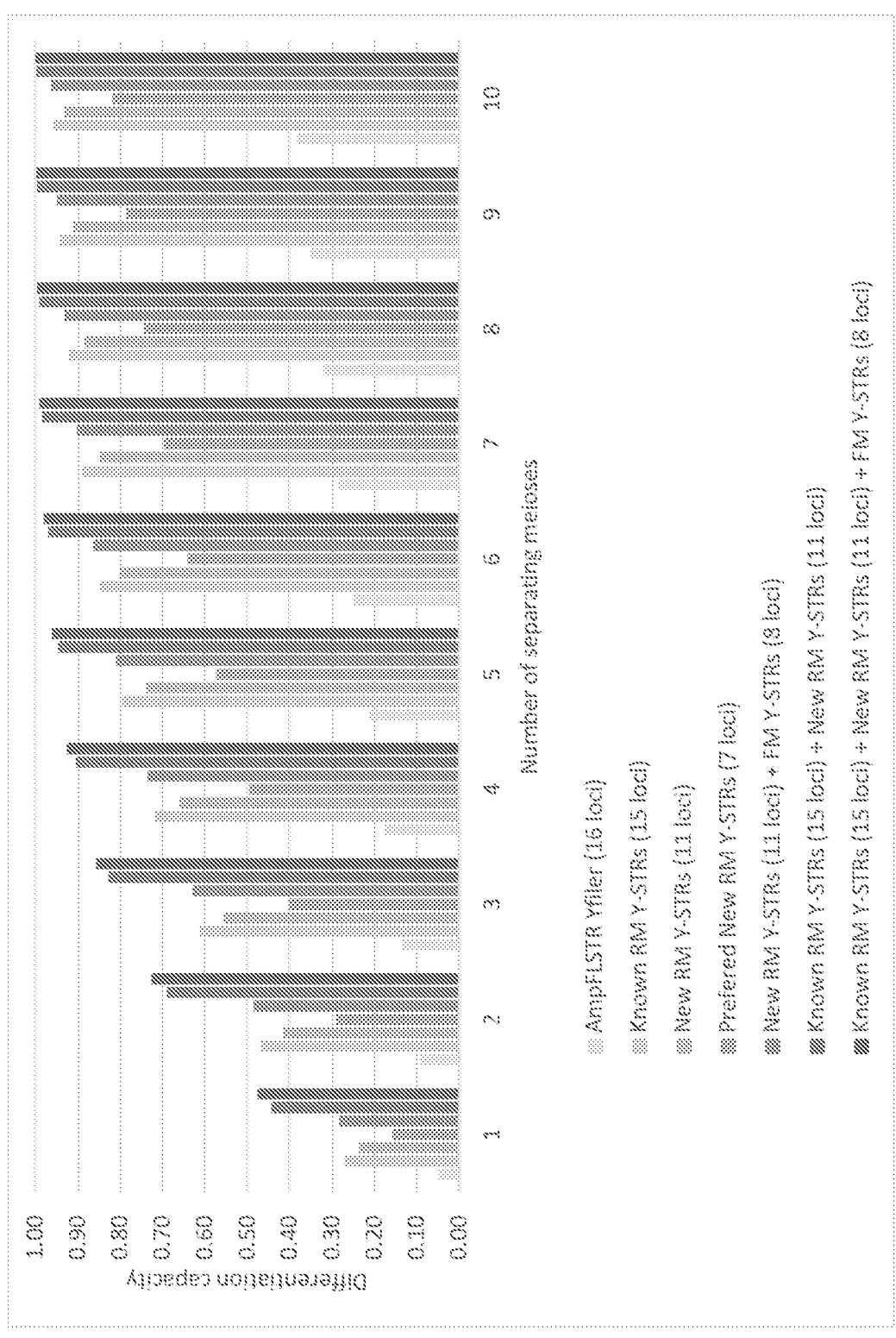

FIG. 6 exhibits the male relative differentiation capacities estimated for closely and distantly paternally related males, using different sets of previously known and newly identified Y-STRs, including standard Y-STRs used in forensic genetics (AmpFLSTR Yfiler (mutation rate ~$10^{-3}$), previously known RM Y-STRs ($>10^{-2}$), novel RM Y-STRs ($>10^{-2}$) and novel fast mutating (FM) Y-STRs (mutation rate between $5\times10^{-3}$ and $10^{-2}$). These differentiation capacities were estimated from the locus specific mutation rate estimates empirically derived from genotyping a large number of father-son pairs. These differentiation capacities provide theoretical expectations on male relative differentiation.

Figure 7:
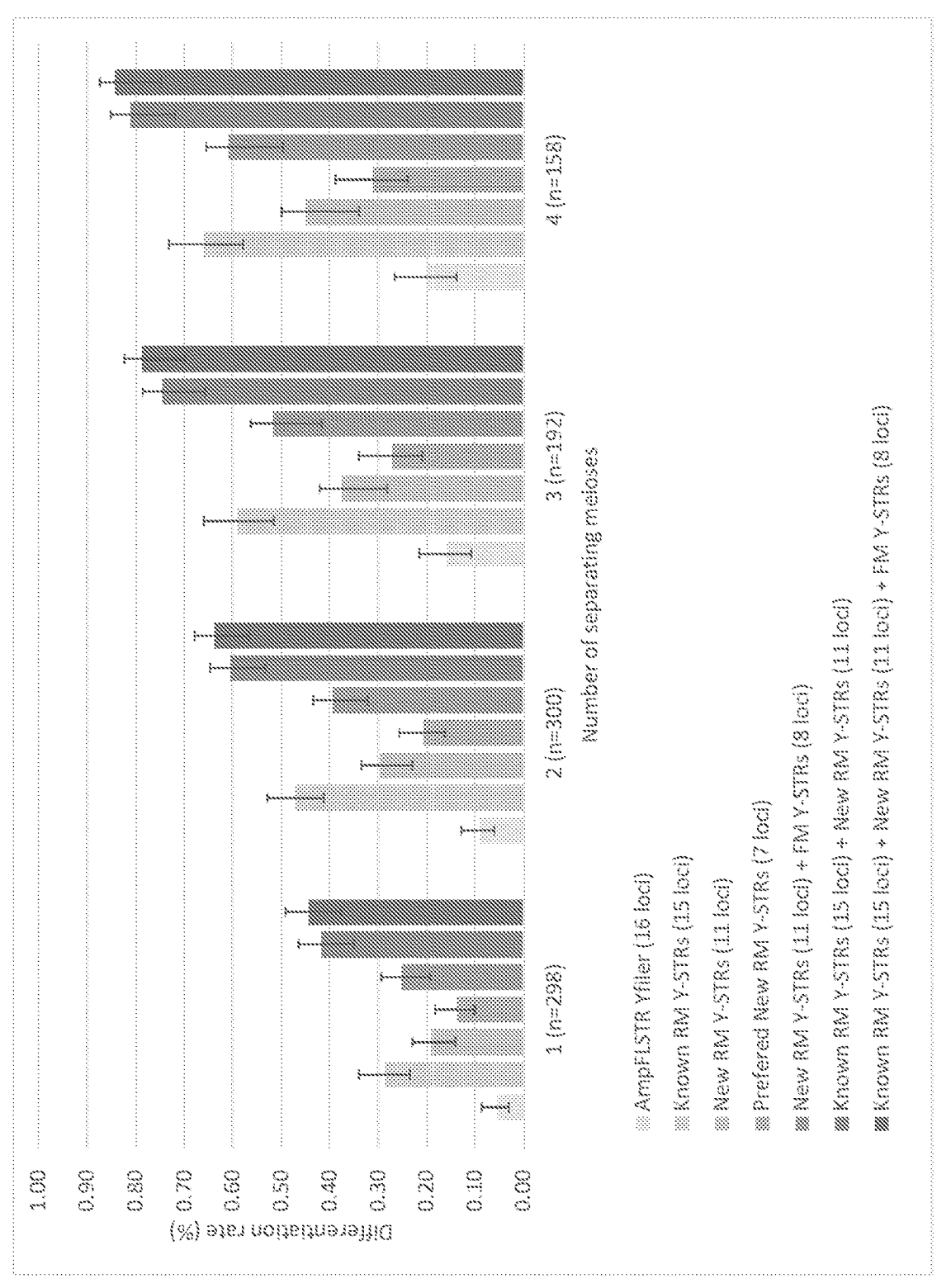

FIG. 7 shows the male relative differentiation rates estimates for closely paternally related males, using different sets of previously known and newly identified Y-STRs, including standard Y-STRs used in forensic genetics (AmpFLSTR Yfiler), previously known RM Y-STRs, novel RM Y-STRs and novel fast mutating (FM) Y-STRs. These male relative differentiation rates were estimated from independent male relatives not used for mutation rate estimation and thus provide empirically derived male relative differentiation rates.

Figure 8:
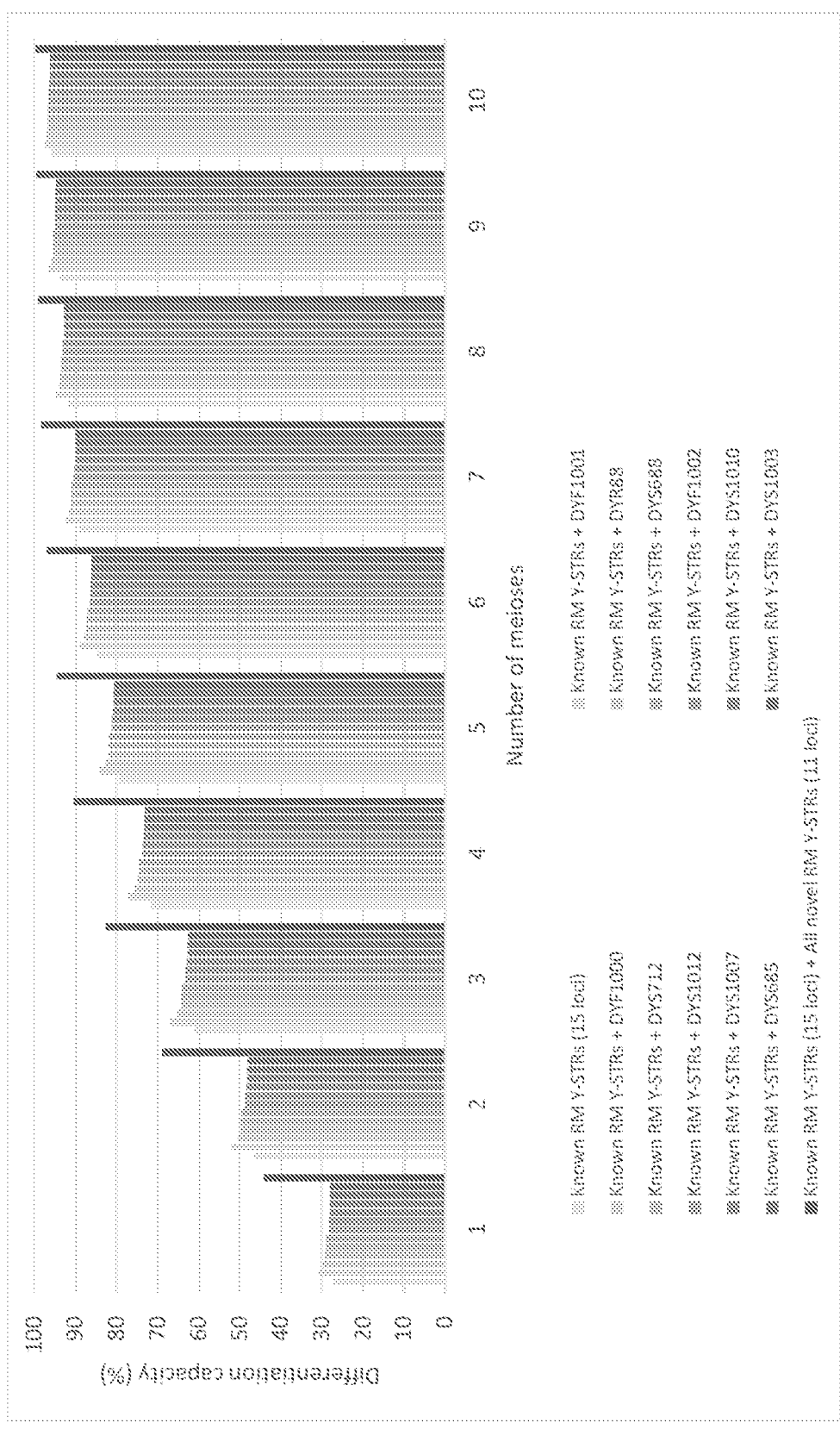

FIG. 8 shows that each of the 11 novel RM Y-STRs, when used as single marker in combination with the 15 previously known RM Y-STRs, increases male relative differentiation capacities relative to the 15 previously known RM Y-STRs alone. This figure also shows that when combing all novel and previously known RM Y-STRs there is a large increase in discrimination capacities over previous knowledge.

Figure 9:
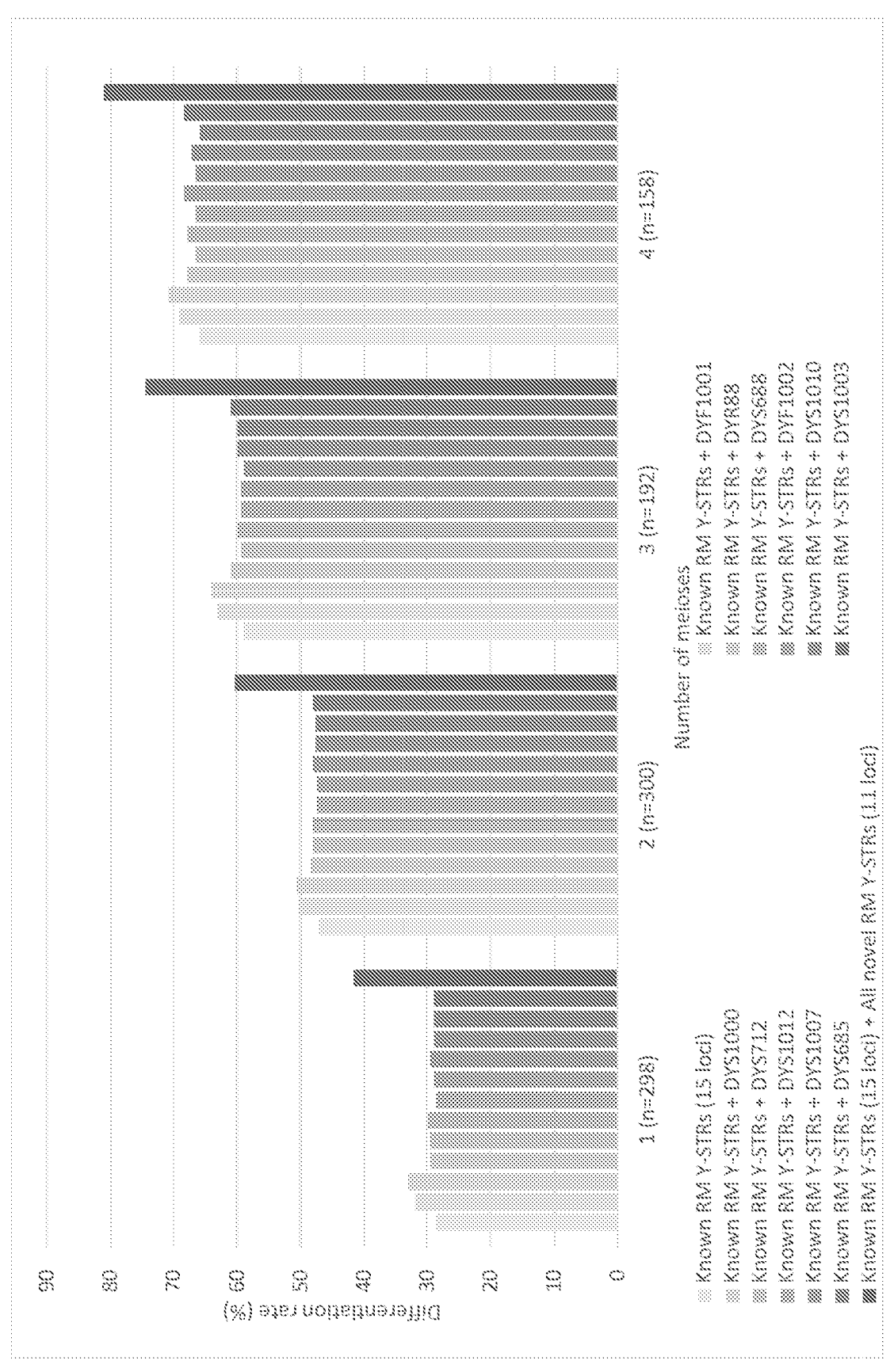

FIG. 9 shows that each of the 11 novel RM Y-STRs, when used as single marker in combination with the 15 previously known RM Y-STRs, increases male relative differentiation rates relative to the 15 previously known RM Y-STRs alone. This figure also shows empirically that when combining all novel and previously known RM Y-STRs there is a large increase in discrimination rates over previous knowledge.

Figure 10:
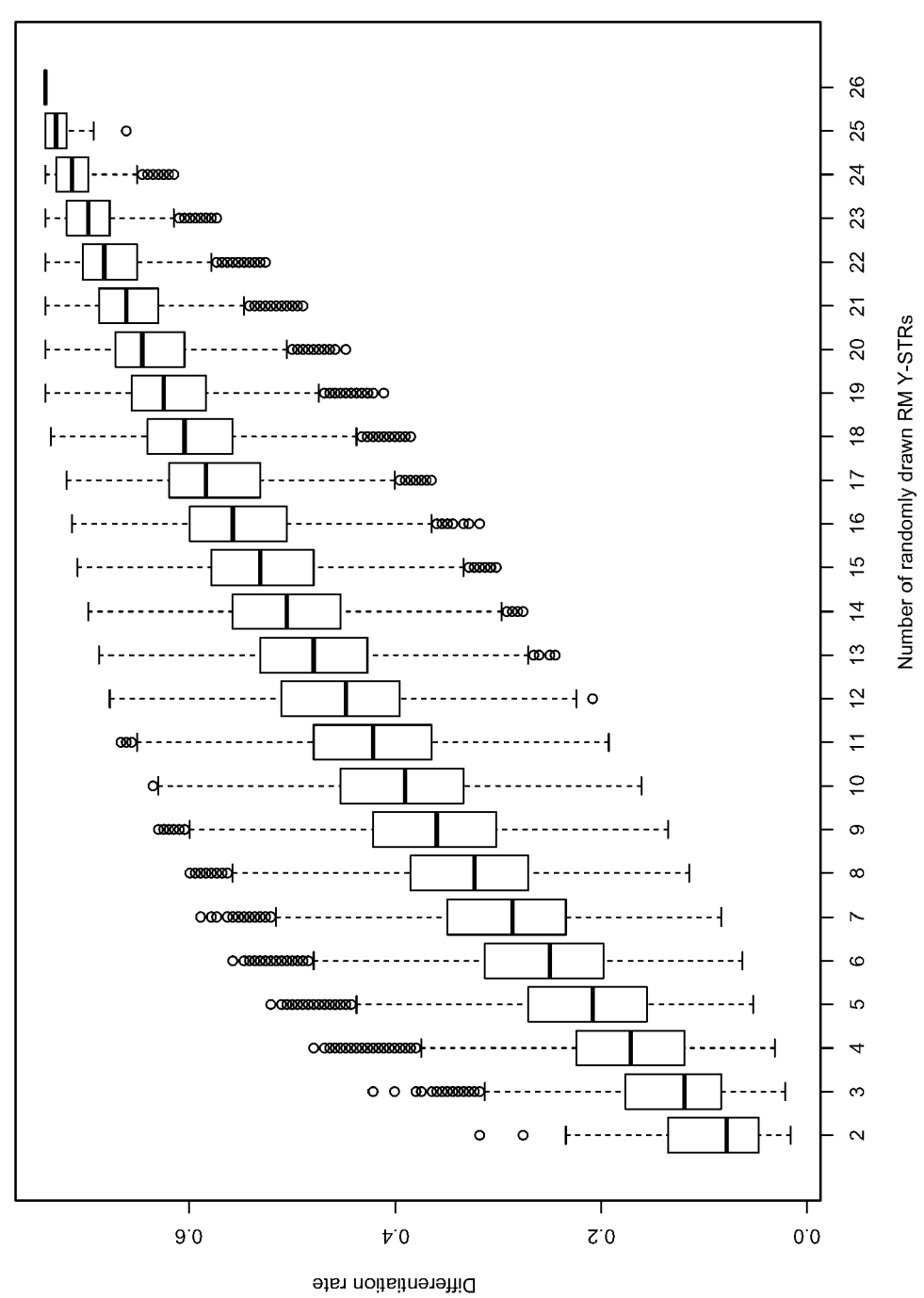

FIG. 10 shows the distribution of differentiation rates as a result of testing with between two to twenty-six randomly combined RM Y-STR markers. These distributions were obtained by making one hundred thousand random combinations for each number of markers selected from all twenty-six RM Y-STRs, while providing that at least one of the RM Y-STRs originated from the group consisting of DYF1000, DYF1001, DYF1002, DYS1003, DYS1007, DYS1010 and DYS1012. The figure shows that at least nine RM Y-STRs are needed to achieve a differentiation rate of more than 60% in pairs of males that are separated by three generations; when combining a total of eighteen RM Y-STRs, more than half of the combinations reached a differentiation rate surpassing 60%; when combining 24 RM Y-STRs all combinations resulted in a differentiation rate greater than 60%.

Figure 11:
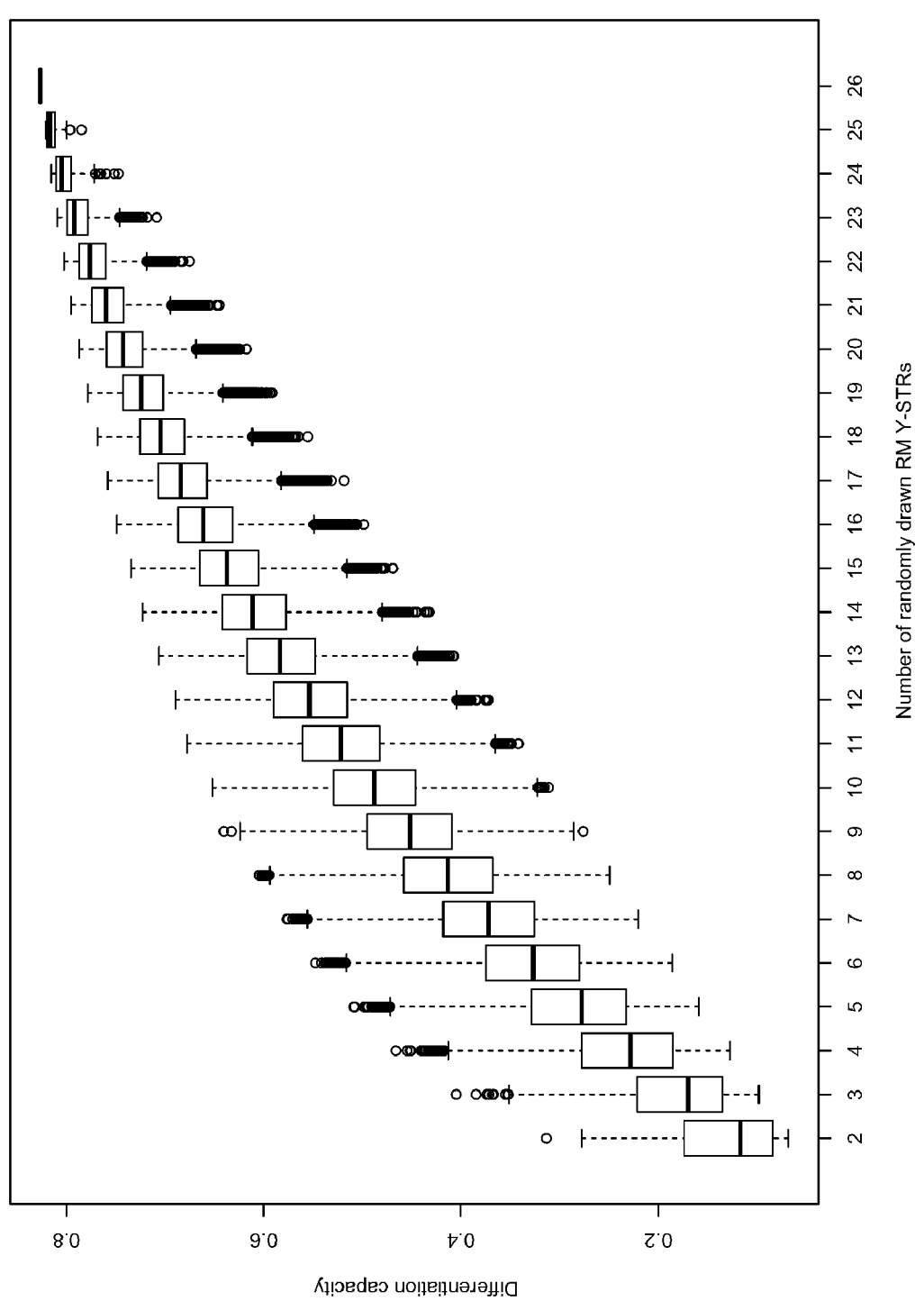

FIG. 11 shows the distribution of differentiation capacities as a result of the number of combined RM Y-STR markers ranging from two to twenty-six. These distributions were obtained by making one hundred thousand random combinations for each number of markers, while providing that at least one of the RM Y-STRs originated from the group consisting of DYF1000, DYF1001, DYF1002, DYS1003, DYS1007, DYS1010 and DYS1012. The figure shows that at least nine RM Y-STRs are needed to achieve a differentiation capacity of more than 62% in pairs of males that are separated by three generations; when combining a total of fifteen RM Y-STRs, more than half of the combinations reached a differentiation capacity surpassing 62%; when combining twenty one RM Y-STRs all combinations resulted in a differentiation capacity greater than 62%.

DETAILED DESCRIPTION

When referring to a noun (e.g. a compound, an additive) in the singular, the plural is meant to be included, or it follows from the context that it should refer to the singular only. The term "a" or "an" as used herein is defined as "at least one" unless specified otherwise, or it follows from the context that it should refer to the singular only.

A "short tandem repeat (STR)" refers to a region of genomic DNA that contains short, repetitive sequence elements (or sequence units), which are generally two to seven base pairs in length and are repeated at least once within an STR in a tandem like fashion to form stretches of repetitive DNA sequences (i.e. STR).

The term "Y-chromosomal short tandem repeat marker (Y-STR marker)" as used herein refers to an STR marker that is present in the non-recombining part of the human Y chromosome and carries information about the identity of the male subject carrying the marker. This information is materialized upon amplification of the Y-STR marker, thereby forming one or more amplicons. Analysis of said one or more amplicons, preferably by comparison of the one or more amplicons formed by the amplification of the Y-STR marker of one male to the amplicons formed by the amplification of the same Y-STR marker of another male, in particular a closely related male, is what constitutes a marker. Hence the term "Y-STR marker" as used herein not merely refers to information, but also inherently includes the use of said information to characterize an individual carrying said marker. An Y-STR marker is male specific, either because it only exists in DNA from males, or amplification preferentially or exclusively detects the Y-chromosomal copy, but not an X-chromosomal copy in cases were the Y-STR is located in a Y-chromosome region with homology to an X-chromosomal region but outside the pseudo-autosomal regions of the Y-chromosome.

A "group of Y-STR markers" refers to a combination of at least two Y-STR markers. In the context of the present invention, said group of Y-STR markers comprises at least one RM Y-STR marker selected from the group consisting of DYF1000, DYF1001, DYF1002, DYS1003, DYS1007, DYS1010 and DYS1012. Further, the group of Y-STR markers may comprise one or more RM Y-STR markers selected from the group consisting of DYR88, DYS685, DYS688, DYS712, DYF387S1, DYF399S1, DYF403S1A, DYF403S1B, DYF404S1, DYS449, DYS518, DYS526, DYS547, DYS570, DYS576, DYS612, DYS626, DYS627 and DYS724 and/or one or more FM markers selected from the group consisting of DYS1013, DYS1016, DYS1017, DYS1009, DYS1014, DYF1004, DYS1005, and DYS1006.

A "mutation" in a Y-STR marker is an allelic change in, for example, the number of repeats leading to a change in the length and/or composition of the repeat region of an Y-STR marker. In the context of this invention, this allelic change is observed and confirmed by independent genotyping, for example between male relatives e.g. father and his son. These mutations are used to differentiate male individuals.

A "rapidly mutating Y-chromosomal short tandem repeat" (RM Y-STR) marker is a Y-STR marker that has a substantially higher mutation rate than regular Y-STR markers. RM Y-STR markers in the present context are characterized by a mutation rate p in the order of $10^{-2}$ or higher, i.e. at least one mutation per one hundred meiosis per Y-STR marker. This mutation rate is approximately ten-fold higher than that of standard Y-STRs used in forensics nowadays.

Furthermore, a "fast mutating Y-chromosomal short tandem repeat" (FM Y-STR) marker is a Y-STR marker that has a mutation rate which is lower than RM Y-STR markers, but is significantly higher than regular Y-STR markers. Thus, the mutation rate p is between $5.0 \times 10^{-3}$ (i.e. five mutations per one thousand meiosis per Y-STR marker) and $1 \times 10^{-2}$ (i.e. one mutation per one hundred meiosis per Y-STR marker). As is known to a person skilled in the art, the mutation rate per Y-STR may be estimated, for example, empirically from direct observations in a large number of DNA-confirmed father son pairs, by dividing the number of mutations observed by the total number of father and son pairs tested per each Y-STR marker.

As used herein the markers "DYF403S1A" and "DYF403S1B" are referred to as two individual markers. Said markers have a different mutation rate. Said markers may be materialized upon amplification using the same primers. However, upon amplification different amplicons for "DYF403S1A" and "DYF403S1B" are formed, which may be analysed individually.

In the present context, a "male" is a subject carrying a Y chromosome. Preferably, the male is mammal, in particular a human.

Furthermore, with "male relatives" or "paternally related men" is meant a group of closely or distantly related male individuals that are paternally related via one to a few meioses, tracing back to the same paternal male ancestor. In said male relatives, non-recombining parts of the Y-chromosomal DNA have been transferred strictly from biological fathers to their sons. In general, closely related men are separated by 1 (father-son), 2 (brothers, grandfather-grandsons), 3 (e.g. uncle-nephews), or 4 meioses (e.g. male cousins), whereas distantly related men are separated by 5-10 meiosis.

The term "paternal lineage", as is used herein, refers to a line of males that share the same male ancestor in the paternal part of the family or pedigree, which may go back a few or many generations, and wherein non-recombining parts of the Y-chromosomal DNA have been transferred strictly from biological fathers to their sons. Members of the same paternal lineage include close and distant relatives (see before) but also other paternally related men that are separated by a large number of meioses, often so many that such paternal relationship is typically absent from family records. Although belonging to the same paternal lineage means that these males are remotely paternally related, they are generally considered as unrelated men prior to Y-chromosome analyses showing that they belong to the same paternal lineage.

The term "allele", as is used herein, refers to a variation of a DNA segment (or individual genetic locus) occupying the same locus of a chromosome.

Herein, a "locus" as is used herein refers to the physical position within the DNA on a chromosome.

The term "marker", as is used herein, refers to a short tandem repeat sequence that is present in a single locus, at multiple positions within the same locus, or at multiple positions on different loci, which carries information about the biological state, biological condition or identity of a subject carrying the marker. Said short tandem repeat can be amplified, preferably with a single primer or set of primers. The information is materialized upon amplification of the marker thereby forming one or more amplicons. Subsequent analysis of the formed amplicons, preferably by comparing to a reference, is what constitutes the marker. Hence the term "marker" as used herein not merely refers to information, but also inherently includes the use of said information to characterize an individual carrying said marker.

The term "male relative differentiation capacity", as is used herein, refers to the percentage of closely or distantly paternally related males that is distinguished from one another by at least one Y-STR mutation and is estimated by using the empirically derived mutation rates for one or more of the Y-STR markers analyzed. As such, male differentiation capacity provides a theoretical expectation, derived from empirically obtained mutation rates, on male relative differentiation.

The term "male relative differentiation rate", as is used herein, refers to the percentage of closely or distantly paternally related males that is distinguished from one another by at least one Y-STR mutation and is estimated from empirical testing of DNA-confirmed male relatives of different degrees (i.e. separating number of meioses) for one or more of the Y-STR markers analyzed. As such, male relative differentiation rates provide the empirical conformation of the expectations raised by the male relative differentiation capacity.

The term "typing", as used herein, refers to the differentiation, or contribution to differentiation, of one male from a group of males that are paternally related. Said males may be closely, distantly or remotely related, and thus belong to the same paternal lineage, which can be differentiated by Y-chromosome analysis into different paternal "sub-lineages". Moreover, "typing" may also refer to the differentiation, or assist in the differentiation, of one male from a group of paternally unrelated males, who thus belong to different paternal lineage, which can be differentiated by Y-chromosome analysis.

The term "amplification", as is used herein, refers to the in vitro amplification of a specific nucleic acid sequence. In vitro amplification methods include amplification of a target nucleic acid sequence using, for example, ligase chain reaction (LCR), isothermal ribonucleic acid amplification such as nucleic acid sequence-based amplification (NASBA) and cleavage-based signal amplification of RNA, transcription mediated amplification, strand displacement amplification and, preferably, polymerase chain reaction (PCR).

The term "PCR reaction", as is used herein, refers to an amplification reaction that is characterized by repeated cycles of denaturation of target nucleic acid template, annealing of primers, and extension (synthesis) of new nucleic acid strand. The specificity of a PCR reaction is substantially determined by the % identity of the primers to the target nucleic acid template and the annealing temperature.

The term "multiplex PCR assay", as is used herein, refers to the simultaneous amplification of different nucleic acid fragments in a single amplification reaction.

The terms "forward primer" and "reverse primer", as are used herein, refer to a single-stranded oligonucleotide or oligonucleotide mimic of 15-50 bases, preferably 16-30 bases, that is complementary to nucleic acid sequences flanking the region to be amplified. The sequence of the forward primer and reverse primer determine the specificity of the amplification reaction. Preferred primers are preferably about 100% identical to a region on a target nucleic acid template such that only the region between two primers in a target nucleic acid template is amplified. The distance between the primer binding sites on the target nucleic acid template will determine the size of the amplified product.

The term "amplicon", as is used herein, refers to a region on a target nucleic acid template that is amplified. Said amplification preferably involves two primers, preferably a forward primer and a reverse primer.

The term "detectable label", as is used herein, refers to a label that is detectable by spectroscopic, photochemical, biochemical, immunochemical, or chemical means. For example, useful labels include radioactive labels, fluorescent labels, electron-dense reagents, enzymes (as commonly used in ELISAs), biotin, or haptens and proteins for which antisera or monoclonal antibodies are available.

The term "sequencing", as used herein, refers to the analysis of the nucleotide sequence of a nucleic acid molecule. The term includes reference to the analysis of every single base or base pair in a nucleic acid molecule, either within an amplicon or in non-amplified DNA. Sequencing may be performed using different sequencing technologies, comprising both classical DNA sequencing technologies, such as Sanger sequencing and Maxam and Gilbert sequencing, as well as next generation sequencing (also referred to as massively parallel sequencing) technologies, such as Ion Torrent sequencing and Illumina sequencing, and third generation sequencing technologies such as Nanopore sequencing and PacBio® sequencing etc.

The invention provides a group of Y-chromosomal short tandem repeat (Y-STR) markers comprising at least one RM Y-STR marker selected from the group consisting of DYF1000, DYF1001, DYF1002, DYR88, DYS685, DYS688, DYS712, DYS1003, DYS1007, DYS1010 and DYS1012, preferably at least one RM Y-STR marker selected from the group consisting of DYF1000, DYF1001, DYF1002, DYS1003, DYS1007, DYS1010 and DYS1012.

Furthermore, the inventors have also identified a group of Y-STR markers that are not characterized as RM Y-STR markers, but still have a mutation rate that is significantly higher than the mutation rate of regular Y-STR markers. These Y-STR markers, termed fast mutating (FM) Y-STR markers, can contribute to distinguishing males relatives, albeit to a lesser extent than RM Y-STR markers (because their mutation rate is lower), but better than regular Y-STRs (because their mutation rate is higher). Thus, the invention also relates to a group of Y-STR markers comprising at least one, preferably at least two, more preferably at least three, most preferably all FM Y-STR markers selected from the group consisting of DYS1013, DYS1016, DYS1017, DYS1009, DYS1014, DYF1004, DYS1005, and DYS1006.

Mutation rates are calculated by dividing the observed number of mutations in a FM Y-STR and/or RM Y-STR marker of which the mutation rate is to be determined by the total number of male relative pairs (e.g. father son pairs) being analysed. The mutation rate is most accurate if a large number of male relative pairs (e.g. father son pairs) is analyzed, preferably at least 1000 male relative pairs, such as father-son pairs, more preferably at least 1250 male relative pairs, in particular at least 1500 male relative pairs. The number of male relative pairs needed to obtain reliable mutation rates depend on the expected mutation rate of the Y-STR analysed. For example for RM Y-STRs that have an expected mutation rate $>10^{-2}$, about 1000 father-son pairs are needed to find at least 10 mutations. The lower the mutation rate of a Y-STR is the more father son pairs are needed to find enough mutations to obtain reliable mutation rate estimates.

In particular, the invention relates to a group of Y-chromosomal short tandem repeat (Y-STR) markers comprising at least one RM Y-STR marker selected from the group consisting of DYF1000, DYF1001, DYF1002, DYR88, DYS685, DYS688, DYS712, DYS1003, DYS1007, DYS1010 and DYS1012, at least one fast mutating (FM) Y-STR marker selected from the group consisting of DYS1013, DYS1016, DYS1017, DYS1009, DYS1014, DYF1004, DYS1005, and DYS1006 or comprising a combination thereof.

With this set of RM Y-STR markers and/or FM Y-STR markers a markedly improved differentiation rate and/or differentiation capacity of closely related males can be achieved compared to known methods for differentiating between male relatives. The current state of the art allows a differentiation rate of paternally related men of 27% for male relatives separated by 1 meiosis, 46% (separated by two meioses), 54% (three meioses) or 62% (four meioses) by observed mutations in a set of thirteen RM Y-STRs (Adnan et al., 2016. Ibid). Commercially available Y-STR PCR amplification kits, such as the widely used Yfiler™ kit, developed for differentiating paternal lineages (i.e., unrelated males from different paternal lineages), but not for differentiating male relatives, allow respectively 5%, 11%, 17% and 25% discrimination of males related by one to four generations (Adnan et al., 2016. Ibid).

FIG. 7 shows, for the first time, the rates based on the combination of 15 known RM Y-STR markers. These 15 RM Y-STR markers include the 14 RM Y-STR markers previously published (Ballantyne et al., 2010. Ibid; Ballantyne et al., 2012. Ibid), and one additional Y-STR recently reported with increased mutation rate (Claerhout et al., 2018. Forensic Science Int: Genetics 34: 1-10) that allow classifying it as RM Y-STR. Thus, currently, only a limited number of paternally related males, particularly closely related ones, can be differentiated from one another based on the current knowledge, i.e., using known regular Y-STR markers as well as RM Y-STR markers.

As shown in FIGS. 8 and 9, each of the novel RM Y-STR markers described herein improves the male relative differentiation capacities (FIG. 8) and the male relative differentiation rates (FIG. 9) of the set of 15 previously known RM Y-STR markers, when being combined with them, compared to the capacity and rates achieved solely by the 15 known RM Y-STRs combined.

Moreover, with the present group of Y-STR markers, comprising at least one novel RM Y-STR marker, such as two novel RM Y-STR markers, three novel RM Y-STR markers, four novel RM Y-STR markers, five novel RM Y-STR markers, six novel RM Y-STR markers or seven novel RM Y-STR markers, eight novel RM Y-STR markers, nine novel RM Y-STR markers, ten novel RM Y-STR markers, eleven novel RM Y-STR markers and/or at least one FM Y-STR marker, such as at least two FM Y-STR markers, at least three FM Y-STR markers, at least four FM Y-STR markers, at least five FM Y-STR markers, at least six FM Y-STR markers, at least seven FM Y-STR markers or at least eight FM Y-STR markers, according to the invention, the differentiation rates and/or differentiation capacity of known methods for distinguishing males can be markedly improved, allowing to differentiate a larger number of paternally related males. The male relative differentiation rate and/or differentiation capacity is correlated with the mutation rate of FM Y-STR and/or RM Y-STR markers and the number of FM Y-STR and/or RM Y-STR markers that are analyzed. Thus, the higher the mutation rate of the markers and the more RM Y-STR and FM Y-STR markers are analyzed, the higher the male relative differentiation rate and differentiation capacity. This is because the likelihood of differentiating a given pair of paternally related men e.g. a father and his son by the occurrence of a mutation during transmission of Y-chromosomal DNA from father to son is statistically increased, the higher the natural mutation rate of the Y-STR marker is and the more Y-STR marker with increased mutation rates (i.e. FM Y-STR and/or RM Y-STRs) are analysed. As is clear from FIGS. 6 and 7, adding the novel RM Y-STR markers DYF1000, DYF1001, DYF1002, DYR88, DYS685, DYS688, DYS712, DYS1003, DYS1007, DYS1010, and DYS1012; preferably DYF1000, DYF1001, DYF1002, DYS1003, DYS1007, DYS1010 and DYS1012, and/or novel FM Y-STR markers DYS1013, DYS1016, DYS1017, DYS1009, DYS1014, DYF1004, DYS1005, and DYS1006, or of a combination thereof, to the 15 known RM Y-STR markers increases the male relative differentiation capacities and rates, respectively. The highest differentiation rate and/or differentiation capacity is obtained when a maximum number of available RM Y-STR and FM Y-STR markers are analyzed, as the skilled person will understand.

Therefore, the group of Y-STR markers according to the invention, preferably comprises at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, most preferably thirty-four Y-STR markers.

Preferably, the invention is directed to a group of Y-STR markers comprising at least one RM Y-STR marker selected from the group consisting of DYF1000, DYF1001, DYF1002, DYR88, DYS685, DYS688, DYS712, DYS1003, DYS1007, DYS1010 and DYS1012, at least one FM Y-STR marker selected from the group consisting of DYS1013, DYS1016, DYS1017, DYS1009, DYS1014, DYF1004, DYS1005, DYS1006, or a combination thereof. Each of these markers, or combination of markers, preferably improves the differentiation rate and/or the differentiation capacity of the group of 15 known RM Y-STR markers.

Said group of Y-STR markers, comprising at least one RM Y-STR marker selected from the group consisting of DYF1000, DYF1001, DYF1002, DYR88, DYS685, DYS688, DYS712, DYS1003, DYS1007, DYS1010 and DYS1012, at least one FM Y-STR marker selected from the group consisting of DYS1013, DYS1016, DYS1017, DYS1009, DYS1014, DYF1004, DYS1005, and DYS1006, or a combination thereof, preferably a group of Y-STR markers comprising at least one RM Y-STR marker selected from the group consisting of DYF1000, DYF1001, DYF1002, DYS1003, DYS1007, DYS1010 and DYS1012, preferably has a rate of differentiating two males paternally related by one generation of at least 30%, more preferably at least 31%, even more preferably at least 32%, 33%, 34%, or even 35%. Furthermore, the group preferably has a rate of differentiating two males paternally related by two generations of at least 48%, more preferably at least 49%, even more preferably at least 50%, at least 51%, at least 52%, at least 53%. The group preferably has a differentiation rate of distinguishing males paternally related by three generations of at least 60%, more preferably at least 61%, even more preferably at least 62%, at least 63%, at least 64%, at least 65%. Moreover, the group of RM Y-STR markers preferably has a differentiation rate of distinguishing two males paternally related by four generations of at least 67%, more preferably at least 68%, even more preferably at least 69%, most preferably at least 70%, at least 71%, at least 72%, at least 73%, at least 74%.

Said differentiation rate is preferably obtained in a data set containing 192 pairs of males from Pakistani descent. As the skilled person will understand, a differentiation rate of a group of Y-STR markers estimated by empirically testing of DNA-confirmed male relatives from a first data set may vary slightly from the differentiation rate estimated by empirically testing of DNA-confirmed male relatives from a second data set.

Without wishing to be bound by any theory, it is believed that such variations may be caused by differences in size of the data set, i.e. total number of male pairs comprised in the first data set compared to the second data set, or by demographic differences, such as differences in race, between the male pairs comprised in the first and second data sets. Furthermore there are stochastic effects that may cause variations in differentiation rates between datasets.

For good comparison, a differentiation rate of a group of Y-STR markers according to the invention is preferably estimated by empirical testing of DNA-confirmed male relatives comprised in the same data set. Preferably said data set which is used to estimate a differentiation rate comprises a substantial number of male relative pairs, preferably at least 50 male relative pairs, more preferably at least 100 pairs of male relative pairs, more preferably at least 150 male relative pairs, in particular at least 190 male relative pairs. It is believed that more accurate differentiation rates may be estimated when using a data set comprising a larger number of male pairs.

Said group of Y-STR markers, comprising at least one RM Y-STR marker selected from the group consisting of DYF1000, DYF1001, DYF1002, DYR88, DYS685, DYS688, DYS712, DYS1003, DYS1007, DYS1010 and DYS1012, at least one FM Y-STR marker selected from the group consisting of DYS1013, DYS1016, DYS1017, DYS1009, DYS1014, DYF1004, DYS1005, and DYS1006, or a combination thereof, preferably a group of Y-STR markers comprising at least one RM Y-STR marker selected from the group consisting of DYF1000, DYF1001, DYF1002, DYS1003, DYS1007, DYS1010 and DYS1012, preferably has a capacity of differentiating two males paternally related by one generation of at least 28%, more preferably at least 29%, even more preferably at least 30%, 31%, 32%, or even 33%. Furthermore, the group preferably has a rate of differentiating two males paternally related by two generations of at least 48%, more preferably at least 49%, even more preferably at least 50%, at least 51%, at least 52%, at least 53%. The group preferably has a differentiation capacity of distinguishing males paternally related by three generations of at least 62%, more preferably at least 63%, even more preferably at least 64%, at least 65%, at least 66%, at least 67%. Moreover, the group of RM Y-STR markers preferably has a differentiation capacity of distinguishing two males paternally related by four generations of at least 73%, more preferably at least 74%, even more preferably at least 75%, most preferably at least 76%, at least 77%, at least 78%, at least 79%, at least 80%.

Preferably, the group of Y-STR markers, comprising at least one RM Y-STR marker selected from the group consisting of DYF1000, DYF1001, DYF1002, DYR88, DYS685, DYS688, DYS712, DYS1003, DYS1007, DYS1010 and DYS1012, preferably at least one RM Y-STR marker selected from the group consisting of DYF1000, DYF1001, DYF1002, DYS1003, DYS1007, DYS1010 and DYS1012, comprises at least nine RM Y-STR markers. It was found that with a set of at least nine RM Y-STR markers, comprising at least one RM Y-STR marker selected from the group consisting of DYF1000, DYF1001, DYF1002, DYS1003, DYS1007, DYS1010 and DYS1012, a differentiation rate of at least 60% and/or a differentiation capacity of at least 62% in pairs of males that are separated by three generations could be achieved. This differentiation rate and differentiation capacity are higher than the differentiation rate of 59% and differentiation capacity of 61% that could be achieved with the group of fifteen known RM Y-STR markers described, whilst the number of Y-STR markers comprised in the group is lower. (Ballantyne et al., 2014. Human Mutation 35: 1021-1032; Claerhout et al., 2018. Forensic Science Int: Genetics 34: 1-10). This means that a higher percentage of paternally related males separated by three generations may be distinguished from one another, compared to when the group of fifteen known RM Y-STR markers is used. In addition, fewer markers need to be analyzed, thereby markedly improving the efficiency of analysis in terms of time, materials and costs required to perform said analysis. Said differentiation rates have been empirically derived using the same dataset comprising 192 Pakistani male relatives.

Examples of groups of RM Y-STR markers comprising nine RM Y-STR markers that achieve a differentiation rate of at least 60%, or a differentiation capacity of at least 62% are shown in Tables 4 and 5, respectively. Hence, the invention further relates to the groups of Y-STR markers as shown in Table 4 and Table 5.

It was found that the same markers were present in each group of nine RM Y-STR markers according to the invention that were found to achieve a differentiation rate of at least 60%. Therefore, the invention further relates to a group of Y-STR markers, comprising at least nine, preferably at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, at least twenty five, at least twenty six RM Y-STR markers, comprising at least the RM Y-STR markers DYF1000, DYF399S1 and DYS724, more preferably at least the RM Y-STR markers DYF1000, DYF399S1, DYS724 and DYF1001, even more preferably at least the RM Y-STR markers DYF1000, DYF399S1, DYS724, DYS612 and DYF1001. With such a group of Y-STR markers a differentiation rate that is higher than described in the art may be achieved.

Said group of nine or more Y-STR markers, comprising at least the markers DYF1000, DYS399S1 and DYS724, may further be used to achieve a differentiation capacity of at least 62% in pairs of males that are separated by three generations. In addition to these three markers, two further markers were identified to be present in each group of nine RM Y-STR markers according to the invention, that achieves a differentiation capacity of at least 62%. Accordingly, the invention further preferably relates to a group of Y-STR markers, comprising at least nine, preferably at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, at least twenty five, at least twenty six RM Y-STR markers, comprising at least the RM Y-STR markers DYF1000, DYF399S1, DYS724, DYS688 and DYS1001, preferably comprising at least the RM Y-STR markers DYF 1000, DYF399S1, DYS724, DYS688 and DYS1001, and at least one, at least two, or three RM Y-STR marker selected from the group consisting of DYS712, DYR88 and DYF403S1a. With such a group of Y-STR markers a differentiation capacity that is higher than described in the art may be achieved.

A skilled person is capable of determining the differentiation capacity and estimating the differentiation rate of a group of Y-STR markers according to the invention in terms of differentiating males paternally related by one, two, three or four generations, based on the mutation rates of the individual markers comprised in the group of Y-STR markers according to the invention.

The invention also provides a group of Y-STR markers including one or more RM Y-STR markers selected from the group consisting of DYF387S1, DYF399S1, DYF403S1A, DYF403S1B, DYF404S1, DYS449, DYS518, DYS526, DYS547, DYS570, DYS576, DYS612, DYS626, DYS627 and DYS724, which group further comprises at least one RM Y-STR marker selected from the group consisting of DYF1000, DYF1001, DYF1002, DYR88, DYS685, DYS688, DYS712, DYS1003, DYS1007, DYS1010 and DYS1012, at least one FM Y-STR marker selected from the group consisting of DYS1013, DYS1016, DYS1017, DYS1009, DYS1014, DYF1004, DYS1005, and DYS1006, or a combination thereof. Preferably, the invention pertains to a group of Y-STR markers comprising one or more, preferably all RM Y-STR markers selected from the group consisting of DYF387S1, DYF399S1, DYF403S1A, DYF403S1B, DYF404S1, DYS449, DYS518, DYS526, DYS547, DYS570, DYS576, DYS612, DYS626, DYS627 and DYS724, and at least one RM Y-STR marker selected from the group consisting of DYF1000, DYF1001, DYF1002, DYS1003, DYS1007, DYS1010 and DYS1012. Said group preferably comprises 2 novel Y-STR markers, at least 3 novel Y-STR markers, at least 4 novel Y-STR markers, at least 5 novel Y-STR markers, at least 10 novel Y-STR markers, at least all 19 novel Y-STR markers selected from DYF1000, DYF1001, DYF1002, DYR88, DYS685, DYS688, DYS712, DYS1003, DYS1007, DYS1010, DYS1012, DYS1013, DYS1016, DYS1017, DYS1009, DYS1014, DYF1004, DYS1005, and DYS1006.

The novel RM and FM Y-STR markers were identified using a novel algorithm. Thus, also described herein is a method for in silico identifying RM Y-STR candidate markers, comprising identifying a Y-STR sequence by detecting one or more uninterrupted repeat stretches in the Y-chromosomal sequence of a human reference genome; assigning a mutability prediction score to said Y-STR, using equation 1; and having a mutability prediction score of 15 or more. As is evident from FIG. 2, 15 is the mutability prediction score that the majority of non-RM Y-STRs do not reach and the minimum score obtained for the 15 previously known RM Y-STRs.

With this novel approach the entire human Y chromosome reference sequence (build GRCh38) was screened and thus advantageously allowed the identification of Y-STR markers with an increased probability to have increased mutation rates that were not previously identified as such. For this approach, a novel algorithm was developed that can assign a mutability prediction score to any given Y-STR. This algorithm makes use of four molecular features found in the sequence of known Y-STR markers that are believed to be indicative of the (rapid) mutability of Y-STRs: i) the length of the uninterrupted repeat stretches, ii) the number of repeat stretches in a sequence, iii) the marker being a multi-copy marker, meaning that a highly similar sequence is found in multiple locations of the Y-chromosome and can be amplified with a single primer pair, iv) the size of the repeated motif. The first three factors each have a positive effect on the mutability of a Y-STR, with the length of the uninterrupted repeat stretches being the most dominant contributor, whereas tetranucleotide repeat markers have shown to have an higher mutation rate comparted to trinucleotide and pentanucleotide repeats markers.

The mutability score assigned to each uninterrupted repeat stretch can be expressed with equation 1.

$$e^{(0.15 \times number\ of\ repeat\ units)}.$$

equation 1

If multiple uninterrupted repeats were present (i.e. complex Y-STRs), the scores of the individual uninterrupted repeats were summed up. Similarly, the scores from different loci stemming from multi-copy markers were summed up. In equation 1, the factor of 0.15 was derived empirically by performing correlation analysis of the mutation rate with various factors. The factor that resulted in the highest correlation was 0.15, the results of the correlation using this factor are shown in FIG. 3.

Subsequently, Y-STR markers having a mutability prediction score of 15 or higher were empirically confirmed in a large-scale mutation rate study. In principle, any method known in the art can be used to determine the mutability of the Y-STRs, but preferably this is determined by genotyping a large enough data set of DNA-confirmed biological father-son pairs.

The group of Y-STR markers according to the invention can be suitably used for typing male individuals. Hence, the invention relates to the use of the group of Y-STR markers according to the invention for typing male individuals.

In addition, each individual novel RM Y-STR marker and/or novel FM Y-STR marker as defined herein above can be suitably used for typing male individuals, such as unrelated male individuals. Thus, the invention is also related to the use of a RM Y-STR marker selected from DYF1000, DYF1001, DYF1002, DYR88, DYS685, DYS688, DYS712, DYS1003, DYS1007, DYS1010, DYS1012, and/or a FM Y-STR selected from the group consisting of DYS1013, DYS1016, DYS1017, DYS1009, DYS1014, DYF1004, DYS1005, and DYS1006, for typing male individuals. Further, the novel RM Y-STR markers and/or FM Y-STR markers as defined herein, can be suitable to be used in contributing to differentiating paternally related males. Hence, the invention also relates to the use of a RM Y STR marker selected from the group consisting of DYF1000, DYF1001, DYF1002, DYR88, DYS685, DYS688, DYS712, DYS1003, DYS1007, DYS1010 and DYS1012 and/or a FM Y-STR selected from the group consisting of DYS1013, DYS1016, DYS1017, DYS1009, DYS1014, DYF1004, DYS1005, and DYS1006 for contributing to distinguishing male relatives.

Advantageously, typing of male individuals can be used in forensic genetics, in particular in cases where a single source DNA-sample is not available.

A specific example of a forensic application is in sexual assault cases where the DNA-sample contains an excess of the victim's (female) DNA. Based on such female-male DNA mixtures, it is often practically impossible to identify the male contributor based on autosomal STR analysis, because it does not allow discrimination of male and female DNA. In contrast, standard forensic Y-STR typing allows the identification of a Y-STR haplotype shared by members of a paternal lineage, and can differentiate males from different paternal lineages, but does not enable individual discrimination of male relatives within this paternal lineage. Herein, analysis of RM Y-STR markers and FM Y-STR markers can provide a solution as they allow differentiating closely and distantly related males who belong to the same paternal lineage.

Another suitable application is in forensic cases where no reference DNA sample is available, because it is neither present in databases or there is no potential suspect. In such forensic cases, mass screenings can be carried out via a familial search using standard Y-STRs, which takes advantage of the sharing of the standard Y-STR haplotype between members of the same paternal lineage that matches the standard Y-STR haplotype obtained from the crime scene DNA. If male relatives of the unknown perpetrator, who is likely not to participate himself, do participate in the mass screening, this allows highlighting these male relatives of the unknown perpetrator. Subsequently, RM Y-STRs and/or FM Y-STRs are used on all these highlighted male samples to separate closely related (showing no/few RM Y-STR mutations) from distantly related (more mutations) male relatives of the unknown perpetrator.

For finding the unknown perpetrator via focused police investigation, close relatives, as identified by RM Y-STR and/or FM Y-STR analysis, are more useful than distant relatives. Especially when applied to cases in rural areas, the number of paternally related men that live in the area and thus participate in mass screening is typically high so that there are many matches of the standard Y-STR haplotype since many members of the same paternal lineage participate. Using RM Y-STR and/or FM Y-STR markers will narrow down the pool of potential suspects by removing distantly related men that are less useful to find the unknown perpetrator who typically does not participate in the voluntary DNA mass screening.

Furthermore, the group of Y-STR markers according to the invention can be used for determining genealogic relationships. Here standard forensic Y-STR profiles can be used to confirm that two or more males belong to the same family. This genetic knowledge is used to confirm or correct family information obtained from sources such as archives or public records. Analyzing RM Y-STR and/or FM Y-STR markers gives an indication whether two or more subjects are closely or distantly related. Hence, the invention further relates to the use of at least one RM Y-STR marker selected from the group consisting of DYS685, DYS688, DYR88, DYS712, DYF1000, DYF1001, DYF1002, DYS1003, DYS1007, DYS1010 and DYS1012 and/or at least one FM Y-STR marker selected from the group consisting of DYS1013, DYS1016, DYS1017, DYS1009, DYS1014, DYF1004, DYS1005, and DYS1006 for determining genealogic relationships.

Moreover, the group of Y-STR markers according to the invention can be used to differentiate remotely paternally related males (separated by a large number of meiosis) belonging to the same paternal lineage into different sublineages, as well as to differentiate unrelated males into different paternal lineages. For remotely paternally related males the knowledge about their remote paternal relationship is typically absent from family and other knowledge; thus they are considered as unrelated males, even though they belong to the same paternal lineage. Because of the increased mutation rates of RM Y-STRs and FM Y-STRs compared to regular Y-STRs, the novel RM Y-STRs and FM Y-STRs will consequently show increased population diversity, compared to regular Y-STRs with lower mutation rates and thus lower diversity. Therefore, RM Y-STRs and/or FM Y-STRs are also more suitable than regular Y-STRs to differentiate remotely related males belonging to the same paternal lineage and to differentiate unrelated males belonging to different paternal lineages. Accordingly, the invention further relates to the use of at least one RM Y-STR marker selected from the group consisting of DYS685, DYS688, DYR88, DYS712, DYF1000, DYF1001, DYF1002, DYS1003, DYS1007, DYS1010 and DYS1012 and/or at least one FM Y-STR marker selected from the group consisting of DYS1013, DYS1016, DYS1017, DYS1009, DYS1014, DYF1004, DYS1005, and DYS1006 to differentiate remotely paternally related males (separated by a large number of meiosis) belonging to the same paternal lineage into different sublineages, as well as to differentiate unrelated males into different paternal lineages.

The invention further pertains to methods for amplification of alleles of Y-STR markers, including at least one allele of a RM Y-STR marker selected from DYF1000, DYF1001, DYF1002, DYR88, DYS685, DYS688, DYS712, DYS1003, DYS1007, DYS1010 and DYS1012, preferably selected from DYF1000, DYF1001, DYF1002, DYS1003, DYS1007, DYS1010 and DYS1012. In this method, one or more target Y-STR is/are amplified to generate amplicons. The method may further include a step of evaluating the amplicons, e.g. by detection of fluorescent or radioisotope labeled products. The amplicons are preferably compared to one or more reference standards, in order to determine whether a mutation such as a change in repeat numbers, has occurred in the target Y-STR sequence.

Thus, the invention further provides a method for amplifying an allele of at least one Y-STR marker, comprising the steps of contacting a sample suspected to contain a DNA sample of a male subject with a set of amplification primers comprising primers for the amplification of the allele of at least one Y-STR marker; and amplifying an allele of the at least one Y-STR marker, thereby forming one or more amplicons of the allele, wherein the Y-STR marker comprises at least one RM Y-STR marker selected from the group consisting of DYF1000, DYF1001, DYF1002, DYR88, DYS685, DYS688, DYS712, DYS1003, DYS1007, DYS1010 and DYS1012, at least one FM Y-STR marker selected from the group consisting of DYS1013, DYS1016, DYS1017, DYS1009, DYS1014, DYF1004, DYS1005, and DYS1006, or a combination thereof.

The sample may be any sample comprising nucleic acids of the male subject, such as blood, semen, saliva, urine, feces, hair, teeth, bone, tissue and cells. In some embodiments, the sample is obtained from a crime scene. In other embodiments, the sample is obtained directly from a subject, such as a suspect or a reference person, e.g. in terms of screening, for compiling a database or in terms of establishing genealogical relationships. The sample is preferably pre-treated to remove debris and/or other material that may interfere with the amplification step. Methods and compositions for isolation of genomic DNA are well known in the art and may be any method that is compatible with the subsequent amplification step. Preferably the method employs aqueous solvents without use of organic solvents and chaotropic salts. The isolated genomic DNA is preferably free of polymerase inhibitors. Commercial kits for isolation of genomic DNA are available, including Nucleo-Spin® Forensic Filters (Machery Nagel, DUren, Germany), innuPREP Forensic DNA Kit, Analytik Jena, Jena, Germany) and ChargeSwitch Forensic DNA Purification Kit (Thermo Fisher, Waltham, USA).

Different amplification methods, known to a skilled artisan, can be employed for amplification, including but not limited to Polymerase Chain Reaction (PCR), rolling circle amplification, nucleic acid sequence-based amplification, transcription mediated amplification and strand displacement amplification. A preferred amplification method is PCR, such as real-time PCR.

PCR is a technology that relies on thermal cycling, consisting of cycles of repeated heating and cooling of a reaction for DNA melting and enzymatic replication of the DNA. Primers containing sequences that specifically hybridize to the target regions, and a DNA polymerase are key components to enable selective and repeated amplification. As PCR progresses, the amplified DNA product that is generated is itself used as a template for replication, resulting in a chain reaction in which the DNA template is exponentially amplified.

A preferred DNA polymerase is a thermostable polymerase, preferably a thermostable recombinant polymerase. Preferred commercially available DNA polymerases include AptaTaq Fast DNA Polymerase, Amplitaq Gold (Thermo Fisher Scientific, Waltham, USA) and LightCycler® Fast-Start Enzyme (Roche Diagnostics, Almere, The Netherlands).

Real-time PCR, also called quantitative PCR (qPCR), is a technique, which is used to amplify and simultaneously quantify a template DNA molecule. The detection of the amplification products can in principle be accomplished by any suitable method known in the art. The amplified products may be directly stained or labeled with radioactive labels, antibodies, luminescent dyes, fluorescent dyes, or enzyme reagents. Direct DNA stains include for example intercalating dyes such as acridine orange, ethidium bromide, ethidium monoazide or Hoechst dyes.

Alternatively, the amplified product may be detected by incorporation of labeled dNTP bases into the synthesized DNA fragments. Detection labels, which may be associated with nucleotide bases include, for example, fluorescein, cyanine dye and BrdUrd.

The primer is preferably labeled with a detectable label, preferably a fluorescent label. Preferred labels for use in this invention comprise fluorescent labels, preferably selected from 6-FAM (Thermo Fisher Scientific Inc., Waltham, MA USA), VIC (Thermo Fisher Scientific Inc., Waltham, MA USA), NED FAM (Thermo Fisher Scientific Inc., Waltham, MA USA), SID (Thermo Fisher Scientific Inc., Waltham, MA USA), TAZ (Thermo Fisher Scientific Inc., Waltham, MA USA), LIZ (Thermo Fisher Scientific Inc., Waltham, MA USA), CXR (Promega Corporation, Madison, USA), TOM (Promega Corporation, Madison, USA), WEN (Promega Corporation, Madison, USA), BTG (Qiagen N.V., Venlo, the Netherlands), BTY (Qiagen N.V., Venlo, the Netherlands), BTR2 (Qiagen N.V., Venlo, the Netherlands), BTP (Qiagen N.V., Venlo, the Netherlands), Atto425 (ATTO-TEC GmbH, Siegen, Germany), Atto 647N (ATTO-TEC GmbH, Siegen, Germany), YakimaYellow (Epoch Biosciences Inc, Bothell, WA, USA), Ca1610 (BioSearch Technologies, Petaluma, CA, USA), Cal635 (BioSearch Technologies, Petaluma, CA, USA), FAM (Thermo Fisher Scientific Inc., Waltham, MA USA), TET (Thermo Fisher Scientific Inc., Waltham, MA USA), HEX ((Thermo Fisher Scientific Inc., Waltham, MA USA), cyanine dyes such as Cy5, Cy5.5, Cy3, Cy3.5, Cy7 (Thermo Fisher Scientific Inc., Waltham, MA USA), Alexa dyes (Thermo Fisher Scientific Inc., Waltham, MA USA), Tamra (Thermo Fisher Scientific Inc., Waltham, MA USA), ROX (Thermo Fisher Scientific Inc., Waltham, MA USA), JOE (Thermo Fisher Scientific Inc., Waltham, MA USA), fluorescein isothiocyanate (FITC, Thermo Fisher Scientific Inc., Waltham, MA USA), and tetramethylrhodamine (TRITC, Thermo Fisher Scientific Inc., Waltham, MA USA).

Preferably, the forward primer is labeled with a fluorophore, although it is also possible to label the reverse primer. If the forward primer is labeled, it is preferably labeled on the 5'-end of the forward primer, for example through a covalent link with the 5' phosphate or via a linker to the nucleobase.

The term "specifically hybridizing" refers to a nucleic acid molecule that is capable of hybridizing specifically under stringent hybridization conditions to the target nucleic acid template. In the present context, the "target nucleic acid template" is a RM Y-STR or a FM Y-STR as defined elsewhere, or a part thereof, such as an allele, optionally including flanking regions.

The terms "stringency" and "stringent hybridization" refer to hybridization conditions that affect the stability of hybrids, e.g., temperature, salt concentration, pH, and the like. These conditions are empirically optimized to maximize specific binding and minimize non-specific binding of primer or probe to its target nucleic acid sequence. The terms as used include reference to conditions under which a primer will hybridize to its target sequence, to a detectably greater degree than other sequences (e.g. at least 2-fold over background). Stringent conditions may be sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched primer. Hybridization procedures are well known in the art and are described by e.g. Ausubel et al., 1998. Current Protocols in Molecular Biology, John Wiley, New York; and Sambrook et al., 2001. Molecular cloning: a laboratory manual. Cold Spring Harbor Laboratory Press, New York.

An oligonucleotide primer, or an oligonucleotide mimic primer, is able to specifically hybridize to a target nucleic acid template when the length of the molecule is or resembles at least 15 bases. The length of the primer or probe is preferably less than 100 bases. A preferred length of a primer or probe is between 15 and 50 bases, preferably between 16 and 30 bases.

In general, a primer is able to hybridize to a target nucleic acid template when the percentage of sequence identity of the molecule is at least 90% over substantially the whole length, more preferred at least 91%, more preferred at least 92%, more preferred at least 93%, more preferred at least 94%, more preferred at least 95%, more preferred at least 96%, more preferred at least 97%, more preferred at least 98%, more preferred at least 99%, more preferred 100% identical to a nucleic acid that is obtained or derived from said target nucleic acid template over substantially the whole length of the primer or probe. The term "substantially the whole length" is used to indicate that the probe may comprise additional nucleotide sequences, for example at the 5' and/or 3' ends that are not present in the gene or region described herein above.

In case related, but not identical, short terminal repeat sequences are located on other chromosomes such as the X-chromosome, PCR conditions are chosen that preferentially amplify Y chromosomal DNA loci. As a result, only male DNA will give a PCR product but not female DNA. This is part of the PCR optimization strategy where negative results in female DNA are preferably demonstrated. As is known to a person skilled in the art, PCR reactions under more stringent conditions, such as lower salt concentrations and higher temperatures, may be chosen to preferentially amplify short terminal repeat sequences from Y chromosomal DNA loci that are more identical to the primer sequences, when compared to sequences on other chromosomes.

Efficient PCR reactions are dependent upon high quality primer design. Rules of thumbs for the design of primers include the selection of primers having a Tm between 58° C. and 65° C. while keeping the annealing temperatures of the primers as close as possible, having no more than two G's or C's in the last 5 bases at the 3' end, and the selection of primer pairs with minimal number of potential primer dimers and primer hairpins.

Methods for the design of primers are known in the art. For example, Premier Biosoft (Palo Alto, CA, USA) offers AlleleID® and Beacon Designer™ to design probes for PCR assays that are free of dimers, repeats and runs and ensure signal fidelity. In addition, Primer3 (available at @primer3.sourceforge.net) and Integrated DNA Technologies, Inc. (available at idtdna.com/Scitools/Applications/Primerquest) provide online tools for the design of primers for real-time PCR assays. Hence, the skilled person is able to design primers for amplification, including PCR, of one or more target nucleic acid templates.

The primers are preferably tested in single nucleic acid amplification reactions (monoplex) and combined nucleic acid amplification reactions (multiplex) to determine optimal combinations of specific nucleic acid amplification reactions. An amplicon preferably has a length of less than 1000 base pairs, more preferably less than 450 base pairs, preferably less than 420 base pairs, more preferably less than 400 base pairs, in particular less than 350 base pairs, less than 300 base pairs, less than 250 base pairs or less than 200 base pairs. At least one amplicon is formed, but preferably more than one amplicon, i.e. a plurality of amplicons is formed.

The amplicons are preferably detected or analyzed. Thus, in an embodiment, the amplicons are labelled with a detectable label, preferably a fluorescent label. In practice, this is preferably achieved by labelling at least one of the set of amplification primers with a detectable label, in particular a fluorescent label.

Alternatively, detection may be achieved by staining of the amplicons with a DNA stain, such as ethidium bromide after separation of the amplicons by, for example, electrophoresis. As an alternative, detection may be achieved by a laser and a detector cell, for example, after capillary electrophoresis.

Detection of the amplicons preferably is performed by size fractionation employing, for example, capillary electrophoresis. For this, it is important that the sizes of the amplicons differs sufficiently to allow the separation of the individual amplicons, taking into consideration that the size of a particular amplicon may differ in an individual having a mutation such as a different repeat number, in one or more of the amplicons that are amplified from the Y-STR markers. As an alternative, or in addition, detection of the amplicons may involve sequence analysis of the amplicons. Sequence analysis may be performed by any method known in the art, including but not limited to dideoxy sequencing, matrix-assisted laser desorption/ionization time-of-flight mass spectrometry, and sequencing by hybridization, including hybridization with sequence-specific oligonucleotides and hybridization to oligonucleotide arrays. The nucleotide sequence of one of more amplicons can also be determined by application of mutation analysis methods such as single stranded conformation polymorphism, DNA heteroduplex analysis, denaturing gradient gel electrophoresis and thermal gradient gel electrophoresis. As will be clear to a person skilled in the art, sequence analysis not necessarily involves labeling of the amplicons with a detectable label.

Sequence analyses preferably is performed by indirect sequencing of a relevant nucleic acid after amplification of all or any part of the Y-STR marker. Alternative direct or indirect methods comprise hybridization protection assay, allele-specific amplification, ligase-mediated detection, primer extension, and restriction fragment length analysis.

As will be clear to a person skilled in the art, next generation sequencing methods, including whole-genome sequencing and targeted next generation sequencing, may be used to identify different alleles of one or more of the Y-STR markers employing, for example on an Ion Torrent sequencing platform, an Illumina sequencing platform, or other sequencing platforms such as third generation sequencing platforms, for example nanopore sequencing on an Oxford Nanopore Technologies platform, and single-molecule real-time sequencing (SMRT sequencing) on a PacBio platform, with or without prior amplification of the markers.

The method thus allows for the identification of an allele of the one or more RM Y-STRs. In particular, this is achieved by the detection of a mutation such as a difference in the number of repeats, in the one or more RM Y-STR marker(s). Accordingly, the invention also relates to a method to detect the presence of mutations in a nucleic acid in a sample containing the nucleic acid, comprising (a) contacting in a solution said sample with a set of amplification primers under conditions permitting hybridization between said primers and the nucleic acids in said sample, wherein at least one of the amplification primers comprises a detectable label; (b) detecting the one or more amplicons, each amplicon labeled with a detectable label, wherein the number of repeats within the amplicon determines an allele of a RM Y-STR marker according to the invention.

As an alternative, or in addition, the amplicons may be labeled with a detectable label, in particular with a fluorescent label.

The detectable label may be any label that allows detection with common methods known in the art, but is preferably a fluorescent label such as a fluorophore or a fluorescent nucleobase. Suitable methods to detect a fluorescent label are known in the art, e.g. fluorescence detector.

In an embodiment the amplicon is compared to a reference nucleic acid. This reference nucleic acid preferably is an internal reference nucleic acid. This means that the alleles of a Y-STR of two or more males suspected to be from a paternal lineage are amplified in a method according to the invention, and the amplicons are compared relative to one another. If the amplicons are the same, no mutation may have occurred and the male relatives cannot be distinguished. Alternatively, a difference in the alleles indicates the presence of a mutation, which allows differentiation of the male relatives. If the alleles of target Y-STR markers of multiple males from the same paternal lineage are subject of the method of the invention, the internal reference is the allele that is found in the majority of the Y-STR markers. If only two paternally related males are compared, the internal reference is the amplicon derived from the other male relative, e.g. when one or more Y-STR markers of a father and a son are compared, the amplicon of the father is the internal reference to the amplicon of the son and vice versa.

A preferred method to compare the amplicons is by electrophoresis, in particular capillary electrophoresis (Buel et al., 1998. J Forensic Science 43: 164-170). Herein, the amplicons are compared in terms of size/molecular weight, wherein a difference in size or molecular weight indicates the presence of a mutation. The skilled person is familiar with these methods.

Alternatively, or in addition, the amplicon may be compared to an external reference standard, such as a DNA ladder, such GeneScan™ 600 LIZ™ dye Size Standard v2.0 (Thermo Fisher Scientific, Waltham, MA USA) and Internal Lane Standard 600) (Promega, Madison, WI, USA), to an Y-STR marker sequence derived from the human Y chromosome, or to both. The external reference standard is preferably labelled, more preferably fluorescently labelled so that the amplicon can be compared to the reference sample in a suitable method, such as capillary electrophoresis.

Hence, the invention further relates to a method to detect the presence of a mutation in a nucleic acid in a sample containing the nucleic acid, comprising the steps of contacting a sample suspected to contain a DNA sample of a male subject with a set of amplification primers under conditions permitting hybridization between said primers and the nucleic acids in said sample; amplifying said DNA sample; identifying an allele of at least one of DYF1000, DYF1001, DYF1002, DYR88, DYS685, DYS688, DYS712, DYS1003, DYS1007, DYS1010 and DYS1012 by sequencing the amplified DNA sample; and comparing the amplicons of the allele with a reference nucleic acid; wherein a difference in the alleles indicates the presence of a mutation.

A difference in alleles may be a difference in nucleotide sequence, size, molecular weight or a difference in the number of repeats of the alleles.

In another embodiment, the amplicon may also be sequenced, using common sequencing methods known in the art, e.g. Sanger sequencing, pyrosequencing, Maxam and Gilbert sequencing, or any type of targeted or non-targeted next or third generation sequencing, including whole genome sequencing.

The method can be employed to amplify one or more RM Y-STR markers or FM Y-STR markers either separately (i.e. in different reactions) or simultaneously (in one reaction).

Preferably, the invention relates to a method for amplifying an allele of two or more RM Y-STR markers, more preferably three or more RM Y-STR markers or FM Y-STR markers, four or more, five or more, six or more RM Y-STR markers or FM Y-STR markers, such as 24 markers, 32 markers, more preferably all RM Y-STR or all RM Y-STR and FM Y-STR markers.

Said amplification of RM Y-STR or FM Y-STR markers preferably is performed using a multiplex PCR reaction. This method allows the fast screening of RM Y-STR markers and FM Y-STR markers.

In such a multiplex PCR method, the sets of amplification primers configured to amplify the different RM Y-STR markers preferably each comprise one fluorescently labeled primer, whereby each RM Y-STR marker comprises a distinguishable label such as a fluorescent label. This allows the discrimination of the amplicons, based on the detection of different fluorescent labels. When sequencing is used for detection of the Y-STR markers, such as targeted or non-targeted NGS, no labeled primers are used.

Optimized primers for multiplex real-time PCR are provided in Table 2. Accordingly, the invention further relates to a set of amplification primers comprising primers for the amplification of at least one Y-STR marker, wherein the set of primers are configured to provide amplicons of the at least one RM Y-STR markers. Said set of primers include primers for the amplification of at least one Y-STR marker selected from the group consisting of DYF1000, DYF1001, DYF1002, DYR88, DYS685, DYS688, DYS712, DYS1003, DYS1007, DYS1010 and DYS1012, more preferably selected from the group consisting of DYF1000, DYF1001, DYF1002, DYS1003, DYS1007, DYS1010 and DYS1012.

Preferably the Y-STR marker includes one or more RM Y-STR markers selected from the group consisting of DYF1000, DYF1001, DYF1002, DYR88, DYS685, DYS688, DYS712, DYS1003, DYS1007, DYS1010 and DYS1012, more preferably selected from the group consisting of DYF1000, DYF1001, DYF1002, DYS1003, DYS1007, DYS1010 and DYS1012, one or more FM Y-STR marker selected from the group consisting of DYS1013, DYS1016, DYS1017, DYS1009, DYS1014, DYF1004, DYS1005, and DYS1006, or a combination thereof.

The invention further pertains to a kit for amplifying an allele of a RM Y-STR marker, comprising a set of amplification primers as defined elsewhere and one or more reference standards. Said set of amplification primers preferably include the primers listed in Table 2 or Table 6. The reference standard is preferably an allele of the RM Y-STR marker to be amplified, derived from the human Y chromosome.

For the purpose of clarity and a concise description features are described herein as part of the same or separate embodiments, however, it will be appreciated that the scope of the invention may include embodiments having combinations of all or some of the features described.

The invention will now be illustrated with the following non-limiting examples.

EXAMPLES

Example 1; Identification of RM Y-STR Markers
by in-Silico Sequence Analysis

A new strategy was developed to predict, based on the human reference genome sequence (GRCh38; Schneider et al., 2017. Genome Res 27: 849-864), which STR locus is prone to high mutability. This strategy allows the identification of novel markers, that were not previously known as markers.

For this, a novel algorithm that can assign a mutability prediction score to any given Y-STR was developed. This algorithm makes use of four molecular features found in the sequence that are believed to impact the mutability of a Y-STR: i) the length of the uninterrupted repeat stretches, ii) the number of repeat stretches in a sequence, iii) the marker being a multi-copy marker, meaning that a highly similar sequence is found in multiple locations of the Y-chromosome and can be amplified with a single primer pair, iv) the size of the repeated motif. The first three factors each have a positive effect on the mutability of a Y-STR, with the length of the uninterrupted repeat stretches being the most dominant contributor, whereas tetranucleotide repeat markers have shown to have an higher mutation rate comparted to trinucleotide and pentanucleotide repeats markers.

In order to assign the mutability prediction score to a given Y-STR sequence, first the sequence was converted to an "STR structure sequence", which counts and shows the repeats (equal to, or greater than 5 repeats) in a systematic way. For each repeat belonging to the same family a single repeat nomenclature was applied, i.e. $[AAAG]_n$ (SEQ ID NO: 1), $[AAGA]_n$ (SEQ ID NO: 2), $[AGAA]_n$ (SEQ ID NO: 3), and $[GAAA]_n$ (SEQ ID NO: 4), but also the complementary $[TTTC]_n$ (SEQ ID NO: 5), $[TTCT]_n$ (SEQ ID NO: 6), $[TCTT]_n$ (SEQ ID NO: 7), and $[CTTT]_n$ (SEQ ID NO: 8), were all counted as $[AAAG]_n$ (SEQ ID NO: 1).

An exponential function was derived empirically from the Y-STRs and mutation rates described previously (Ballantyne et al., 2010. Ibid). The score assigned to each uninterrupted repeat stretch can be expressed as $e^{(0.15 \times number\ of\ repeat\ units)}$; if multiple uninterrupted repeats were present (i.e. complex Y-STRs), the scores of the individual uninterrupted repeats were summed up. Also for multi-copy Y-STR markers, the scores of the different copies were summed up. As is shown in FIG. 3, the value of 0.15 was determined empirically by testing various values and selecting the one that showed the largest correlation. For example, the previously identified RM Y-STR DYS627 (Ballantyne et al., 2010. Ibid) contains two repeat stretches, one of six and one of eighteen repeats in the Y-chromosome reference sequence (GRCh38) (FIG. 1); thus, the score assigned to this RM Y-STR is $e^{0.9}+e^{2.7}=2.46+14.88=17.34$. The other previously identified RM Y-STR used as an example in FIG. 1, DYS526b, has three repeat stretches and received a score of $e^{2.1}+e^{1.35}+e^{1.95}=19.12$. Lastly, tetranucleotide repeats were previously found to be more mutable than other motifs, i.e. trinucleotide, or pentanucleotide repeats, when considering similar numbers of repeat units (Ballantyne et al., 2010. Ibid; Eckert & Hile, 2009. Mol Carcinogenesis 48: 379-388). Therefore, if the repeat motif-predominantly-belonged to any other motif size class, the final score was adjusted by dividing it by a factor 2 (mononucleotide and dinucleotide repeats were not considered in this study).

Next, to demonstrate that this mutability prediction score is indeed indicative of the Y-STR mutability, the scores obtained from all 14 (RM Y-STRs ($\mu > 10^{-2}$) previously identified by Ballantyne et al. (Ballantyne et al., 2010. Ibid), were compared to those obtained of 171 previously identified non-RM Y-STR ($\mu < 10^{-2}$).

From FIG. 2 it becomes evident that the previously identified RM Y-STRs indeed demonstrate a higher score than the non-RM Y-STRs demonstrating the feasibility of our new approach. FIG. 3 shows a positive correlation between the mutability prediction score and the observed mutation rate using these 185 Y-STRs, with an observed $R^2$ value of 0.53 the correlation between these two statistics is relatively high confirming the feasibility of our new approach. These analyses demonstrate that our new algorithm is able to differentiate RM Y-STRs from non-RM Y-STRs and shall thus be suitable to find new RM Y-STR candidate markers when being applied to the reference genome sequence.

To search for new candidate RM Y-STR makers (cRM Y-STRs) using our mutability prediction scores, first a catalogue containing all Y-STRs present in the latest assembly of the human genome (GRCh38) was built by using publically available software "Tandem repeats finder", available at tandem.bu.edu/trf/trf.html. The following parameters were set in the software: Match=2, Mismatch=100, Delta=100, PM=80, PI=10, Minscore=12, Max-Period=5. These settings resulted in a catalogue containing only uninterrupted (perfect) STRs with a maximum repetitive motif size of 5 base pairs. For the purpose of this study, only STRs located on the Y chromosome were considered for further analyses and STRs located on other chromosomes were excluded. From the resulting Y-STR catalogue, all Y-STRs with repeats having a motif size below 3 bp (because dinucleotide repeats are notoriously difficult to analyze due to increased PCR slippage), and Y-STRs with repeat stretches with less than 4 repetitions (because those are unlikely to by highly polymorphic as required for forensic applications) were discarded. Finally, Y-STRs located in pseudoautosomal regions (PAR) of the Y-chromosome were excluded and were not considered for further analysis, because such regions undergo recombination with the X-chromosome and thus not necessarily harbor male-specific Y-STRs.

From the identified cRM Y-STRs, Y-STR markers from which the mutation rates were previously established in a large study (Ballantyne et al., 2010. Ibid) were excluded, to focus the further experimental verification on uncharacterized 38 cRM Y-STRs.

With this approach 38 novel candidate RM Y-STR markers were identified, which included 1 Y-STR marker that was recently described with increased mutation rate from deep-routing pedigree analysis (DYS724; Claerhout et al., 2018. Forensic Science Int: Genetics 34: 1-10). Previously, information about Y-STRs, i.e. nomenclature and genomic locations was stored in the Human Genome Database (GDB), which is no longer available. Therefore, new names were proposed for those markers to which no name had been previously assigned.

Example 2: Primer Design

PCR primer design was performed using Bisearch (Tusnady et al., 2005. Nucleic Acid Res 33: e9) to estimate the melting temperature of the primers, Bisearch was also used to perform in silico PCR in which only Y-chromosome specific in silico amplicons were allowed. Lastly, Bisearch was used to ensure that individual primers were reasonably specific, i.e. did not bind to many hundreds, or thousands of locations across the human genome. All primer pairs that were designed were first tested by performing singleplex PCRs on both male and female DNA samples to ensure male-specific amplification. For this, the PCR products were visualized on agarose gels. In cases where amplification in female samples was seen, PCR primers were redesigned. If also redesigning the primers did not lead to male-specific amplification, capillary electrophoresis (CE) was used to check if the not male-specific amplification products interfere with the male-specific products. If this was not the case, the marker remained in the study; if this was the case, the marker was excluded from further analyses. Of the 37 cRM Y-STRs considered for primer design, 11 were excluded due to unspecific amplification overlapping with male-specific products despite our attempts, leaving 26 cRM Y-STR markers for empirical testing (Table 1).

In total, PCR primers for 26 cRM Y-STRs were successfully designed; those 26 markers were divided between six multiplex PCR assays each amplifying 4 to 6 dRM Y-STRs simultaneously to allow more efficient (compared to singleplex PC1R) genotyping of the large number of DNA samples from fathers and their sons that were considered in this study. Autodimer software (Vallone and Butler, 2004. Bio-Techniques 37: 10.2144/04372ST03) was used to ensure the primer combinations had minimal primer interactions. Oligonucleotides targeting the 26 dRM Y-STRs were purchased with 5' labeling of the forward primer using either 6-Fain, Joe, or TAMRA (Metabion International AG, Planegg, Germany). Primer sequences of the dRM Y-STRs are shown in Table 2.

TABLE 1 cRM Y-STR markers identified with the algorithm
and their calculated mutability prediction score

| Marker name | Genomic location | Mutability prediction score |
|---|---|---|
| DYF1001 | chrY: 23054609-23055044; chrY: 24688349-24688790; chrY: 24981317-24981750 | 107 |
| DYF1000 | chrY: 17854578-17854919; chrY: 18051088-18051432; chrY: 24024183-24024480; chrY: 25645653-25645953 | 123 |
| DYR88 | chrY: 24331827-24332233; chrY: 25337916-25338322 | 35 |
| DYS712 | chrY: 13446462-13446882 | 15 |
| DYS688 | chrY: 8465358-8465755 | 68 |
| DYS1012 | chrY: 56858298-56858581 | 23 |
| DYF1002 | chrY: 16242183-16242603; chrY: 16342720-16343155 | 48 |
| DYS1007 | chrY: 17299905-17300373 | 23 |
| DYS1010 | chrY: 17324747-17325139 | 24 |
| DYS685 | chrY: 7963956-7964261 | 25 |
| DYS1003 | chrY: 15084614-15085009 | 34 |
| DYS1013 | chrY: 14697144-14697687 | 17 |
| DYS1005 | chrY: 7849377-7849841 | 25 |
| DYS1016 | chrY: 12092576-12093208 | 21 |
| DYS1017 | chrY: 5541615-5541844 | 13 |
| DYS1009 | chrY: 17642914-17643292; chrY: 18262718-18263092 | 26 |
| DYS1014 | chrY: 3772704-3773174 | 18 |
| DYR33 | chrY: 17388667-17388955 | 13 |
| DYS724 | chrY: 19985806-19986053 | 7 |
| DYF1004 | chrY: 18466997-18467397; chrY: 18852999-18853399 | 30 |
| DYS1006 | chrY: 13208543-13208915 | 18 |
| DYS1015 | chrY: 15682003-15682475 | 19 |
| DYS563 | chrY: 17911925-17912161; chrY: 17993821-17994081 | 11 |
| DYS1011 | chrY: 23505396-23505720; chrY: 26164893-26165213 | 23 |
| DYS524 | chrY: 17787597-17787931; chrY: 18118078-18118412 | 23 |
| DYS1008 | chrY: 7443263-7443654 | 21 |

Example 3: Empirical Confirmation of RM Y-STR Markers

To practically characterize the 26 cRM Y-STRs and thus identifying new RM Y-STRs, the mutation rates of the 26 cRM Y-STRs were empirically estimated by genotyping more than 1,600 DNA-confirmed true biological father-son pairs of European descent that were previously used (Ballantyne et al., 2010. Ibid; Goedbloed et al., 2009. Ibid). Polymerase chain reaction (PCR) primers targeting the 26 cRM Y-STRs were designed with 5' labeling using either 6-Fam, Joe, or TAMRA (Metabion). Primers were designed as described in example 2. Each multiplex was optimized using 5 human male DNA samples, 1 female human DNA sample, and two negative control samples. PCR reactions were performed in 10 µL volumes, containing 5 µL of QIAGEN Multiplex PCR Master Mix (Qiagen), 1 µL of template DNA and oligo nucleotides at varying concentrations ranging from 0.1 to 1 µM. The PCR reactions were performed on GeneAmp PCR System 9700 (Thermo Fisher Scientific) using both 96-well and 384-well dual blocks. Every multiplex reaction was amplified with the same 65-55° C. Touch-down PCR protocol: 94° C. for 10 min, 10 cycles of 94° C. for 30 s, 65-1° C. every cycle for 60 s and 72° C. for 60 s, followed by 25 cycles of 94° C. for 30 s, 50° C. for 30 s and 72° C. for 60 s with a final extension step of 60° C. for 45 min. After amplification, 1 µL of the PCR product was mixed with 9 µL of Hi-Di Formamide and with 0.3 µL of ILS600 size standard (Promega). This mixture was incubated at 95° C. for 3 minutes and rapidly cooled on ice for 5 minutes.

For amplification detection, capillary electrophoresis was performed on an ABI3130XL Genetic Analyzer (Thermo Fisher Scientific) using sixteen 36 cm capillaries and POP-7 Polymer (Thermo Fisher Scientific). The Any4Dye matrix (Promega) was installed which allowed for accurate separation of signal from the different fluorescent labels. The resulting electropherograms were analyzed using Genemapper v4.0 software (Thermo Fisher Scientific).

The newly developed multiplex systems were used to genotype 3,232 DNA samples for the 26 cRM Y-STRs representing a total of 1,616 father-son pairs, for which the true biological father-son relationship was previously established by autosomal DNA testing (Ballantyne et al., 2010. Ibid). If an allelic difference was observed between a given father and his son at any cRM Y-STR tested, the result was confirmed by an independent genotyping of both father and son to establish the allelic difference to represent a mutation. The mutation rates were calculated by dividing the number of mutations observed by the total number of pairs that were tested per each cRM Y-STR analysed. The binomial distribution was used to calculate the 95% confidence intervals of the observed mutation rates.

The mutation rate estimates as displayed in Table 3 were determined for a total of 1616 father-son pairs genotyped for each 26 cRM Y-STR. The results show that of the 26 cRM Y-STRs, a total of 11 (43%) were confirmed as being true RM Y-STRs with mutation rates above $10^{-2}$. Another 10 (38%) cRM Y-STRs showed mutation rates below $10^{-2}$, but above $5.0 \times 10^{-3}$. Although not qualifying as RM Y-STRs per definition, the mutation rates of these Y-STRs were still higher than those of most of the previously described Y-STRs. Therefore they were designated as fast mutating (FM) Y-STRs.

The observed mutation rates correlate well with the mutability prediction score ($R^2$=0.65, FIG. 5). These results demonstrate the power of our new algorithm to identify RM Y-STRs as confirmed by empirical mutation rate estimations.

Example 4: Estimation of Male Relative Differentiation Capacities of Y-STR Markers To determine how valuable the newly identified RM Y-STRs are for differentiating male relatives, as relevant in future forensic applications, first male relative differentiation capacities for male relative pairs separated by 1-10 genetic transfers (meioses) were estimated using the mutation rate estimates which were empirically derived in our mutation rate study. The male relative differentiation capacities (rd) based on estimated mutation rates (rm) were calculated for different number of separating meioses (m) using the formula:

$$r_d = 1 - \prod_{i=1}^{n}(1 - r_m)^m r_d = 1 - \prod_{i=1}^{n}(1 - r_m)^m. \qquad \text{Formula 2}$$

TABLE 2

Forward and reverse primers designed for amplification of the Y-STR markers

| Marker name | Forward primer | Reverse primer |
|---|---|---|
| DYF1001 | GCCTGGGCAA CAAAAGTG (SEQ ID NO 9) | GCACAGCAGA CCTGTTCTAC AA (SEQ ID NO 10) |
| DYF1000 | AGGGAGCTTC AGTGTGCTTC (SEQ ID NO 11) | TGGCTTGACT CAGAAACTTG AC (SEQ ID NO 12) |
| DYR88 | CACCTGTAAT CCTAGCTACT CAGA (SEQ ID NO 13) | GCTTTCTCAT CATAGAGTGC TCATG (SEQ ID NO 14) |
| DYS712 | GTGGCTCACT CCTATAACC (SEQ ID NO 15) | AACTTTGTAG TAAGTTTTGA GACTGG (SEQ ID NO 16) |
| DYS688 | TATTCTAGAC TCTGCTCAGA GAGGTG (SEQ ID NO 17) | GCTGTCATTG TATCTCTTCA CTCC (SEQ ID NO 18) |
| DYS1012 | GCAAGACTCC ATCTCCAAAA AG (SEQ ID NO 19) | CAAGCTTGGG TCCATTATGA (SEQ ID NO 20) |
| DYF1002 | GCAAGACCAT GTCTTGAAAG (SEQ ID NO 21) | GCAAGTCCTC ATTATTTGC (SEQ ID NO 22) |
| DYS1007 | GCACATGTCT ATAGTCCCAT CTACC (SEQ ID NO 23) | GCCACTGAGT AATTCTTGAG AATTT (SEQ ID NO 24) |
| DYS1010 | AGAATCTATG ATCACAGCAC TTTTCT (SEQ ID NO 25) | CTTTCTACCT CATTTTCTTT CTGTCC (SEQ ID NO 26) |
| DYS685 | GGGCTTTATA AGTTATCTGA GGC (SEQ ID NO 27) | GGTGACAGAC TCCATCTTAA (SEQ ID NO 28) |
| DYS1003 | GTGAGACTCC ATCTCAAAAG AAG (SEQ ID NO 29) | ATCTGGTGTG TGAAGGACAG C (SEQ ID NO 30) |
| DYS1013 | TTATCTTGCT GACCATTAGA GAAGAT (SEQ ID NO 31) | CCTCTACCTA CCTACCTGCC TATGTA (SEQ ID NO 32) |
| DYS1005 | CTATAGTTCC TAGAGCAAAG | AGGTTGTGGT AATCTGAGAT |

TABLE 2-continued

Forward and reverse primers designed
for amplification of the Y-STR markers

| Marker name | Forward primer | Reverse primer |
|---|---|---|
| | AGTGAGC (SEQ ID NO 33) | TGC (SEQ ID NO 34) |
| DYS1016 | GAGTGAAACC ATCTCTAAGA C (SEQ ID NO 35) | GCTTGCAAAC ACACCATGA (SEQ ID NO 36) |
| DYS1017 | ATAGGACAGG TGGTTGAATG (SEQ ID NO 37) | CTAGATTTTC AGATAGTACA ACC (SEQ ID NO 38) |
| DYS1009 | TCCCAGAGTC TCAGAGTGCT G (SEQ ID NO 39) | GCCATAGAAG TCACCAGCTA GG (SEQ ID NO 40) |
| DYS1014 | ACCTTCTGGC GAAGTAACCC (SEQ ID NO 41) | TCTCAGCACT GCACTCTAGC T (SEQ ID NO 42) |
| DYR33 | ACTGAACGCT AGCCTGGGT (SEQ ID NO 43) | ACCCATATAG CTATCCATCT GTCTAAT (SEQ ID NO 44) |
| DYS724 | ACCGAAGCTG TTCCTATTAG GC (SEQ ID NO 45) | CTGTCAAAGA TGTAATGGGT ATGGTAC (SEQ ID NO 46) |
| DYF1004 | GCAAAGCAGA ATATTTATGT TTCAGT (SEQ ID NO 47) | AAAAATTTGC GAGGTGTGG (SEQ ID NO 48) |
| DYS1006 | CAAGACCAGC ATATCAGTTG AGG (SEQ ID NO 49) | GGCTCACTGC AACCTCCTAC (SEQ ID NO 50) |
| DYS1015 | GCATATCATC TATCACCTAT ATTAT (SEQ ID NO 51) | ATAAATAGAA GATAGGTAGA TAAC (SEQ ID NO 52) |
| DYS563 | GCCTGAGTAA CACTGCAAGA TTCT (SEQ ID NO 53) | AGAGACAATT TTCTATGCTC CAGC (SEQ ID NO 54) |
| DYS1011 | TCCAATCAGG AACATTTTAA AGC (SEQ ID NO 55) | TAAGTTATCT TTAGCTTTTT GCTGGC (SEQ ID NO 56) |
| DYS524 | GCCAAGATCA CAACCATTG (SEQ ID NO 57) | TGTATGAGCA ATGCTAAGTT AAAACAA (SEQ ID NO 58) |
| DYS1008 | ACATGATAGG AAATATGATT CTGGG (SEQ ID NO 59) | AATTAGTTGG AAGTGTGTGA CCCT (SEQ ID NO 60) |

Different sets and combinations of sets of Y-STRs were tested: a) the commercially available and widely used Amp-FLSTR Yfiler set of 16 Y-STRs that represent standard forensic Y-STRs with mutation rates in the order of $10^{-3}$ (Goedbloed et al., 2009. Ibid); b) the set of previously published 14 RM Y-STRs (Ballantyne et al., 2010. Ibid; Ballantyne et al., 2012. Forensic Science Int Genet 6: 208-218; Claerhout et al., 2018. Ibid); c) the set of 11 newly identified RM Y-STRs; d) a subset of 7 newly identified RM Y-STRs; e) the set of 8 newly identified FM Y-STRs combined with the 11 newly identified RM Y-STRs; f) the set of 11 newly identified RM Y-STRs combined with the previously published 15 RM Y-STRs; g) the set of 11 newly identified RM Y-STRs combined with the 8 newly identified FM Y-STRs and combined with the 15 previously publishes RM Y-STRs (FIG. 6).

Please note that the 7 RM Y-STRs under d) are the newly identified Y-STRs that were not known as Y-STRs before, and for which we newly established mutation rates, demonstrating that these markers have mutation rates $>10^{-2}$ i.e. are RM Y-STRs. The 11 RM Y-STRs under c) include these 7 new RM Y-STRs from d) plus 4 previously identified Y-STRs for which no mutation rates were previously available and for which we newly established mutation rates, demonstrating that these markers have mutation rates $>10^{-2}$, i.e. are RM Y-STRs.

TABLE 3

Empirical mutation rates of the cRM Y-STR markers

| Entry | Marker name | Mutability prediction score | No. of mutations observed | Mutation rate | 95% Confidence interval mutation rates |
|---|---|---|---|---|---|
| 1 | DYF1001 | 107 | 84 | $5.2\ 10^{-2}$ | $5.2\ 10^{-2}$-$6.4\ 10^{-2}$ |
| 2 | DYF1000 | 123 | 58 | $3.6\ 10^{-2}$ | $2.7\ 10^{-2}$-$4.6\ 10^{-2}$ |
| 3 | DYR88 | 35 | 47 | $2.9\ 10^{-2}$ | $2.1\ 10^{-2}$-$3.9\ 10^{-2}$ |
| 4 | DYS712 | 15 | 44 | $2.7\ 10^{-2}$ | $2.0\ 10^{-2}$-$3.6\ 10^{-2}$ |
| 5 | DYS688 | 68 | 43 | $2.7\ 10^{-2}$ | $1.9\ 10^{-2}$-$3.5\ 10^{-2}$ |
| 6 | DYS1012 | 23 | 31 | $1.9\ 10^{-2}$ | $1.3\ 10^{-2}$-$2.7\ 10^{-2}$ |
| 7 | DYF1002 | 48 | 29 | $1.8\ 10^{-2}$ | $1.2\ 10^{-2}$-$2.6\ 10^{-2}$ |
| 8 | DYS1007 | 23 | 25 | $1.6\ 10^{-2}$ | $1.0\ 10^{-2}$-$2.3\ 10^{-2}$ |
| 9 | DYS1010 | 24 | 23 | $1.4\ 10^{-2}$ | $9.0\ 10^{-3}$-$2.1\ 10^{-2}$ |
| 10 | DYS685 | 25 | 23 | $1.4\ 10^{-2}$ | $9.0\ 10^{-3}$-$2.1\ 10^{-2}$ |
| 11 | DYS1003 | 34 | 21 | $1.2\ 10^{-2}$ | $7.1\ 10^{-3}$-$1.8\ 10^{-2}$ |
| 12 | DYS1013 | 17 | 16 | $9.9\ 10^{-3}$ | $5.7\ 10^{-3}$-$1.6\ 10^{-2}$ |
| 13 | DYS1005 | 25 | 15 | $9.3\ 10^{-3}$ | $5.2\ 10^{-3}$-$1.5\ 10^{-2}$ |
| 14 | DYS1016 | 21 | 14 | $8.7\ 10^{-3}$ | $4.7\ 10^{-3}$-$1.5\ 10^{-2}$ |
| 15 | DYS1017 | 13 | 13 | $8.0\ 10^{-3}$ | $4.3\ 10^{-3}$-$1.4\ 10^{-2}$ |
| 16 | DYS1009 | 26 | 11 | $6.8\ 10^{-3}$ | $3.4\ 10^{-3}$-$1.2\ 10^{-2}$ |
| 17 | DYS1014 | 18 | 11 | $6.8\ 10^{-3}$ | $3.4\ 10^{-3}$-$1.2\ 10^{-2}$ |
| 18 | DYR33 | 13 | 11 | $6.8\ 10^{-3}$ | $3.4\ 10^{-3}$-$1.2\ 10^{-2}$ |
| 19 | DYS724 | 7 | 10 | $6.2\ 10^{-3}$ | $3.0\ 10^{-3}$-$1.1\ 10^{-2}$ |
| 20 | DYF1004 | 30 | 10 | $6.2\ 10^{-3}$ | $3.0\ 10^{-3}$-$1.1\ 10^{-2}$ |
| 21 | DYS1006 | 18 | 9 | $5.6\ 10^{-3}$ | $2.5\ 10^{-3}$-$1.1\ 10^{-2}$ |
| 22 | DYS1015 | 19 | 8 | $5.0\ 10^{-3}$ | $2.1\ 10^{-3}$-$9.7\ 10^{-3}$ |
| 23 | DYS563 | 11 | 6 | $3.7\ 10^{-3}$ | $1.4\ 10^{-3}$-$8.1\ 10^{-3}$ |
| 24 | DYS1011 | 23 | 5 | $3.1\ 10^{-3}$ | $1.4\ 10^{-3}$-$7.2\ 10^{-3}$ |
| 25 | DYS524 | 23 | 3 | $1.9\ 10^{-3}$ | $3.8\ 10^{-4}$-$5.4\ 10^{-3}$ |
| 26 | DYS1008 | 21 | 2 | $1.2\ 10^{-3}$ | $1.5\ 10^{-4}$-$4.5\ 10^{-3}$ |

Please note that the 7 RM Y-STRs under d) are the newly identified Y-STRs that were not known as Y-STRs before and for which we newly established mutation rates, demonstrating that these markers have mutation rates $>10^{-2}$ i.e. are RM Y-STRs. The 11 RM Y-STRs under c) include these 7 new RM Y-STRs from d) plus 4 previously identified Y-STRs for which no mutation rates were previously available and for which we newly established mutation rates, demonstrating that these markers have mutation rates $>10^{-2}$, i.e. are RM Y-STRs.

As can be seen in FIG. 6, for all types of male relatives separated by different numbers of meioses, male relative differentiation capacity is low for AmpFLSTR Yfiler Y-STRs, for example only 5% and 9% for father-son pairs (1 meiosis) and brothers (2 meioses), respectively. This male relative differentiation capacity increases by inclusion of the novel RM and FM Y-STR sets. Within the different RM Y-STR sets, it is observed that compared to the previously published RM Y-STR set, the differentiation capacity dropped for the 11 new RM Y-STRs, for example from 27% and 47% to 24% and 42% in father-son pairs and brothers, respectively. By adding the new FM Y-STRs to the new RM Y-STRs, the differentiation capacity increased again for example 28% and 48% for 1 and 2 meioses, respectively, reaching similar differentiation capacities as seen with the previous RM Y-STR set. Moreover, the differentiation capacity increased dramatically when combining the new RM Y-STRs with the previous RM Y-STRs e.g. 44% and 69% for 1 and 2 meioses, respectively. The highest male relative differentiation capacities were obtained when combining all newly and previously identified RM Y-STRs with all newly identified FM Y-STRs e.g. 48% and 73% for 1 and 2 meioses, respectively. Moreover, as expected, male differentiation capacities increased for all marker sets with increased number of meioses that separate the male relatives, which is explained by more meioses allowing more mutations to occur. For example, for relatives separated by 7 meioses and more, 99% are differentiated by the combined set of new and previously known RM Y-STRs and new FM Y-STRs Example 5: Empirical Determination of Male Relative Differentiation Rates Finally, to empirically test the ability of the newly identified RM Y-STRs and new FM Y-STRs to practically differentiate male relatives, they were genotyped in a set of additional 466 males who belong to 92 male pedigrees. These are independent samples not used for mutation rate estimations. These samples had previously been genotyped for the 16 AmpFLSTR Yfiler Y-STRs and for the 14 previously identified RM Y-STRs as described elsewhere (Adnan et al., 2016. Ibid) and we also genotyped them for the DYS724 recently identified as RM Y-STR by Claerhout et al. (Claerhout et al. 2018. Ibid). The male individuals were grouped for pairwise comparisons according to the number of genetic transfers (meioses) that separate the relative within the pair resulting in 298 father-son pairs (1 meiosis), 300 brother and grandfather-grandson pairs (2 meioses), 192 great grandfather—great grandson pairs and uncle—nephew pairs (3 meioses), and 158 first cousins and granduncle—grandnephew pairs (4 meioses). Male relative differentiation rates were estimated from the number of relative pairs differentiated by at least one Y-STR mutation divided by the total number of pairs analyzed per each group of male relative pairs. The same sets of Y-STRs were used for this analysis as used before for the differentiation capacity analysis shown in FIG. 6 to allow direct comparison for the overlapping types of male relative pairs (i.e. relatives separated by 1-4 meioses).

FIG. 7 shows the male differentiation rates of the different Y-STR sets. The empirically derived differentiation rates were generally somewhat lower compared to the estimates based on the mutation rates as displayed in FIG. 6. These differences may in part be explained by the relatively low sample size of the relative pairs we empirically analysed. Additionally, the pedigree samples stem from a South Asian population, while the mutation rate estimates were based on using European father-son pairs, thus a population effect cannot be excluded. The overall correlation between the differentiation capacities and differentiation rates (expected and empirical) is high.

As can be seen in FIG. 7, for all types of male relatives separated by 1-4 meioses, male relative differentiation rate is low for AmpFLSTR Yfiler Y-STRs for example 5% and 9% for father-son pairs (1 meiosis) and brothers (2 meioses), respectively, but increased for all RM and FM Y-STR sets. Within the different RM Y-STR sets, it is observed that compared to the previously published RM Y-STR set, the differentiation rate dropped for the 11 new RM Y-STRs, for example from 29% and 47% to 19% and 30% in father-son pairs and brothers, respectively. By adding the new FM Y-STRs to the new RM Y-STRs, the differentiation rate increased again for example 25% and 39% for 1 and 2 meioses, respectively, being lower than achieved with the previously known RM Y-STRs. Moreover, the differentiation rate increased dramatically when combining the new RM Y-STRs with the previous RM Y-STRs e.g. 42% and 60% for 1 and 2 meioses, respectively. The highest male relative differentiation rates were obtained when combining all newly and previously identified RM Y-STRs with all newly identified FM Y-STRs e.g. 44% and 64% for 1 and 2 meioses, respectively. Moreover, as expected, male differentiation rates increased for all marker sets with increased number of meioses that separate the male relatives, which is explained by more meioses allowing more mutations to occur.

To test the degree in which the 11 new RM Y-STRs (DYF1000, DYF1001, DYF1002, DYR88, DYS685, DYS688, DYS712, DYS1003, DYS1007, DYS1010 and DYS1012) contribute to male relative differentiation, the differentiation capacities when combining the 15 previously known RM Y-STRs with each of the 11 new RM Y-STRs were calculated (FIG. 8). The differentiation capacity is directly correlated to the mutation rates of the marker set; therefore, each individual Y-STR that is added increases the differentiation capacity, where The markers with the highest mutation rates have the largest positive effect on increasing the male relative differentiation capacity.

The same type of analysis was applied on the empirically derived differentiation rates (FIG. 9). In this analysis there are more stochastic effects in play and the observed increase in male relative differentiation rate is affected by multiple factors such as the number of tested relatives, but also by pure chance, in addition to the mutability of the Y-STR. Nevertheless, also in this empirical male relative differentiation analysis, as shown in FIG. 9, each individual of the 11 novel new RM Y-STR markers, when combined with the 15 previously identified RM Y-STRs, increased the male relative differentiation rate compared to the 15 previously identified RM Y-STRs alone. FIGS. 8 and 9 both show that although the effect of a single novel RM Y-STR on the male relative differentiation may be modest, the combined effect of all 11 new RM Y-STRs is very strong as seen in FIGS. 8 and 9, but as also seen in FIGS. 6 and 7, and is further enhanced by their combination with the 8 novel FM Y-STRs as seen in FIGS. 6 and 7.

Example 6: Minimal Number of RM Y-STRs Needed to Reach High Differentiation Rates Different combinations of RM Y-STRs can be used to reach high differentiation rates; here we used the differentiation rate data from Example 5 to determine how many RM Y-STRs would be needed to reach a differentiation rate of >60% for pairs of males separated by three generations. To this end 100.000 random combinations of the 26 known RM Y-STRs were made in silico, whereby each of the combinations contained at least one Y-STR from the group consisting of DYF1000, DYF1001, DYF1002, DYS1003, DYS1007, DYS1010 and DYS1012. Such combinations were made for a range of total markers from 2 to 26, in which the 26 markers contained all markers. In the latter case, all 100.000 random combinations contained the same RM Y-STRs. From each combination of markers the fraction of the 192 pairs of males separated by 3 generations that could be differentiated by at least one mutation was calculated. The distribution of these differentiation rates was visualized as boxplots in FIG. 10. This Figure shows that to achieve a differentiation rate of more than 60% in pairs of males that are separated by 3 generations, at least nine RM Y-STRs are needed. Examples of groups of nine RM Y-STR markers that achieve a differentiation rate of more than 60% are shown in Table 4.

TABLE 4

Groups of nine Y-STR markers, comprising at least one
marker selected from the group consisting of DYF1000,
DYF1001, DYF1002, DYS1003, DYS1007, DYS1010 and DYS1012
that achieve a differentiation rate of at least 60%

DYF1000, DYF1001, DYF1002, DYF399S1, DYS518, DYS612,
DYS627, DYS712 and DYS724
DYF1000, DYF1001, DYF399S1, DYF403S1a, DYF403S1b,
DYF404S1, DYS518, DYS526b and DYS724
DYF1000, DYF1001, DYF399S1, DYF403S1a, DYR88, DYS518,
DYS570, DYS612 and DYS724
DYF1000, DYF1001, DYF399S1, DYF403S1b, DYF404S1,
DYS518, DYS526b, DYS685 and DYS724
DYF1000, DYF1001, DYF399S1, DYF403S1b, DYS1003, DYS518,
DYS612, DYS688 and DYS724
DYF1000, DYF1001, DYF399S1, DYF403S1b, DYS1003, DYS518,
DYS612, DYS712 and DYS724
DYF1000, DYF1001, DYF399S1, DYF403S1b, DYS1007, DYS518,
DYS612, DYS685 and DYS724
DYF1000, DYF1001, DYF399S1, DYF403S1b, DYS1012, DYS518,
DYS612, DYS712 and DYS724
DYF1000, DYF1001, DYF399S1, DYF403S1b, DYS518, DYS526b,
DYS612, DYS626 and DYS724
DYF1000, DYF1001, DYF399S1, DYR88, DYS449, DYS518,
DYS612, DYS627 and DYS724
DYF1000, DYF1001, DYF399S1, DYR88, DYS518, DYS612,
DYS626, DYS688 and DYS724
DYF1000, DYF1001, DYF399S1, DYS1007, DYS518, DYS526b,
DYS576, DYS612 and DYS724
DYF1000, DYF1001, DYF399S1, DYS449, DYS518, DYS526b,
DYS612, DYS685 and DYS724
DYF1000, DYF1001, DYF399S1, DYS518, DYS526b, DYS612,
DYS627, DYS685 and DYS724
DYF1000, DYF1001, DYF399S1, DYS518, DYS526b, DYS612,
DYS627, DYS712 and DYS724
DYF1000, DYF399S1, DYF403S1a, DYF403S1b, DYS518,
DYS526b, DYS612, DYS685 and DYS724

In addition, it was found that when combining a total of 18 RM Y-STRs more than half of the combinations reached a differentiation rate surpassing 60%; lastly, when combining 24 RM Y-STRs all combinations resulted in a differentiation rate greater than 60%.

In addition, the 100.000 random combinations of 26 RM Y-STRs made in silico were used to calculate the differentiation capacities of each combination. For each combination of markers, the differentiation capacity was calculated based on the mutation rate of the individual markers. The distribution of these differentiation capacities was visualized as boxplots in FIG. 11. This Figure shows that to achieve a differentiation rate of more than 62% in pairs of males that are separated by 3 generations, at least nine RM Y-STRs are needed. Examples of groups of nine RM Y-STR markers that achieve a differentiation capacity of more than 62% are shown in Table 5.

TABLE 5

Groups of nine Y-STR markers, comprising at least one marker
selected from the group consisting of DYF1000, DYF1001,
DYF1002, DYS1003, DYS1007, DYS1010 and DYS1012 that achieve
a differentiation capacity of at least 62%.

DYF1000, DYF1001, DYF399S1, DYF403S1a, DYS547, DYS576,
DYS688, DYS712 and DYS724
DYF1000, DYF1001, DYF399S1, DUR88, DYS518, DYS570,
DYS688, DYS712 and DYS724
DYF1000, DYF1001, DYS399S1, DYF403S1a, DYR88, DYS1012,
DYS518, DYS688 and DYS724
DYF1000, DYF1001, DYF399S1, DYF403S1a, DYR88, DYS547,
DYS688, DYS712 and DYS724
DYF1000, DYF1001, DYF399S1, DYF403S1a, DYR88, DYS518,
DYS688, DYS712 and DYS724

In addition, it was found that when combining a total of 15 RM Y-STRs more than half of the combinations reached a differentiation rate surpassing 62%; lastly, when combining 21 RM Y-STRs all combinations resulted in a differentiation rate greater than 62%.

Example 7: Optimized PCR Assays to Amplify RM
Y-STRs More Efficiently

Y-STRs can be amplified together in multiplex PCR reactions, to test the empirical mutation rates of the 26 RM Y-STRs (See Examples 2 and 3) six different multiplex PCR reactions were used. In practice, it is preferable to amplify all empirically confirmed RM Y-STRs together in as little multiplex PCR reactions as possible. To this end we developed two multiplex PCR assays that can amplify all 26 currently known RM Y-STRs together with four FM Y-STRs. Table 6 shows the primers that were used for this PCR assay, to allow this large number of Y-STRs to be separated sufficiently using capillary electrophoresis. Many of the primer sequences as shown in Table 2 had to be replaced by new primers. It was shown that by using fluorescently labeled primers the two PCR assays could be used to type males for all of the target Y-STRs using capillary electrophoresis, also in the presence of female DNA. Moreover, it was shown that by using unlabeled primers it was possible to use the amplified fragments resulting from these two PCR assays to type males using next generation sequencing on an Illumina MiSeq instrument. The latter type of analysis resulted in exact knowledge about the underlying sequences of these Y-STRs and could potentially lead to further improved differentiation of both related and unrelated males.

TABLE 6

| Alternative forward and reverse primers designed for amplification of the Y-STR markers. | | |
| --- | --- | --- |
| Marker name | Forward primer | Reverse primer |
| DYF393S1 | AAGCAGAGCC ACACAGACT (SEQ ID NO 91) | GTTTGCCTGT AAGTGGAGCC (SEQ ID NO 92) |

TABLE 6-continued

Alternative forward and reverse
primers designed for amplification
of the Y-STR markers.

| Marker name | Forward primer | Reverse primer |
|---|---|---|
| DYS627 | ACAGCGCAGG ATTCCATCTA (SEQ ID NO 93) | TGCCTTTCAT TCTCTCCTTC G (SEQ ID NO 94) |
| DYS570 | GAGGAGATTA GGARCACAGT GA (SEQ ID NO 95) | TGCAAGGTGT GGGTGAAAAT T (SEQ ID NO 96) |
| DYS713/ DYS685 | CTGGGTGTGC ATTCGAGACT (SEQ ID NO 97) | GTTGCAGGGA GTGGAGATTG (SEQ ID NO 98) |
| DYS526b | GCCCTTGTTT CTATAAGTGG TCA (SEQ ID NO 99) | GTTTGGGTTA CTTCGCCAGA (SEQ ID NO 100) |
| DYF1000 | CAGGGAGCTT CAGTGTGC (SEQ ID NO 101) | TGGCTCAGCT CACAGTAGAA (SEQ ID NO 102) |
| DYS518 | TGGGCCAAGA TCTCGTCATT (SEQ ID NO 103) | TCACATGTAG CACTCTGGGC (SEQ ID NO 104) |
| DYS1003 | CAGTCAGCCA AGATGCCAAA (SEQ ID NO 105) | GCAACACTTA AGAGACGGCA (SEQ ID NO 106) |
| DYS1012 | GCAAGACTCC ATCTCCAAAA AG (SEQ ID NO 107) | CAAGCTTGGG TCCATTATGA (SEQ ID NO 108) |
| DYS1005 | TGGATGGAAG TGGTACCTCT G (SEQ ID NO 109) | AGGTTGTGGT AATCTGAGAT TGC (SEQ ID NO 110) |
| DYS1010 | CTACTCCAAA GGCTGCAGGA (SEQ ID NO 111) | CGCCCTCACA CCCTTTCTTT (SEQ ID NO 112) |
| DYS1007 | GGTAAGATAA TATGGCACCG TGG (SEQ ID NO 113) | CCCTCCTTCC CTCCTTATCT C (SEQ ID NO 114) |
| DYR88 | GCGAGACTCC ATCTCAACA (SEQ ID NO 115) | CCACCCAAAT CTCACGT (SEQ ID NO 116) |
| DYF404S1 | AGTACTTTGA GTTTCCCAGA AGG (SEQ ID NO 117) | AAGGAGCCCA GGATTGAGAG (SEQ ID NO 118) |
| DYF387S1 | GTCTCACTAG CTGGTCAGGG (SEQ ID NO 119) | GTCGTGGTGG TAAGTGCATT (SEQ ID NO 120) |
| DYS1013 | TCTGACTCCT TGACTCCCAA (SEQ ID NO 121) | TGTCTCTCTG TCTGCCTGC (SEQ ID NO 122) |
| DYS712 | TTGAGCCCAG AAGTTCAAGA A (SEQ ID NO 123) | GGTACCTTGT ATTTTCCACA GGA (SEQ ID NO 124) |
| DYS711/ DYS688 | TGGTGATTAC ATATTGCAGA GCC (SEQ ID NO 125) | GCTGTCATTG TATCTCTTCA CTC (SEQ ID NO 126) |
| DYS626 | AGCTGAGGAA GAGAATGGCG (SEQ ID NO 127) | GCAAATGTAA GTCTGTCTCT GGA (SEQ ID NO 128) |

TABLE 6-continued

Alternative forward and reverse
primers designed for amplification
of the Y-STR markers.

| Marker name | Forward primer | Reverse primer |
| --- | --- | --- |
| DYF399S1 | TTGCATAGGT AGAGGGAGGC (SEQ ID NO 129) | GCTTAGGATT GGACCCAGGA (SEQ ID NO 130) |
| DYS449 | GTCTCTCAAG CCTGTTCTAT GA (SEQ ID NO 131) | TGGACAACAA GAGTAAGACA GAA (SEQ ID NO 132) |
| DYS724 | TGATGGCTCA TTGTAGTCCA C (SEQ ID NO 133) | AGCTGTTAAC CTTCCCAAAT TGT (SEQ ID NO 134) |
| DYS547 | TCTGTTTCTG CATTGTTTCA CTT (SEQ ID NO 135) | TGAGTGACAG AGCATAAACG TG (SEQ ID NO 136) |
| DYS576 | TCTCAGCCAA GCAACATAGC (SEQ ID NO 137) | TGGCAGTCTC ATTTCCTGGA (SEQ ID NO 138) |
| DYS612 | GCAGAAAGGG CCTTAAGACA (SEQ ID NO 139) | CTTGACACTT GCCATGGGTA (SEQ ID NO 140) |
| DYF1002 | GCGAGGGGTA AGTAGTGGAA (SEQ ID NO 141) | ACATCACATC TCTCCTTCCT TCT (SEQ ID NO 142) |
| DYF1001 | GTTGTGGTGA TCTGAGATTG CT (SEQ ID NO 143) | ACTGGATGGA AGTGGTACCT (SEQ ID NO 144) |
| DYF403S1a | GGYAACAGAG CAGGATTCCA TCTA (SEQ ID NO 145) | ACATAGTTCA AAATTCATGT GGATAATGA (SEQ ID NO 146) |
| DYS442 | CGGAGGAAAA GAAGTGATTG TAC (SEQ ID NO 147) | CCCCAAAGTG TGTTGCATCA (SEQ ID NO 148) |
| DYF403S1b | GGYAACAGAG CAGGATTCCA TCTA (SEQ ID NO 149) | ACATAGTTTG AAATTCATGT GGATAATGA (SEQ ID NO 150) |

Primers in bold represent alternative primers to amplify the same Y-STRs as listed in Table 2.

The invention claimed is:

1. A method comprising:

(i) contacting a sample comprising a DNA sample of a male individual with a set of amplification primers comprising primers for the amplification of at least one allele of at least one RM Y STR marker selected from the group consisting of DYF1001 comprising SEQ ID NO: 67 or 68 or 69, DYF1002 comprising SEQ ID NO: 71 or 72, DYR88 comprising SEQ ID NO: 89 or 90, DYS1003 comprising SEQ ID NO: 73, DYS1007 comprising SEQ ID NO: 74, DYS1010 comprising SEQ ID NO: 75 and DYS1012 comprising SEQ ID NO: 76, (ii) amplifying the at least one allele of at least one RM Y-STR marker; thereby forming one or more amplicons of the allele, (iii) identifying the at least one allele by sequencing the one or more amplicons of the allele.

2. The method according to claim 1, wherein the paternally related male is a father, son or brother of the male individual.

3. The method according to claim 1, comprising at least one RM Y-STR marker selected from the group consisting of DYF1001, DYF1002, DYS1003, DYS1007, DYS1010 and DYS1012.

4. The method according to claim 1, wherein the RM Y-STR markers comprise: DYF1001, DYF1002, DYS1003, DYS1007, DYS1010 and DYS1012.

5. The method according to claim 1, wherein at least two RM Y-STR markers are selected from the group consisting of, DYF1001, DYF1002, DYR88, DYS1003, DYS1007, DYS1010, and DYS1012.

6. The method according to claim 1, wherein the RM Y-STR markers are DYF1001, DYF1002, DYR88, DYS1003, DYS1007, DYS1010, and DYS1012.

7. The method according to claim 1, wherein the RM Y-STR markers further comprise all markers from the group consisting of DYF387S1, DYF399S1, DYF403S1A, DYF403S1B, DYF404S1, DYS449, DYS518, DYS526, DYS547, DYS570, DYS576, DYS612, DYS626, DYS627, DYS724, DYS688 comprising SEQ ID NO 70, DYS685 comprising SEQ ID NO 77, DYF1000 comprising SEQ ID NO: 63, 64, 65, or 66, and DYS712 comprising SEQ ID NO 78.

8. The method according to claim 1, wherein the method comprises amplifying at least one allele of at least one Y-STR marker using a set of amplification primers configured to provide one or more amplicons of the at least one RM-YSTR marker, wherein the sequences of the amplification primers are as follows: SEQ ID NOs: 9-10 for DYF1001, SEQ ID NOs: 21-22 for DYF1002, SEQ ID NOs: 29-30 for DYS1003, SEQ ID NOs: 23-24 for DYS1007, SEQ ID NOs: 25-26 for DYS1010, SEQ ID NOs: 19-20 for DYS1012, and SEQ ID NOs: 13-14 for DYR88.

9. The method according to claim 1, wherein the method comprises amplifying at least one allele of at least one Y-STR marker using a set of amplification primers configured to provide one or more amplicons of the at least one RM Y-STR marker, wherein the sequences of the amplification primers are as follows: SEQ ID NOs: 143-144 for DYF1001, SEQ ID NOs: 141-142 for DYF1002, SEQ ID NOs: 105-106 for DYS1003, SEQ ID NOs: 113-114 for DYS1007, SEQ ID NOs: 111-112 for DYS1010, SEQ ID NOs: 107-108 for DYS1012, and SEQ ID NOs: 115-116 for DYR88.

10. The method according to claim 1, wherein at least one of the amplification primers is fluorescently labeled, so as to label the one or more amplicons with a fluorescent label.

11. The method according to claim 1, wherein at least one identified mutation in said RM Y-STR marker is not shared by all male relatives.

12. The method according to claim 1, further comprising one or more RM Y-STR markers selected from the group consisting of DYF387S1, DYF399S1, DYF403S1A, DYF403S1B, DYF404S1, DYS449, DYS518, DYS526, DYS547, DYS570, DYS576, DYS612, DYS626, DYS627, DYS724, DYS688 defined by SEQ ID NO 70, DYS685, DYF1000, and DYS712.

13. The method according to claim 1, wherein at least 9 RM Y-STR markers selected from the combinations comprising:

(i) DYF1000, DYF1001, DYF399S1, DYF403S1a, DYS547, DYS576, DYS688, DYS712 and DYS724;

(ii) DYF1000, DYF1001, DYF399S1, DYR88, DYS518, DYS570, DYS688, DYS712, and DYS724;

(iii) DYF1000, DYF1001, DYS399S1, DYF403S1a, DYR88, DYS1012, DYS518, DYS688, and DYS724;

(iv) DYF1000, DYF1001, DYF399S1, DYF403S1a, DYR88, DYS547, DYS688, DYS712, and DYS724; and (v) DYF1000, DYF1001, DYF399S1, DYF403Sla, DYS518, DYS688, DYS712, and DYS724.

14. A method for amplifying an allele of at least one RM Y-STR marker, the method comprising:

contacting a sample comprising a DNA sample of a male individual with a set of primers comprising primers for the amplification of at least one allele of at least one RM Y-STR marker selected from the group consisting of DYF1001, DYF1002, DYS1003, DYS1007, A DYS1010, DYS1012, and DYR88; and amplifying an allele of the at least one Y-STR marker, thereby form-
ing one or more amplicons of the allele.

15. The method according to claim 14, wherein the set of
primers further comprises primers for the amplification of an
allele of at least one RM Y-STR selected from the group
consisting of DYS685, DYS688, DYS712, and DYF1000.

16. The method according to claim 14, further comprising
labeling the one or more amplicons with a fluorescent label.

17. A method for identifying an allele of at least one RM
Y-STR marker, comprising:

contacting a sample comprising DNA of a male individual
    with a set of primers;
  amplifying the DNA; and
  detecting an allele of at least one RM Y-STR selected
    from DYF1001, DYF1002, DYS1003, DYS1007,
    DYS1010, DYS1012, and DYR88 by sequencing the
    amplified DNA sample.

18. The method according to claim 17, further comprising
identifying an allele of at least one RM Y-STR selected from
the group consisting of DYS685, DYS688, DYS712, and
DYF1000.

94

19. The method according to claim 17, wherein the
sequences of the amplification primers are:

SEQ ID NOs: 9-10 for DYF1001,
  SEQ ID NOs: 21-22 for DYF1002,
  SEQ ID NOs: 29-30 for DYS1003,
  SEQ ID NOs: 23-24 for DYS1007,
  SEQ ID NOs: 25-26 for DYS1010,
  SEQ ID NOs: 19-20 for DYS1012, and
  SEQ ID NOs: 13-14 for DYR88.

20. The method according to claim 17, wherein the
sequences of the amplification primers are:

SEQ ID NOs: 143-144 for DYF1001,
  SEQ ID NOs: 141-142 for DYF1002,
  SEQ ID NOs: 105-106 for DYS1003,
  SEQ ID NOs: 113-114 for DYS1007,
  SEQ ID NOs: 111-112 for DYS1010,
  SEQ ID NOs: 107-108 for DYS1012, and
  SEQ ID NOs: 115-116 for DYR88.

* * * * *